US009186369B2

(12) United States Patent
Storer et al.

(10) Patent No.: US 9,186,369 B2
(45) Date of Patent: Nov. 17, 2015

(54) PURINE NUCLEOSIDE ANALOGUES FOR TREATING FLAVIVIRIDAE INCLUDING HEPATITIS C

(71) Applicants: Idenix Pharmaceuticals, Inc., Cambridge, MA (US); The Centre National de la Recherche Scientifique, Paris-Cedex (FR); L'Universite Montpellier II, Montpellier (FR)

(72) Inventors: Richard Storer, Folkestone (GB); Gilles Gosselin, Montpellier (FR); David Dukhan, Montpellier (FR); Frederic Leroy, Jonquieres (FR)

(73) Assignee: Idenix Pharmaceuticals, LLC, Cambridge, MA (US)

( * ) Notice: Subject to any disclaimer, the term of this patent is extended or adjusted under 35 U.S.C. 154(b) by 0 days.

(21) Appl. No.: 14/269,003

(22) Filed: May 2, 2014

(65) Prior Publication Data
US 2014/0234251 A1   Aug. 21, 2014

Related U.S. Application Data

(60) Division of application No. 12/270,795, filed on Nov. 13, 2008, now Pat. No. 8,742,101, which is a continuation of application No. 10/900,008, filed on Jul. 26, 2004, now abandoned.

(60) Provisional application No. 60/490,216, filed on Jul. 25, 2003.

(51) Int. Cl.
| C07H 19/23 | (2006.01) |
| C07D 487/04 | (2006.01) |
| C07D 405/04 | (2006.01) |
| C07D 409/04 | (2006.01) |
| A61K 31/7052 | (2006.01) |
| A61K 31/5025 | (2006.01) |
| A61K 31/53 | (2006.01) |
| A61P 31/14 | (2006.01) |
| A61K 31/706 | (2006.01) |
| A61K 31/00 | (2006.01) |
| C07H 19/044 | (2006.01) |
| C07H 19/052 | (2006.01) |
| C07H 19/056 | (2006.01) |
| A61K 45/06 | (2006.01) |
| C07H 19/04 | (2006.01) |

(52) U.S. Cl.
CPC .............. *A61K 31/706* (2013.01); *A61K 31/00* (2013.01); *A61K 45/06* (2013.01); *C07H 19/04* (2013.01); *C07H 19/044* (2013.01); *C07H 19/052* (2013.01); *C07H 19/056* (2013.01); *C07H 19/23* (2013.01)

(58) Field of Classification Search
CPC ...... C07H 19/23; C07H 19/12; C07D 487/04; C07D 405/04; C07D 409/04; A61K 31/7052; A61K 31/5025; A61K 31/53; A61K 45/06
USPC .............. 536/27.13; 514/43, 45, 48; 544/236
See application file for complete search history.

(56) References Cited

U.S. PATENT DOCUMENTS

| 3,798,209 A | 3/1974 | Witkowski et al. |
| RE29,835 E | 11/1978 | Witkowski et al. |
| 4,211,771 A | 7/1980 | Witkowski et al. |
| 4,522,811 A | 6/1985 | Eppstein et al. |
| 5,026,687 A | 6/1991 | Yarchoan et al. |
| 5,055,394 A | 10/1991 | Kopecko et al. |
| 5,149,794 A | 9/1992 | Yatvin et al. |
| 5,194,654 A | 3/1993 | Hostetler et al. |
| 5,223,263 A | 6/1993 | Hostetler et al. |
| 5,372,808 A | 12/1994 | Blatt et al. |
| 5,496,546 A | 3/1996 | Wang et al. |
| 5,538,865 A | 7/1996 | Reyes et al. |
| 5,610,054 A | 3/1997 | Draper |
| 5,633,358 A | 5/1997 | Gruetzke et al. |
| 5,676,942 A | 10/1997 | Testa et al. |
| 5,725,859 A | 3/1998 | Omer |
| 5,738,845 A | 4/1998 | Imakawa |
| 5,830,455 A | 11/1998 | Valtuena et al. |
| 5,837,257 A | 11/1998 | Tsai et al. |
| 5,846,964 A | 12/1998 | Ozeki |
| 5,849,696 A | 12/1998 | Chretien et al. |
| 5,869,253 A | 2/1999 | Draper |

(Continued)

FOREIGN PATENT DOCUMENTS

| DE | 19914474 | 10/1999 |
| EP | 0350287 | 1/1990 |

(Continued)

OTHER PUBLICATIONS

Bussolari et al. J. Med. Chem. 1993, 36(25) 4113-4120.*
Meade et al. J. Med. Chem. 1992, 35(3) 526-533.*
Acedo et al., "Synthesis and Biophysical and Biological Properties of Oligonucleotides Containing 2-Aza-2'-Deoxyinosine," *J. Org. Chem.* 1995, vol. 60, pp. 6262-6269.
Alt et al., "Core specific antisense phosphorothioate oligodeoxynucleotides as potent and specific inhibitors of hepatitis C viral translation," *Arch. Virol.* 1997, vol. 142, pp. 589-599.

(Continued)

*Primary Examiner* — Venkataraman Balasubramanian
(74) *Attorney, Agent, or Firm* — Jones Day

(57) ABSTRACT

This invention is directed to a method for treating a host, especially a human, infected with hepatitis C, flavivirus and/or pestivirus, comprising administering to that host an effective amount of an anti-HCV biologically active pentofuranonucleoside where the pentofuranonucleoside base is an optionally substituted 2-azapurine. The optionally substituted pentofuranonucleoside, or a salt or prodrug thereof, may be administered alone or in combination with one or more optionally substituted pentofuranonucleosides or other anti-viral agents.

28 Claims, 3 Drawing Sheets

(56) References Cited

U.S. PATENT DOCUMENTS

| | | |
|---|---|---|
| 5,874,565 A | 2/1999 | Rice et al. |
| 5,891,874 A | 4/1999 | Colacino et al. |
| 5,990,276 A | 11/1999 | Zhang et al. |
| 6,004,933 A | 12/1999 | Spruce et al. |
| 6,034,134 A | 3/2000 | Gold et al. |
| 6,043,077 A | 3/2000 | Barber et al. |
| 6,056,961 A | 5/2000 | Lavie et al. |
| 6,100,024 A | 8/2000 | Hudson et al. |
| 6,326,151 B1 | 12/2001 | Katze et al. |
| 6,340,690 B1 | 1/2002 | Bachand et al. |
| 6,348,587 B1 | 2/2002 | Schinazi et al. |
| 6,379,886 B1 | 4/2002 | Takahama et al. |
| 6,403,566 B1 | 6/2002 | Wang |
| 6,410,531 B1 | 6/2002 | Llina-Brunet et al. |
| 6,416,944 B1 | 7/2002 | Chien et al. |
| 6,416,946 B1 | 7/2002 | Chien et al. |
| 6,420,380 B2 | 7/2002 | Llina-Brunet et al. |
| 6,436,666 B1 | 8/2002 | Chien et al. |
| 6,495,677 B1 | 12/2002 | Ramasamy et al. |
| 6,534,523 B1 | 3/2003 | Llina-Brunet et al. |
| 6,566,365 B1 | 5/2003 | Storer |
| 6,573,248 B2 | 6/2003 | Ramasamy et al. |
| 6,660,721 B2 | 12/2003 | Devos et al. |
| 7,217,815 B2 * | 5/2007 | An et al. .................. 536/27.62 |
| 8,742,101 B2 * | 6/2014 | Storer et al. .................. 544/180 |
| 2002/0019363 A1 | 2/2002 | Ismaili et al. |
| 2002/0055483 A1 | 5/2002 | Watanabe et al. |
| 2002/0099072 A1 | 7/2002 | Bachand et al. |
| 2002/0147160 A1 | 10/2002 | Bhat et al. |
| 2002/0198171 A1 | 12/2002 | Schinazi et al. |
| 2003/0008841 A1 | 1/2003 | Devos et al. |
| 2003/0028013 A1 | 2/2003 | Wang et al. |
| 2003/0050229 A1 | 3/2003 | Sommadossi et al. |
| 2003/0060400 A1 | 3/2003 | La Colla et al. |
| 2003/0083307 A1 | 5/2003 | Devos et al. |
| 2003/0087873 A1 | 5/2003 | Stuyver et al. |
| 2003/0225029 A1 | 12/2003 | Stuyver et al. |
| 2003/0225037 A1 | 12/2003 | Storer |
| 2004/0002479 A1 | 1/2004 | Wang et al. |
| 2004/0006002 A1 | 1/2004 | Sommadossi et al. |
| 2004/0006007 A1 | 1/2004 | Gosselin et al. |
| 2004/0063622 A1 | 4/2004 | Sommadossi et al. |
| 2004/0063658 A1 | 4/2004 | Roberts et al. |
| 2004/0067877 A1 | 4/2004 | Schinazi et al. |
| 2004/0067901 A1 | 4/2004 | Bhat et al. |
| 2004/0072788 A1 | 4/2004 | Bhat et al. |
| 2004/0077587 A1 | 4/2004 | Sommadossi et al. |
| 2004/0082574 A1 | 4/2004 | Wang et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0110718 A1 | 6/2004 | Devos et al. |

FOREIGN PATENT DOCUMENTS

| | | |
|---|---|---|
| EP | 0650371 | 5/1995 |
| EP | 1043399 | 10/2000 |
| JP | 03-148278 | 6/1991 |
| JP | 05-111389 | 5/1993 |
| JP | 08268890 | 10/1996 |
| JP | 10101591 | 4/1998 |
| WO | WO 88/02785 | 4/1988 |
| WO | WO 89/02733 | 4/1989 |
| WO | WO 90/00555 | 1/1990 |
| WO | WO 91/16920 | 1/1991 |
| WO | WO 91/18914 | 12/1991 |
| WO | WO 91/19721 | 12/1991 |
| WO | WO 93/00910 | 1/1993 |
| WO | WO 94/26273 | 11/1994 |
| WO | WO 96/15132 | 5/1996 |
| WO | WO 97/12033 | 4/1997 |
| WO | WO 97/36554 | 10/1997 |
| WO | WO 98/16184 | 4/1998 |
| WO | WO 98/17679 | 4/1998 |
| WO | WO 98/22496 | 5/1998 |
| WO | WO 99/07734 | 2/1999 |
| WO | WO 99/43691 | 9/1999 |
| WO | WO 00/06529 | 2/2000 |
| WO | WO 00/50424 | 8/2000 |
| WO | WO 01/16149 | 3/2001 |
| WO | WO 01/32153 | 5/2001 |
| WO | WO 01/60315 | 8/2001 |
| WO | WO 01/68663 | 9/2001 |
| WO | WO 01/79246 | 10/2001 |
| WO | WO 01/90121 | 11/2001 |
| WO | WO 01/92282 | 12/2001 |
| WO | WO 02/03997 | 1/2002 |
| WO | WO 02/06246 | 1/2002 |
| WO | WO 02/08187 | 1/2002 |
| WO | WO 02/08198 | 1/2002 |
| WO | WO 02/08251 | 1/2002 |
| WO | WO 02/08256 | 1/2002 |
| WO | WO 02/18404 | 3/2002 |
| WO | WO 02/32920 | 4/2002 |
| WO | WO 02/48116 | 6/2002 |
| WO | WO 02/48157 | 6/2002 |
| WO | WO 02/48165 | 6/2002 |
| WO | WO 02/48172 | 6/2002 |
| WO | WO 02/057287 | 7/2002 |
| WO | WO 02/057425 | 7/2002 |
| WO | WO 02/060926 | 8/2002 |
| WO | WO 02/094289 | 11/2002 |
| WO | WO 02/100415 | 12/2002 |
| WO | WO 03/026589 | 4/2003 |
| WO | WO 03/026675 | 4/2003 |
| WO | WO 03/040112 | 5/2003 |
| WO | WO 03/051899 | 6/2003 |
| WO | WO 03/061385 | 7/2003 |
| WO | WO 03/061576 | 7/2003 |
| WO | WO 03/062211 | 7/2003 |
| WO | WO 03/062255 | 7/2003 |
| WO | WO 03/062256 | 7/2003 |
| WO | WO 03/062257 | 7/2003 |
| WO | WO 03/063794 | 8/2003 |
| WO | WO 03/068162 | 8/2003 |
| WO | WO 03/068164 | 8/2003 |
| WO | WO 03/072757 | 9/2003 |
| WO | WO 03/077928 | 9/2003 |
| WO | WO 03/093290 | 11/2003 |
| WO | WO 2004/000858 | 12/2003 |
| WO | WO 2004/002422 | 1/2004 |
| WO | WO 2004/002999 | 1/2004 |
| WO | WO 2004/003000 | 1/2004 |
| WO | WO 2004/003138 | 1/2004 |
| WO | WO 2004/007512 | 1/2004 |
| WO | WO 2004/009020 | 1/2004 |
| WO | WO 2004/013298 | 2/2004 |
| WO | WO 2004/013300 | 2/2004 |
| WO | WO 2004/018463 | 3/2004 |
| WO | WO 2004/028481 | 4/2004 |
| WO | WO 2004/037159 | 5/2004 |
| WO | WO 2004/043159 | 5/2004 |
| WO | WO 2004/046331 | 6/2004 |
| WO | WO 2004/052899 | 6/2004 |

OTHER PUBLICATIONS

Alt et al., "Specific inhibition of hepatitis C viral gene expression by antisense phosphorothioate oligodeoxynucleotides," *Hepatology* 1995, vol. 22, pp. 707-717.

Andres et al., "Synthesis of 8-methyl-2-azainosine and related nucleosides," *J. Heterocyclic Chem.* 1984, vol. 21, pp. 1221-1224.

Attwood et al., "The design and synthesis of potent inhibitors of hepatitis C virus NS3-4A proteinase," *Antivir. Chem. Chemother.* 1999, vol. 10, pp. 259-273.

Bank et al., "Modern Pharmaceutical, 3ed." Marcel Dekker, New York, 1996, pp. 451 and 596.

Baraldi et al., "Synthesis and anti-HSV-1 activity of 6 substituted pyrazolo[3,4-d]pyridazin-7-one nucleosides," *Nucleosides and Nucleotides* 1998, vol. 17, pp. 2165-2173.

(56) References Cited

OTHER PUBLICATIONS

Bartenschlager et al., "Kinetic and structural analyses of hepatitis C virus polyprotein processing," *J. Virol.* 1994, vol. 68, pp. 5045-5055.
Bartenschlager et al., "Nonstructural protein 3 of the hepatitis C virus encodes a serine-type proteinase required for cleavage at the NS3/4 and NS4/5 junctions," *J. Virol.* 1993, vol. 67, pp. 3835-3844.
Battaglia et al., "Combination therapy with interferon and ribavirin in the treatment of chronic hepatitis C infection," *Ann. Pharmacother.* 2000, vol. 34, pp. 487-494.
Bazan et al., "Detection of a trypsin-like serine protease domain in flaviviruses and pestviruses," *Virology* 1989, vol. 171, pp. 637-639.
Beaulieu et al., "Non-nucleoside inhibitors of the hepatitis C virus NS5B polymerase: discovery and preliminary SAR of benzimidazole derivatives," *Bioorg. Med. Chem. Lett.* 2004, vol. 14, pp. 119-124.
Beaulieu et al., "Non-nucleoside inhibitors of the hepatitis C virus NS5B polymerase: discovery of benzimidazole 5-carboxylic amide derivatives with low-nanomolar potency," *Bioorg. Med. Chem. Lett.* 2004, vol. 14, pp. 967-971.
Behrens et al., "Identification and properties of the RNA-dependent RNA polymerase of hepatitis C virus," *EMBO J.* 1996, vol. 15, pp. 12-22.
Berenguer et al., "Hepatitis C virus in the transplant setting," *Antivir. Ther.* 1998, vol. 3(suppl. 3), pp. 125-136.
Bhat et al., "Synthesis and pharmacokinetic properties of nucleoside nanalogues as possible inhibitors of HCV RNA replication," Oral Session V, Hepatitis C Virus, Flaviviridae, 16th International Conference on Antiviral Research, Apr. 27, 2003, Savanah, GA., p. A75.
Boernke et al., "Effects of self-association of ornithine aminotransferase on its physicochemical characteristics," *Biochemistry*, 1981, vol. 20, pp. 115-120.
Boyer et al., "Pathogenesis, diagnosis and management of hepatitis C," *J. Hepatol.* 2000, vol. 32, pp. 98-112.
Bressanelli et al., "Structural Analysis of the Hepatitis C Virus RNA Polymerase in Complex with Ribonucleotides," *J. Virol.* 2002, vol. 76, pp. 3482-3492.
Bussolari et al., "Synthesis and anti-HIV evaluation of 2',3'-dideoxy imidazo- and nu-triazolo[4,5-d]pyridazine nucleosides," *Bioorg. Med. Chem. Lett.* 1999, vol. 7, pp. 2373-2379.
Bussolari et al., "Synthesis and biological evaluation of N4-substituted imidazo- and v-triazolo[4,5-d]pyridazine nucleosides," *J. Med. Chem.* 1903, vol. 36, pp. 4113-4120.
Bussolari et al., "Synthesis and biological evaluation of N4-substituted imidazo- and v-Triazolo[4,5-d]pyridazine nucleosides," *J. Med. Chem.* 1993, vol. 36, pp. 4113-4120.
Bussolari et al., "The synthesis and biological evaluation of 4-p-nitrobenzylthio-v-triazolo [4,5-d]pyridazine and imidazo[4,5-d]pyridazine ribosides as potential nucleoside transport inhibitors," *Bioorg. Med. Chem.* 1996, vol. 4, pp. 1725-1731.
Bymock et al., "Novel approaches to the treatment of hepatitis C virus infection," *Antivir. Chem. Chemother.* 2000, vol. 11, pp. 79-96.
Calisher et al., "Antigenic Relationships between Flaviviruses as Determined by Cross-neutralization Tests with Polyclonal Antisera," *J. Gen. Virol.* 1989, vol. 70, pp. 37-43.
Chan et al., "Discovery of thiophene-2-carboxylic acids as potent inhibitors of HCV NS5B polymerase and HCV subgenomic RNA replication. Part 1: Sulfonamides," *Bioorg. Med. Chem. Lett.* 2004, vol. 14, pp. 793-796.
Chan et al., "Discovery of thiophene-2-carboxylic acids as potent inhibitors of HCV NS5B polymerase and HCV subgenomic RNA replication. Part 2: Tertiary amides," *Bioorg. Med. Chem. Lett.* 2004, vol. 14, pp. 797-800.
Chan et al., "Identification of N,N-Disubstituted Phenylalanines as a Novel Class of Inhibitors of Hepatitis C NS5B Polymerase," *J. Med. Chem.* 2003, vol. 46, pp. 1283-1285.
Chen et al., "Synthesis and biological evaluation of certain 4-alkylamino and 4-arylakylamino derivatives of the imidazo[4,5-d]pyridazine and v-triazolo[4,5-d]pyridazine ring systems (1a)," *J. Heterocyclic Chem.* 1982, vol. 19, pp. 285-288.

Chu et al., "Structure of Sch 68631: A new hepatitis C virus proteinase inhibitor from *Streptomyces sp.*," *Tetrahedron Letters* 1996, vol. 37, pp. 7229-7232.
Davis, "Current therapy for chronic hepatitis C," *Gastroenterology* 2000, vol. 118, pp. S104-S114.
De Francesco et al., "Approaching a new era for hepatitis C virus therapy inhibition of the NS3-4A serine protease and the NS5B RNA-dependent RNA polymerase," *Antiviral Res.* 2003, vol. 58, pp. 1-16.
Di Besceglie et al., Scientific American 1999, vol. Oct., pp. 80-85.
Dymock et al., "Novel approaches to the treatment of hepatitis C virus infection," *Antiviral Chem. Chemotherapy*, 2000, vol. 11, pp. 79-96.
Eckart et al., "The Hepatitis C Virus Encodes a Serine Protease Involved in Processing of the Putative Nonstructural Proteins from the Viral Polyprotein Precursor," *Biochem. Biophys. Res. Comm.* 1993, vol. 192, pp. 399-406.
Eldrup et al., "Structure activity relationship of 2'-modified nucleosides for inhibition of hepatitis C virus," Oral Session V, Hepatitis C Virus, Flaviviridae, 16th International Conference on Antiviral Research, Apr. 27, 2003, Savanah, GA., p. A75.
Failla et al., "Both NS3 and NS4A are required for proteolytic processing of hepatitis C virus nonstructural proteins," *J. Virol.* 1994, vol. 68, pp. 3753-3760.
Farkas et al., "Nucleic acid components and their analogues, LCIV. Synthesis of 6-amino-9-(1-deoxy-b-D-psicofuranosyl)purine," *Collect. Czech. Chem. Commun.* 1967, vol. 32, pp. 2663-2667.
Farkas et al., "Nucleic acid components and their analogues, LXXIX. Synthesis of methyl 1-deoxy-D-psicofuranosides substituted at C(1) with halo atoms or mercapto group," *Collect. Czech. Chem. Commun.* 1966, vol. 31, pp. 1535-1543.
Ferrari et al., :Characterization of Soluble Hepatitis C Virus RNA-Dependent RNA Polymerase Expressed in *Escherichia coli*, *J. Virol.* 1999, vol. 73, pp. 1649-1654.
*Field Virology*, Editors: Knippe et al., Lippincott Raven Publishers, Philadelphia PA, 1996, Chapter 31, pp. 931-956.
*Field Virology*, Fourth Edition, Editors: Knippe et al., Lippincott Raven Publishers, Philadelphia PA, 2001, p. 1001.
*Field Virology*, Fourth Edition, Editors: Knippe et al., Lippincott Raven Publishers, Philadelphia PA, 2001, Chapter 32, pp. 1014-1015.
Fukui et al., "Polynucleotides. XLIV. Synthesis and properties of poly (2-azaadenylic acid) and poly(2-azainosinic acid)," *Biochim Biophys. Acta* 1978, vol. 520, pp. 441-451.
Gagnier et al., "Synthesis and NMR studies of some imidazo[4,5-d]pyridazine nucleosides," *J. Heterocyclic Chem.* 1984, vol. 21, pp. 481-489.
Galderisi et al., "Antisense oligonucleotides as therapeutic agents," *J. Cell. Physiol.* 1999, vol. 181, pp. 251-257.
Gaudriault et al., CA 140: 386000, 2004. CAPLUS Abstract provide.
Girgis et al., "Pyrrolopyridazine nucleosides. The synthesis of certain 1-β-D-ribofuranosyl-1H-pyrrolo[2,3-d]pyridazin-4(5H)-ones," *J. Heterocyclic Chem.* 1990, vol. 27, pp. 1989-1991.
Gorbalenya et al., 'A conserved NTP-motif in putative helicases,' *Nature* 1988, vol. 333, p. 22.
Gorbalenya et al., "N-Terminal domains of putative helicases of flavi- and pestiviruses may be serine proteases," *Nucleic Acid Res.* 1989, vol. 17, pp. 3889-3897.
Grakoui et al., "A second hepatitis C virus-encoded proteinase," *Proc. Natl. Acad. Sci. USA* 1993, vol. 90, pp. 10583-10587.
Grakoui et al., "Characterization of the hepatitis C virus-encoded serine proteinase: determination of proteinase-dependent polyprotein cleavage sites," *J. Virol.* 1993, vol. 67, pp. 2832-2843.
Hall et al., "Aldehyde oxidase from rabbit liver: Specificity toward purines and their analogs," *Archives of Biochemistry and Biophysics* 1986, vol. 251, pp. 36-46.
Halstead, "Pathogenesis of dengue: challenges to molecular biology," *Science* 1988, vol. 239, pp. 476-481.
Halstead, "Selective primary health care: strategies for control of disease in the developing world. XI. Dengue," *Rev. Infect. Dis.* 1984, vol. 6, pp. 251-264.

(56) References Cited

OTHER PUBLICATIONS

Hihikata et al., "Two distinct proteinase activities required for the processing of a putative nonstructural precursor protein of hepatitis C virus," *J. Virol.* 1993, vol. 67, pp. 4665-4675.
Hong et al., "A Novel Mechanism to Ensure Terminal Initiation by Hepatitis C Virus NS5B Polymerase," *Virology* 2001, vol. 285, pp. 6-11.
Huisgen et al., "Eine neue syntheses von derivaten des pyrrols," *Chemische Berichte*, 1960, vol. 93, pp. 65-81.
Ishido et al., "Complex Formation of NS5B with NS3 and NS4A Proteins of Hepatitis C Virus," *Biochem. Biophys. Res. Commun.* 1998, vol. 244, pp. 35-40.
Ivanovics et al., "The synthesis of 2-substituted derivatives of 5-amino-1-.beta.-D-ribofuranosylimidazole-4-carboxamide. Ring opening reactions of 2-azapurine nucleosides," *J. Org. Chem.* 1974, vol. 39, pp. 3651-3654.
Jin et al., "Expression, Isolation, and Characterization of the Hepatitis C Virus ATPase/RNA Helicase," *Arch. Biochem. Biophys.* 1995, vol. 323, pp. 47-53.
Kaji et al., "Synthesis of pyridazino[4,5-e][1,3,4]thiadiazines and the ring contraction to pyrazolo[3,4-d]pyridazines through extrusion of sulfur," *Chem Pharm. Bull.* 1984, vol. 32, pp. 4437-4446.
Kaji et al., "The synthesis of pyrazolo[3,4-d]pyridazines. Photochemical cyclization to pyrazolo[3,4-d]pyridazin-4(5H)-ones with subsequent functionalization," *J. Heterocyclic Chem.* 1984, vol. 21, pp. 1249-1255.
Kakiuchi et al., "Non-peptide inhibitors of HCV serine proteinase," *FEBS Letters* 1998, vol. 421, pp. 217-220.
Kim et al., "C-Terminal domain of the hepatitis C virus NS3 protein contains an RNA helicase activity," *Biochem. Biophys. Res. Com.* 1995, vol. 215, pp. 160-166.
Kohyama et al., "A facile synthesis of AICAR from inosine," 2003, vol. 17, pp. 2639-2642.
Koonin et al., "Evolution and taxonomy of positive-strand RNA viruses: implications of comparative analysis of amino acid sequences," *Crit. Rev. Biochem. Mol. Biol.* 1993, vol. 28, pp. 375-430.
Kowana et al., "Azapurine nucleosides. 3. Synthesis of 7-(β-D-ribofuranosyl)imidazo[4,5-d]-γ-triazin-4-one (2-azainosine) and related derivatives," *J. Med. Chem.* 1972, vol. 15, pp. 841-843.
Krawczyk et al., "Synthesis of 4-substituted imidazo[4,5-d][1,2,3]triazine (2-azapurine) nucleosides," *Nucleosides, Nucleotides & Nucleic Acid* 2000, vol. 19, pp. 36-68.
Krawczyk et al., "Synthesis of 4-Substituted Imidazo[4,5-d][1,2,3]triazine (2-Azapurine)nucleosides," *Nucleosides, Nucleotides, and Nucleic Acids* 2000, vol. 19, pp. 39-68.
Kucera et al., "Novel membrane-interative ether lipid analogs that inhibit infectious HIV-1 production and induce defective virus formation," *AIDS Res. Hum. Retro Viruses* 1990, vol. 6, pp. 491-501.
Lin et al, "Hepatitis C virus NS3 serine proteinase: trans-cleavage requirements and processing kinetics" *J. Virol.* 1994, vol. 68, pp. 8147-8157.
Lohmann et al., "Biochemical and Kinetic Analyses of NS5B RNA-Dependent RNA Polymerase of the Hepatitis C Virus," *Virology* 1998, vol. 249, pp. 108-118.
Lohmann et al., "Biochemical properties of hepatitis C virus NS5B RNA-dependent RNA polymerase and identification of amino acid sequence motifs essential for enzymatic activity," *J. Virol.* 1997, vol. 71, pp. 8416-8428.
Maccjak et al., *Hepatology* 1999, vol. 30, abtract 995.
Manfred, Wolft, "Burger's Medicinal Chemistry, 5ed, Part 1," John Wiley & Sons, 1995, pp. 975-977.
Meyers et al., "Molecular characterization of pestiviruses," *Adv. Virus Res.* 1996, vol. 47, pp. 53-118.
Moennig et al., "The pestiviruses," *Adv. Virus Res.* 1992, vol. 41, pp. 53-98.
Monath, "Japanese encephalitis—a plague of the Orient," *New Eng. J. Med.* 1988, vol. 319, pp. 641-643.
Montgomery et al., "Nucleosides of 2-azapurines and certain ring analogs," *J. Med. Chem.* 1972, vol. 15, pp. 182-187.
Olsen et al., "2'-Modified nucleoside analogs as inhibitors of hepatitis C RNA replication," Oral Session V, Hepatitis C Virus, Flaviviridae, 16th International Conference on Antiviral Research, Apr. 27, 2003, Savanah, GA., p. A76.
Pace et al., "The monoethyl ester of meconic acid is an active site inhibitor of HCV NS5B RNA-dependent RNA polymerase," *Bioorg. Med. Chem. Lett.* 2004, vol. 14, pp. 3257-3261.
Qasim et al., "Interscaffolding Additivity. Association of $P_1$ Variants of Eglin c and of Turkey Ovomucoid Third Domain with Serine Proteinases," *Biochemistry*, 1997, vol. 36, pp. 1598-1607.
Raju et al., "An efficient regioselective synthesis of substituted purine analogues of guanosine and inosine," *J. Chem. Soc., Chem. Commun.* 1989, pp. 1769-1774.
Rapposelli et al., "Enantioselectivity in Cardioprotection induced by (S)-(—)-2,2-Dimethyl-N-(4'-acetamido-benzyl)-4-spiromorpholone-chromane," *J. Med. Chem.* 1993, vol. 36, pp. 3834-3842.
Sodu et al., "Establishment of an in vitro assay system for screening hepatitis C virus protease inhibitors using high performance liquid chromatography," *Antiviral Res.* 1996, vol. 32, pp. 9-18.
Sodu et al., "Novel Hepatitis C Virus Protease Inhibitors: Thiazolidine Derivatives," *Biochem. Biophys. Res. Comm.* 1997, vol. 238, pp. 643-647.
Sodu et al., *Antiviral Chem. Chemotherapy* 1998, vol. 9, p. 186.
Tatibana et al., "2-Azaadenosine triphosphate as a substitute for adenosine triphosphate in active transport of potassium across the erythrocyte membrane," *Biochim Biophys. Acta* 1963, vol. 71, pp. 464-465.
Tomei et al., "NS3 is a serine protease required for processing of hepatitis C virus polyprotein," *J. Virol.* 1993, vol. 67, pp. 4017-4026.
Tomei et al., "Biochemical characterization of a hepatitis C virus RNA-dependent RNA polymerase mutant lacking the C-terminal hydrophobic sequence," *J. Gen. Virol.* 2000, vol. 81, pp. 759-767.
Warrener et al., "Pestivirus NS3 (p80) protein possesses RNA helicase activity," *J. Virol.* 1995, vol. 69, pp. 1720-1726.
Wiskerchen et al., "Pestivirus gene expression: Protein p80 of bovine viral diarrhea virus is a proteinase involved in polyprotein processing," *Virology* 1991, vol. 184, pp. 341-350.
Xu et al., "Bovine viral diarrhea virus NS3 serine proteinase: polyprotein cleavage sites, cofactor requirements, and molecular model of an enzyme essential for pestivirus replication," *J. Virol.* 1997, vol. 71, pp. 5312-5322.
Yuan et al., "Expression, Purification, and Partial Characterization of HCV RNA Polymerase," *Biochem. Biophys. Res. Comm.* 1997, vol. 232, pp. 231-235.
Zhong et al., "Identification and Characterization of an RNA-Dependent RNA Polymerase Activity within the Nonstructural Protein 5B Region of Bovine Viral Diarrhea Virus," *J. Virol.* 1998, vol. 72, pp. 9365-9369.

\* cited by examiner (I)

or (II)

(A)

(B)

(C)

(D)

(E)

(F)

(G)

US 9,186,369 B2

PURINE NUCLEOSIDE ANALOGUES FOR TREATING FLAVIVIRIDAE INCLUDING HEPATITIS C

CROSS REFERENCE TO RELATED APPLICATIONS

This application is a divisional of U.S. application Ser. No. 12/270,795, filed Nov. 13, 2008, which is a continuation of U.S. application Ser. No. 10/900,008, filed Jul. 26, 2004, which claims the benefit of U.S. Provisional Application No. 60/490,216, filed Jul. 25, 2013, the disclosure of each of which is incorporated herein by reference in its entirety.

FIELD OF THE INVENTION

This invention is in the area of pharmaceutical chemistry, and, in particular, in the area of purine nucleosides, their syntheses, and their use as anti-Flaviviridae agents in the treatment of hosts infected with Flaviviridae and especially with Hepatitis C.

BACKGROUND OF THE INVENTION

Flaviviridae Viruses

The Flaviviridae family of viruses comprises at least three distinct genera: pestiviruses, which cause disease in cattle and pigs; flaviviruses, which are the primary cause of diseases such as dengue fever and yellow fever; and hepaciviruses such as hepatitis C (HCV). The flavivirus genus includes more than 68 members separated into groups on the basis of serological relatedness (Calisher et al., *J. Gen. Virol*, 1993, 70, 37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include Dengue virus, hemorrhagic fever viruses such as Lassa, Ebola, and yellow fever virus, shock syndrome, and Japanese encephalitis virus (Halstead, S. B., *Rev. Infect. Dis.*, 1984, 6, 251-264; Halstead, S. B., *Science*, 239:476-481, 1988; Monath, T. P., *New Eng. J. Med.*, 1988, 319, 641-643).

The pestivirus genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H.-J., *Advances in Virus Research*, 1996, 47, 53-118; Moennig V., et al, *Adv. Vir. Res.* 1992, 41, 53-98). Human pestiviruses have not been as extensively characterized as the animal pestiviruses. However, serological surveys indicate considerable pestivirus exposure in humans.

Pestiviruses and hepaciviruses are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are approximately 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS1, NS2A, NS2B, NS3, NS4A, NS4B, NS5A, and NS5B.

The NS proteins of pestiviruses and hepaciviruses share sequence domains that are characteristic of specific protein functions. For example, the NS1 glycoprotein is a cell-surface protein that is translocated into the ER lumen. NS1 was characterized initially as soluble complement-fixing antigen found in sera and tissues of infected animals, and now is known to elicit humoral immune responses in its extracellular form. Antibodies to NS1 may be used to confer passive immunity to certain pestiviruses and flaviviruses. NS1 has been implicated in the process of RNA replication where it is believed to have a functional role in the cytoplasmic processing of RNA. NS2A is a small (approximately 22 kd) protein of unknown function. Studies suggest that it binds to NS3 and NS5, and so may be a recruiter of RNA templates to membrane-bound replicase. NS2B also is a small (about 14 kd) protein that is membrane-associated, and is a required cofactor for the serine protease function of NS3, with which it forms a complex.

The NS3 proteins of viruses in both groups are large (about 70 kd), membrane-associated proteins that possess amino acid sequence motifs characteristic of serine proteinases and of helicases (Gorbalenya et al. (1988) *Nature* 333:22; Bazan and Fletterick (1989) *Virology* 171:637-639; Gorbalenya et al. (1989) *Nucleic Acid Res.* 17.3889-3897). Thus, the NS3 proteins have enzymatic activity needed for processing polyproteins for RNA replication. The C-terminal end of the NS3 proteins have an RNA triphosphotase activity that appears to modify the 5' end of the genome prior to 5'-cap addition by guanylyltransferase.

NS4A and NS4B are membrane-associated, small (about 16 kd and about 27 kd, respectively), hydrophobic proteins that appear to function in RNA replication by anchoring replicase components to cellular membranes (Fields, Virology, 4$^{th}$ Edition, 2001, p. 1001).

The NS5 proteins are the largest (about 103 kd) and most conserved, with sequence homology to other (+)-stranded RNA viruses. It also plays a pivotal role in viral replication. The NS5B proteins of pestiviruses and hepaciviruses are the enzymes necessary for synthesis of the negative-stranded RNA intermediate that is complementary to the viral genome, and of the positive-stranded RNA that is complementary to the negative-stranded RNA intermediate. The NS5B gene product has Gly-Asp-Asp (GDD) as a hallmark sequence, which it shares with reverse transcriptases and other viral polymerases and which is predictive of RNA dependent RNA polymerase (RdRP) activity (DeFrancesco et al., *Antiviral Research*, 2003, 58:1-16). Interestingly, it was found that the NS5B C-terminal 21 residue long hydrophobic tail is needed to target NS5B to the ER membrane, but its removal has no other effect and, in fact, leads to increased enzymatic solubility and activity (Tomei et al., *J. Gen. Virol.*, 2000, 81:759-767; Lohmann et al., *J. Virol.*, 1997, 71:8416-28; Ferrari et al., *J. Virol.*, 1999, 73:1649-54).

The NS5B enzyme products have the motifs characteristic of RNA-directed RNA polymerases, and in addition, share homology with methyltransferase enzymes that are involved in RNA cap formation (Koonin, E. V. and Dolja, V. V. (1993) *Crit. Rev. Biochem. Molec. Biol.* 28:375-430; Behrens et al. (1996) *EMBO J.* 15:12-22; Lchmann et al. (1997) *J. Virol.* 71:8416-8428; Yuan et al. (1997) *Biochem. Biophys. Res. Comm.* 232:231-235; Hagedorn, PCT WO 97/12033; Zhong et al. (1998) *J. Virol.* 72.9365-9369). The unliganded crystal structure of NS5B shows the unique structural feature of folding in a classic "right hand" shape, in which fingers, palm and thumb subdomains can be recognized (a feature it shares with other polymerases), but differs from other "half-open right hand" polymerases by having a more compact shapes due to two extended loops that span the finger and thumb domains at the top of the active site cavity (DeFrancesco et al. at 9). The finger, thumb and palm subdomains encircle the active site cavity to which the RNA template and NTP substrates have access via two positively charged tunnels (Bressanelli et al., *J. Virol.*, 2002, 76, 3482-92). Finger and thumb domains have strong interactions that limit their ability to change conformation independently of one another, a structural feature shared by other RdRPs. The thumb domain contains a β-hairpin loop that extends toward the cleft of the active site and may play a role in restricting the binding of the template/primer at the enzyme active site (DeFrancesco et al., at 10). Studies are in progress to determine the role of this loop in the initiation mechanism of RNA synthesis (Id.)

Nucleotidyl transfer reaction residues are located in the palm domain and contain the signature GDD motif (DeFrancesco et al., at 9). Palm domain geometry is highly conserved in all polymerases, and has a conserved two-metal-ion catalytic center that is required for catalyzing a phosphory transfer reaction at the polymerase active site.

It is believed that the de novo initiation model of RNA polymerization, rather than a "copy back" mechanism, is utilized by pesti-, flavi- and hepaciviruses. In the de novo initiation model, complementary RNA synthesis is initiated at the 3'-end of the genome by a nucleotide triphosphate rather than a nucleic acid or a protein primer. Purified NS5B is capable of this type of primer-independent action, and the C-terminal β-loop is believed to correctly position the 3'-end of the RNA template by functioning as a gate that retards slippage of the RNA 3'-end through the polymerase active site (Hong et al., *Virology*, 2001, 285:6-11. Bressanelli et al. reported the structure of NS5B polymerase in complex with nucleotides in which three distinct nucleotide-binding sites were observed in the catalytic center of the HCV RdRP, and the complex exhibited a geometry similar to the de novo initiation complex of phi 6 polymerase (Bressanelli et al., *J. Virol.*, 2002, 76: 3482-92). Thus, de novo initiation occurs and apparently is followed by RNA elongation, termination of polymerization, and release of the new strand. At each of these steps is the opportunity for intervention and inhibition of the viral lifecycle.

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett (1991) *Virology* 184:341-350; Bartenschlager et al. (1993) *J. Virol.* 67:3835-3844; Eckart et al. (1993) *Biochem. Biophys. Res. Comm.* 192:399-406; Grakoui et al. (1993) *J. Virol.* 67:2832-2843; Grakoui et al. (1993) *Proc. Natl. Acad. Sci.* USA 90:10583-10587; Hijikata et al. (1993) *J. Virol.* 67:4665-4675; Tome et al. (1993) *J. Virol.* 67:4017-4026). The NS4A protein, in both cases, acts as a cofactor with the NS3 serine protease (Bartenschlager et al. (1994) *J. Virol.* 68:5045-5055; Failla et al. (1994) *J. Virol.* 68: 3753-3760; Lin et al. (1994) 68:8147-8157; Xu et al. (1997) *J. Virol.* 71:5312-5322). The NS3 protein of both viruses also functions as a helicase (Kim et al. (1995) *Biochem. Biophys. Res. Comm.* 215: 160-166; Jin and Peterson (1995) *Arch. Biochem. Biophys.*, 323:47-53; Warrener and Collett (1995) *J. Virol.* 69:1720-1726). Finally, the NS5B proteins of pestiviruses and hepaciviruses have the predicted RNA-directed RNA polymerases activity (Behrens et al. (1996) *EMBO J.* 15:12-22; Lchmann et al. (1997) *J. Virol.* 71:8416-8428; Yuan et al. (1997) *Biochem. Biophys. Res. Comm.* 232:231-235; Hagedorn, PCT WO 97/12033; Zhong et al. (1998) *J. Virol.* 72.9365-9369).

Hepatitis C Virus

The hepatitis C virus (HCV) is the leading cause of chronic liver disease worldwide. (Boyer, N. et al. *J. Hepatol.* 32:98-112, 2000). HCV causes a slow growing viral infection and is the major cause of cirrhosis and hepatocellular carcinoma (Di Besceglie, A. M. and Bacon, B. R., *Scientific American*, October: 80-85, (1999); Boyer, N. et al. *J. Hepatol.* 32:98-112, 2000). An estimated 170 million persons are infected with HCV worldwide. (Boyer, N. et al. *J. Hepatol.* 32:98-112, 2000). Cirrhosis caused by chronic hepatitis C infection accounts for 8,000-12,000 deaths per year in the United States, and HCV infection is the leading indication for liver transplantation.

HCV is known to cause at least 80% of posttransfusion hepatitis and a substantial proportion of sporadic acute hepatitis. Preliminary evidence also implicates HCV in many cases of "idiopathic" chronic hepatitis, "cryptogenic" cirrhosis, and probably hepatocellular carcinoma unrelated to other hepatitis viruses, such as Hepatitis B Virus (HBV). A small proportion of healthy persons appear to be chronic HCV carriers, varying with geography and other epidemiological factors. The numbers may substantially exceed those for HBV, though information is still preliminary; how many of these persons have subclinical chronic liver disease is unclear. (The Merck Manual, ch. 69, p. 901, 16th ed., (1992)).

HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2.

HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides: the junction between NS2 and NS3 is autocatalytically cleaved the NS2/NS3 protease, while the remaining junctions are cleaved by the N-terminal serine protease domain of NS3 complexed with NS4A. The NS3 protein contains the NTP-dependent helicase activity that unwinds duplex RNA during replication. The hydrophobic carboxy-terminal 21 amino acids of nonstructural protein 5, NS5B, contains the RNA-dependent RNA polymerase that is essential for viral replication (*Fields Virology*, Fourth Edition, Editors: Fields, B. N., Knipe, D. M., and Howley, P. M., Lippincott-Raven Publishers, Philadelphia, Pa., 2001, Chapter 32, pp. 1014-1015). NS5B is known to bind RNAs non-specifically, and to interact directly with NS3 and NS4A that, in turn, form complexes with NS4B and NS5A (Id @ 1015; Ishido et al., *Biochem. Biophys. Res. Commun.*, 1998; 244: 35-40). Certain in vitro experiments using NS5B and guanosine 5'-mono-, di-, and triphosphate as well as 5'-triphosphate of 2'-deoxy- and 2',3'-dideoxy-guanosine as HCV inhibitors suggest that HCV-RdRP may have a strict specificity for 5'-triphosphates and 2'- and 3'-OH groups (Watanabe et al., U.S. 2002/0055483). Otherwise, the function(s) of the remaining nonstructural proteins, NS4A, NS4B, and NS5A (the amino-terminal half of nonstructural protein 5) remain unknown.

A significant focus of current antiviral research is directed to the development of improved methods of treatment of chronic HCV infections in humans (Di Besceglie, A. M. and Bacon, B. R., *Scientific American*, October: 80-85, (1999)). Methods to Treat Flaviviridae Infections The development of new antiviral agents for Flaviviridae infections, especially hepatitis C, is currently underway. Specific inhibitors of HCV-derived enzymes such as protease, helicase, and polymerase inhibitors are being developed. Drugs that inhibit other steps in HCV replication are also in development, for example, drugs that block production of HCV antigens from the RNA (IRES inhibitors), drugs that prevent the normal processing of HCV proteins (inhibitors of glycosylation), drugs that block entry of HCV into cells (by blocking its receptor) and nonspecific cytoprotective agents that block cell injury caused by the virus infection. Further, molecular approaches are also being developed to treat hepatitis C, for example, ribozymes, which are enzymes that break down specific viral RNA molecules, and antisense oligonucleotides, which are small complementary segments of DNA that bind to viral RNA and inhibit viral replication, are under investigation. A number of HCV treatments are reviewed by Bymock et al. in *Antiviral Chemistry & Chemotherapy*, 11:2; 79-95 (2000) and De Francesco et al. in *Antiviral Research*, 58: 1-16 (2003).

Idenix Pharmaceuticals, Ltd. discloses branched nucleosides, and their use in the treatment of HCV and flaviviruses and pestiviruses in US Patent Publication Nos. 2003/0050229 A1, 2004/0097461 A1, 2004/0101535 A1, 2003/0060400 A1, 2004/0102414 A1, 2004/0097462 A1, and 2004/0063622 A1 which correspond to International Publication Nos. WO 01/90121 and WO 01/92282. A method for the treatment of hepatitis C infection (and flaviviruses and pestiviruses) in humans and other host animals is disclosed in the Idenix publications that includes administering an effective amount of a biologically active 1', 2', 3' or 4'-branched β-D or β-L nucleosides or a pharmaceutically acceptable salt or prodrug thereof, administered either alone or in combination, optionally in a pharmaceutically acceptable carrier. See also U.S. Patent Publication Nos. 2004/0006002 and 2004/0006007 as well as WO 03/026589 and WO 03/026675. Idenix Pharmaceuticals, Ltd. also discloses in US Patent Publication No. 2004/0077587 pharmaceutically acceptable branched nucleoside prodrugs, and their use in the treatment of HCV and flaviviruses and pestiviruses in prodrugs. See also PCT Publication Nos. WO 04/002422, WO 04/002999, and WO 04/003000. Further, Idenix Pharmaceuticals, Ltd. also discloses in WO 04/046331 Flaviviridae mutations caused by biologically active 2'-branched β-D or β-L nucleosides or a pharmaceutically acceptable salt or prodrug thereof.

Biota Inc. discloses various phosphate derivatives of nucleosides, including 1', 2', 3' or 4'-branched β-D or β-L nucleosides, for the treatment of hepatitis C infection in International Patent Publication WO 03/072757.

Emory University and the University of Georgia Research Foundation, Inc. (UGARF) discloses the use of 2'-fluoro-nucleosides for the treatment of HCV in U.S. Pat. No. 6,348,587. See also US Patent Publication No. 2002/0198171 and International Patent Publication WO 99/43691.

BioChem Pharma Inc. (now Shire Biochem, Inc.) discloses the use of various 1,3-dioxolane nucleosides for the treatment of a Flaviviridae infection in U.S. Pat. No. 6,566,365. See also U.S. Pat. Nos. 6,340,690 and 6,605,614; US Patent Publication Nos. 2002/0099072 and 2003/0225037, as well as International Publication No. WO 01/32153 and WO 00/50424.

BioChem Pharma Inc. (now Shire Biochem, Inc.) also discloses various other 2'-halo, 2'-hydroxy and 2'-alkoxy nucleosides for the treatment of a Flaviviridae infection in US Patent Publication No. 2002/0019363 as well as International Publication No. WO 01/60315 (PCT/CA01/00197; filed Feb. 19, 2001).

ICN Pharmaceuticals, Inc. discloses various nucleoside analogs that are useful in modulating immune response in U.S. Pat. Nos. 6,495,677 and 6,573,248. See also WO 98/16184, WO 01/68663, and WO 02/03997.

U.S. Pat. No. 6,660,721; US Patent Publication Nos. 2003/083307 A1, 2003/008841 A1, and 2004/0110718; as well as International Patent Publication Nos. WO 02/18404; WO 02/100415, WO 02/094289, and WO 04/043159; filed by F. Hoffmann-La Roche AG, discloses various nucleoside analogs for the treatment of HCV RNA replication.

Pharmasset Limited discloses various nucleosides and antimetabolites for the treatment of a variety of viruses, including Flaviviridae, and in particular HCV, in US Patent Publication Nos. 2003/0087873, 2004/0067877, 2004/0082574, 2004/0067877, 2004/002479, 200310225029, and 2002/00555483, as well as International Patent Publication Nos. WO 02/32920, WO 01/79246, WO 0248165, WO 03/068162, WO 03/068164 and WO 2004/013298.

Merck & Co., Inc. and Isis Pharmaceuticals disclose in US Patent Publication No. 2002/0147160, 2004/0072788, 2004/0067901, and 2004/0110717; as well as the corresponding International Patent Publication Nos. WO 02/057425 (PCT/US02/01531; filed Jan. 18, 2002) and WO 02/057287 (PCT/US02/03086; filed Jan. 18, 2002) various nucleosides, and in particular several pyrrolopyrimidine nucleosides, for the treatment of viruses whose replication is dependent upon RNA-dependent RNA polymerase, including Flaviviridae, and in particular HCV. See also WO 2004/000858, WO 2004/003138, WO 2004/007512, and WO 2004/009020.

US Patent Publication No. 2003/028013 A1 as well as International Patent Publication Nos. WO 03/051899, WO 03/061576, WO 03/062255 WO 03/062256, WO 03/062257, and WO 03/061385, filed by Ribapharm, also are directed to the use of certain nucleoside analogs to treat hepatitis C virus.

Genelabs Technologies disclose in US Patent Publication No. 2004/0063658 as well as International Patent Publication Nos. WO 03/093290 and WO 04/028481 various base modified derivatives of nucleosides, including 1', 2', 3' or 4'-branched β-D or β-L nucleosides, for the treatment of hepatitis C infection.

Eldrup et al. (Oral Session V, Hepatitis C Virus, Flaviviridae; 16th International Conference on Antiviral Research (Apr. 27, 2003, Savannah, Ga.) p. A75) described the structure activity relationship of 2'-modified nucleosides for inhibition of HCV.

Bhat et al (Oral Session V, Hepatitis C Virus, Flaviviridae; 16th International Conference on Antiviral Research (Apr. 27, 2003, Savannah, Ga.); p A75) describe the synthesis and pharmacokinetic properties of nucleoside analogues as possible inhibitors of HCV RNA replication. The authors report that 2'-modified nucleosides demonstrate potent inhibitory activity in cell-based replicon assays.

Olsen et al. (Oral Session V, Hepatitis C Virus, Flaviviridae; 16th International Conference on Antiviral Research (Apr. 27, 2003, Savannah, Ga.) p A76) also described the effects of the 2'-modified nucleosides on HCV RNA replication.

Drug-resistant variants of viruses can emerge after prolonged treatment with an antiviral agent. Drug resistance most typically occurs by mutation of a gene that encodes for an enzyme used in viral replication, and, for example, in the case of HIV, reverse transcriptase, protease, or DNA polymerase. It has been demonstrated that the efficacy of a drug against viral infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous pressures on the virus. One cannot predict, however, what mutations will be induced in the viral genome by a given drug, whether the mutation is permanent or transient, or how an infected cell with a mutated viral sequence will respond to therapy with other agents in combination or alternation. This is exacerbated by the fact that there is a paucity of data on the kinetics of drug resistance in long-term cell cultures treated with modern antiviral agents.

In view of the severity of diseases associated with pestiviruses, flaviviruses, and hepatitis C virus, and their pervasiveness in animals and humans, it is an object of the present invention to provide a compound, method and composition for the treatment of a host infected with any member of the family Flaviviridae, including hepatitis C virus.

Further, it is an object of the present invention to provide a compound, method and pharmaceutically-acceptable composition for the prophylaxis and/or treatment of a host, and particularly a human, infected with any member of the family Flaviviridae.

Further, given the rising threat of other Flaviviridae infections, there remains a strong need to provide new effective pharmaceutical agents that have low toxicity to the host.

Therefore, it is an object of the present invention to provide a compound, method and composition for the treatment of a host infected with any member of the family Flaviviridae, including hepatitis C virus, that have low toxicity to the host.

It is another object of the present invention to provide a compound, method and composition generally for the treatment of patients infected with pestiviruses, flaviviruses, or hepaciviruses.

SUMMARY OF THE INVENTION

Methods and compositions for the treatment of pestivirus, flavivirus and hepatitis C virus infection are described that include administering an effective amount of a beta-D or beta-L-nucleoside of the Formulae (I) and (II), or a pharmaceutically acceptable salt or prodrug thereof.

In a first principal embodiment, a compound of the Formula (I), or a pharmaceutically acceptable salt or prodrug thereof, is provided:

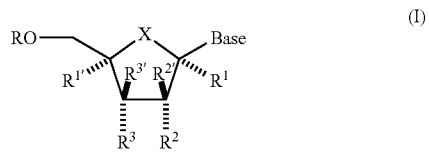

wherein
each R is independently H, phosphate (including mono-, di-, or triphosphate or a stabilized phosphate prodrug) or phosphonate; optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), lipid, phospholipid, carbohydrate, peptide, cholesterol, an amino acid residue or derivative, or other pharmaceutically acceptable leaving group that is capable of providing H or phosphate when administered in vivo;

n is 0-2;

when X is $CH_2$, CHOH, CH-alkyl, CH-alkenyl, CH-alkynyl, C-dialkyl, CH—O-alkyl, CH—O-alkenyl, CH—O-alkynyl, CH—S-alkyl, CH—S-alkenyl, CH—S-alkynyl, CH-halogen, or C-(halogen)$_2$, then each $R^1$ and $R^{1'}$ is independently H, OH, optionally substituted alkyl including lower alkyl, azido, cyano, optionally substituted alkenyl or alkynyl, —C(O)O-(alkyl), —C(O)O(lower alkyl), —C(O)O-(alkenyl), —C(O)O-(alkynyl), —O(acyl), —O(lower acyl), —O(alkyl), —O(lower alkyl), —O(alkenyl), —O(alkynyl), halogen, halogenated alkyl, —$NO_2$, —$NH_2$, —NH(lower alkyl), —N(lower alkyl)$_2$, —NH(acyl), —N(acyl)$_2$, —C(O)$NH_2$, —C(O)NH(alkyl), —C(O)N(alkyl)$_2$, S(O)N-alkyl, S(O)N-alkenyl, S(O)N-alkynyl, or SCH-halogen, wherein alkyl, alkenyl, and/or alkynyl may optionally be substituted;

when X is O, S[O]$_n$, NH, N-alkyl, N-alkenyl, N-alkynyl, S(O)N-alkyl, S(O)N-alkenyl, S(O)N-alkynyl, or SCH-halogen, then each $R^1$ and $R^{1'}$ is independently H, optionally substituted alkyl including lower alkyl, azido, cyano, optionally substituted alkenyl or alkynyl, —C(O)O-(alkyl), —C(O)O (lower alkyl), —C(O)O-(alkenyl), —C(O)O-(alkynyl), halogenated alkyl, —C(O)$NH_2$, —C(O)NH(alkyl), —C(O)N(alkyl)$_2$, —C(H)═N—$NH_2$, C(S)$NH_2$, C(S)NH (alkyl), or C(S)N(alkyl)$_2$, wherein alkyl, alkenyl, and/or alkynyl may optionally be substituted;

each $R^2$ and $R^3$ is independently H, OH, $NH_2$, SH, F, Cl, Br, I, CN, $NO_2$, —C(O)$NH_2$, —C(O)NH(alkyl), and —C(O) N(alkyl)$_2$, $N_3$, optionally substituted alkyl including lower alkyl, optionally substituted alkenyl or alkynyl, halogenated alkyl, —C(O)O-(alkyl), —C(O)O(lower alkyl), —C(O)O-(alkenyl), —C(O)O-(alkynyl), —O(acyl), —O(alkyl), —)(alkenyl), —O(alkynyl), —OC(O)$NH_2$, NC, C(O)OH, SCN, OCN, —S(alkyl), —S(alkenyl), —S(alkynyl), —NH(alkyl), —N(alkyl)$_2$, —NH(alkenyl), —NH(alkynyl), an amino acid residue or derivative, a prodrug or leaving group that provides OH in vivo, or an optionally substituted 3-7 membered heterocyclic ring having O, S and/or N independently as a heteroatom taken alone or in combination;

each R$^{2'}$ and R$^{3'}$ is independently H; optionally substituted alkyl, alkenyl, or alkynyl; —C(O)O(alkyl), —C(O)O(lower alkyl), —C(O)O(alkenyl), —C(O)O(alkynyl), —C(O)NH$_2$, —C(O)NH(alkyl), —C(O)N(alkyl)$_2$, —O(acyl), —O(lower acyl), —O(alkyl), —O(lower alkyl), —O(alkenyl), halogen, halogenated alkyl and particularly CF$_3$, azido, cyano, NO$_2$, —S(alkyl), —S(alkenyl), —S(alkynyl), NH$_2$, —NH(alkyl), —N(alkyl)$_2$, —NH(alkenyl), —NH(alkynyl), —NH(acyl), or —N(acyl)$_2$, and R$_3$ at 3'-C may also be OH; and Base is selected from the group consisting of:

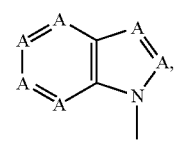

(A)

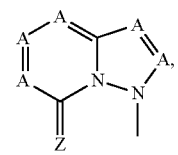

(B)

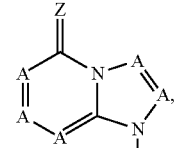

(C)

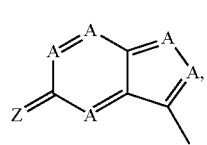

(D)

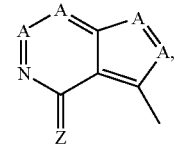

(E)

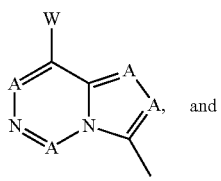

(F)

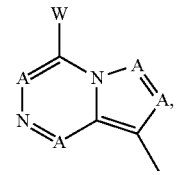 and (G)

wherein:

each A independently is N or C—R$^5$;

each W is H, OH, —O(acyl), —O(C$_{1-4}$ alkyl), —O(alkenyl), —O(alkynyl), —OC(O)R$^4$R$^4$, —OC(O)NR$^4$R$^4$, SH, —S(acyl), —S(C$_{1-4}$ alkyl), NH$_2$, NH(acyl), N(acyl)$_2$, NH(C$_{1-4}$ alkyl), N(C$_{1-4}$ alkyl)$_2$, —N(cycloalkyl)C$_{1-4}$ alkylamino, di(C$_{1-4}$ alkyl)amino, C$_{3-6}$ cycloalkylamino, halogen, C$_{1-4}$ alkyl, C$_{1-4}$ alkoxy, CN, SCN, OCN, SH, N$_3$, NO$_2$, NH=NH$_2$, N$_3$, NHOH, —C(O)NH$_2$, —C(O)NH(acyl), —C(O)N(acyl)$_2$, —C(O)NH(C$_{1-4}$ alkyl), —C(O)N(C$_{1-4}$ alkyl)$_2$, —C(O)N(alkyl)(acyl), or halogenated alkyl;

each Z is O, S, NH, N—OH, N—NH$_2$, NH(alkyl), N(alkyl)$_2$, N-cycloalkyl, alkoxy, CN, SCN, OCN, SH, NO$_2$, NH$_2$, N$_3$, NH=NH, NH(alkyl), N(alkyl)$_2$, CONH$_2$, CONH(alkyl), or CON(alkyl)$_2$;

each R$^4$ is independently H, acyl, or C$_{1-6}$ alkyl;

each R$^5$ is independently H, Cl, Br, F, I, CN, OH, optionally substituted alkyl, alkenyl or alkynyl, carboxy, C(=NH)NH$_2$, C$_{1-4}$ alkoxy, C$_{1-4}$ alkyloxycarbonyl, N$_3$, NH$_2$, NH(alkyl), N(alkyl)$_2$, NO$_2$, N$_3$, halogenated alkyl especially CF$_3$, C$_{1-4}$ alkylamino, di(C$_{1-4}$ alkyl)amino, C$_{3-6}$ cycloalkylamino, C$_{1-6}$ alkoxy, SH, —S(C$_{1-4}$ alkyl), —S(C$_{1-4}$ alkenyl), —S(C$_{1-4}$ alkynyl), C$_{1-6}$ alkylthio, C$_{1-6}$ alkylsulfonyl, (C$_{1-4}$ alkyl)$_{0-2}$ aminomethyl, C$_{3-6}$ cycloalkylamino-alkenyl, -alkynyl, —(O)alkyl, —(O)alkenyl, —(O)alkynyl, —(O)acyl, —O(C$_{1-4}$ alkyl), —O(C$_{1-4}$ alkenyl), —O(C$_{1-4}$ alkynyl), —O—C(O)NH$_2$, —OC(O)N(alkyl), —OC(O)R'R", —C(O)OH, C(O)O-alkyl, C(O)O-alkenyl, C(O)O-alkynyl, S-alkyl, S-acyl, S-alkenyl, S-alkynyl, SCN, OCN, NC, —C(O)—NH$_2$, C(O)NH(alkyl), C(O)N(alkyl)$_2$, C(O)NH(acyl), C(O)N(acyl)$_2$, (S)—NH$_2$, NH-alkyl, N(dialkyl)$_2$, NH-acyl, N-diacyl, or a 3-7 membered heterocycle having O, S, or N taken independently in any combination;

each R' and R" independently is H, C$_{1-6}$ alkyl, C$_{2-6}$ alkenyl, C$_{2-6}$ alkynyl, halogen, halogenated alkyl, OH, CN, N$_3$, carboxy, C$_{1-4}$ alkoxycarbonyl, NH$_2$, C$_{1-4}$ alkylamino, di(C$_{1-4}$ alkyl)amino, C$_{1-6}$ alkoxy, C$_{1-6}$ alkylsulfonyl, or (C$_{1-4}$ alkyl)$_{0-2}$ aminomethyl; and all tautomeric, enantiomeric and stereoisomeric forms thereof;

with the caveat that when X is S in Formula (I), then the compound is not 5-(4-amino-imidazo[4,5-d][1,2,3]triazin-7-yl)-2-hydroxymethyl-tetrahydro-thiophen-3-ol or 7-(4-hydroxy-5-hydroxy-methyl-tetrahydro-thiophen-2-yl)-3,7-dihydro-imidazo[4,5-d][1,2,3]triazin-4-one.

In a second principal embodiment, a compound of the Formula (II), or a pharmaceutically acceptable salt or prodrug thereof, is provided:

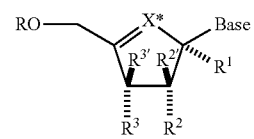

(II)

wherein:

R, R$^2$, R$^{2'}$, R$^3$, and R$^{3'}$ are all as defined above;

X* is CY$^3$;

Y$^3$ is hydrogen, alkyl, bromo, chloro, fluoro, iodo, azido, cyano, alkenyl, alkynyl, —C(O)O(alkyl), —C(O)O(lower alkyl), CF$_3$, —CONH$_2$, —CONH(alkyl), or —CON(alkyl)$_2$;

R$^1$ is H, OH, optionally substituted alkyl including lower alkyl, azido, cyano, optionally substituted alkenyl or alkynyl, —C(O)O-(alkyl), —C(O)O(lower alkyl), —C(O)O-(alkenyl), —C(O)O-(alkynyl), —O(acyl), —O(lower acyl), —O(alkyl), —O(lower alkyl), —O(alkenyl), —S(alkynyl), halogen, halogenated alkyl, —NO$_2$, —NH$_2$, —NH(lower alkyl), —N(lower alkyl)$_2$, —NH(acyl), —N(acyl)$_2$, —C(O)NH$_2$, —C(O)NH(alkyl), or —C(O)N (alkyl)$_2$, wherein an optional substitution on alkyl, alkenyl, and/or alkynyl may be one or more halogen, hydroxy, alkoxy or alkylthio groups taken in any combination;

Base is defined as above for formulae (A)-(G); and all tautomeric, enantiomeric and stereoisomeric forms thereof;

with the caveat that when X is S in Formula (I), then the compound is not 5-(4-amino-imidazo[4,5-d][1,2,3]triazin-7-yl)-2-hydroxymethyl-tetrahydro-thiophen-3-ol or 7-(4-hydroxy-5-hydroxy-methyl-tetrahydro-thiophen-2-yl)-3,7-dihydro-imidazo[4,5-d][1,2,3]triazin-4-one.

In preferred embodiments, Bases (A)-(G) have a structure selected from the group consisting of:

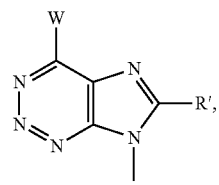
(i)

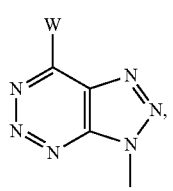
(ii)

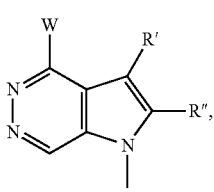
(iii)

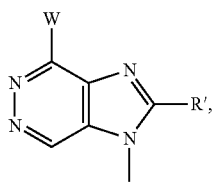
(iv)

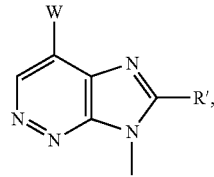
(v)

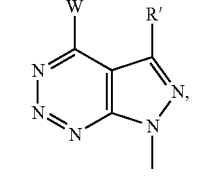
(vi)

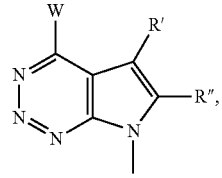
(vii)

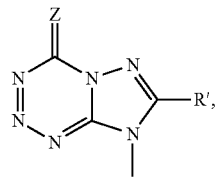
(viii)

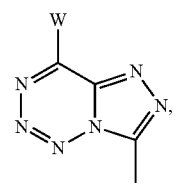
(ix)

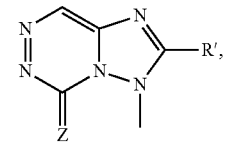
(x)

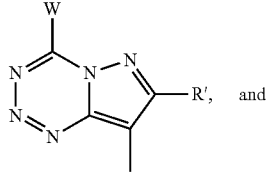
(xi) and

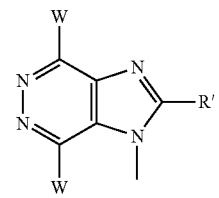
(xii)

wherein each R' and R" independently is H, C$_{1-6}$ alkyl, C$_{2-6}$ alkenyl, C$_{2-6}$ alkynyl, halogen, halogenated alkyl, OH, CN, N$_3$, carboxy, C$_{1-4}$ alkoxycarbonyl, NH$_2$, C$_{1-4}$ alkylamino, di(C$_{1-4}$ alkyl)amino, C$_{1-6}$ alkoxy, C$_{1-6}$ alkylsulfonyl, (C$_{1-4}$ alkyl)$_{0-2}$ aminomethyl, as provided above in the definitions of A and Z for the Base Formulae (A)-(G);

each W is independently H, Cl, Br, I, F, halogenated alkyl, alkoxy, OH, SH, O-alkyl, S-alkyl, O-alkenyl, O-alkynyl, S-alkenyl, S-alkynyl, —OC(O)NR$^4$R$_4$, O-acyl, S-acyl, CN, SCN, OCN, NO$_2$, N$_3$, NH$_2$, NH(alkyl), N(alkyl)$_2$, NH-cycloalkyl, NH-acyl, NH=NH, CONH$_2$, CONH(alkyl), or CON(alkyl)$_2$; and each R$^4$ is independently H, acyl, or C$_{1-6}$ alkyl;

each Z is O, S, NH, N—OH, N—NH$_2$, NH(alkyl), N(alkyl)$_2$, N-cycloalkyl, alkoxy, CN, SCN, OCN, SH, NO$_2$, NH$_2$, N$_3$, NH=NH, NH(alkyl), N(alkyl)$_2$, CONH$_2$, CONH(alkyl), or CON(alkyl)$_2$.

In its preferred embodiments, the compounds of the present invention comprise nucleosides in which each variable in Formula (I) is selected from the following, in any combination: X is O or S; R is H or phosphate; $R_1$ is H, $CH_2OH$, or $CONH_2$; $R_2$ is OH or F; $R_3$ is alkyl, especially methyl or propynyl, or H at the 3' position; A is H, CH or N; Z is O, S, or NH; W is $NH_2$, Cl, OMe, OH, NH-cyclopropyl, S-Me; and each R' and R" independently is Cl, CN, $CONH_2$ or Me.

In its preferred embodiments for Formula (II), the compounds of the present invention comprise nucleosides in which each variable in Formula (II) is selected from the following, in any combination: X* is CH; R is H or phosphate; $R_1$ is H, $CH_2OH$, or $CONH_2$; $R_2$ is OH or F; $R_3$ is alkyl, especially methyl or propynyl, or H at the 3' position; A is H, CH or N; Z is O, S, or NH; W is $NH_2$, Cl, OMe, OH, NH-cyclopropyl, S-Me; and each R' and R" independently is Cl, CN, $CONH_2$ or Me.

In all embodiments, optional substituents are selected from the group consisting of one or more halogen, amino, hydroxy, carboxy and alkoxy groups or atoms, among others. It is to be understood that all stereoisomeric and tautomeric forms of the compounds shown are included herein.

The active compounds of the present invention can be administered in combination, alternation or sequential steps with another anti-HCV agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

DETAILED DESCRIPTION OF THE INVENTION

Figure 1:
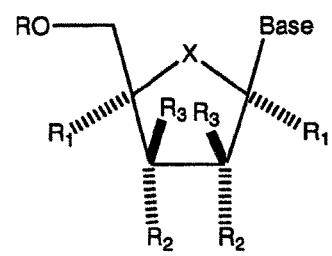
FIG. 1 show generalized structural depictions for Formula (I) and Formula (II) of the ribofuranosylnucleosides of the present invention.
Figure 1:
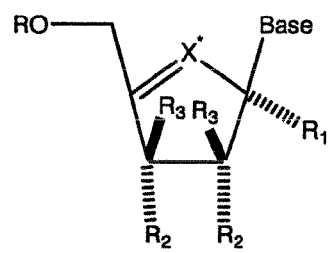
Figure 2:
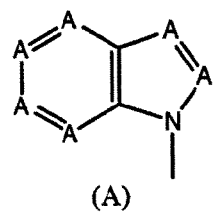
FIG. 2 shows generalized structures for the 2-azapurine bases of the present invention.
Figure 2:
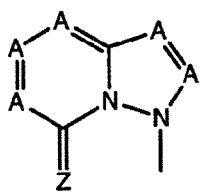
Figure 2:
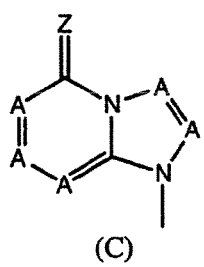
Figure 2:
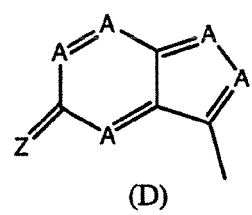
Figure 2:
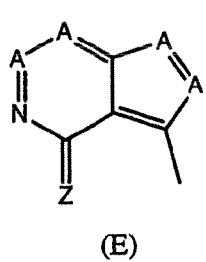
Figure 2:
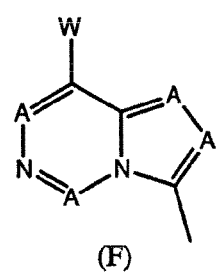
Figure 2:
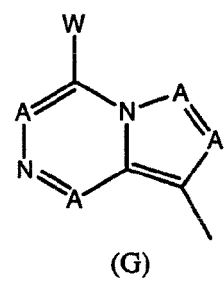
Figure 3:
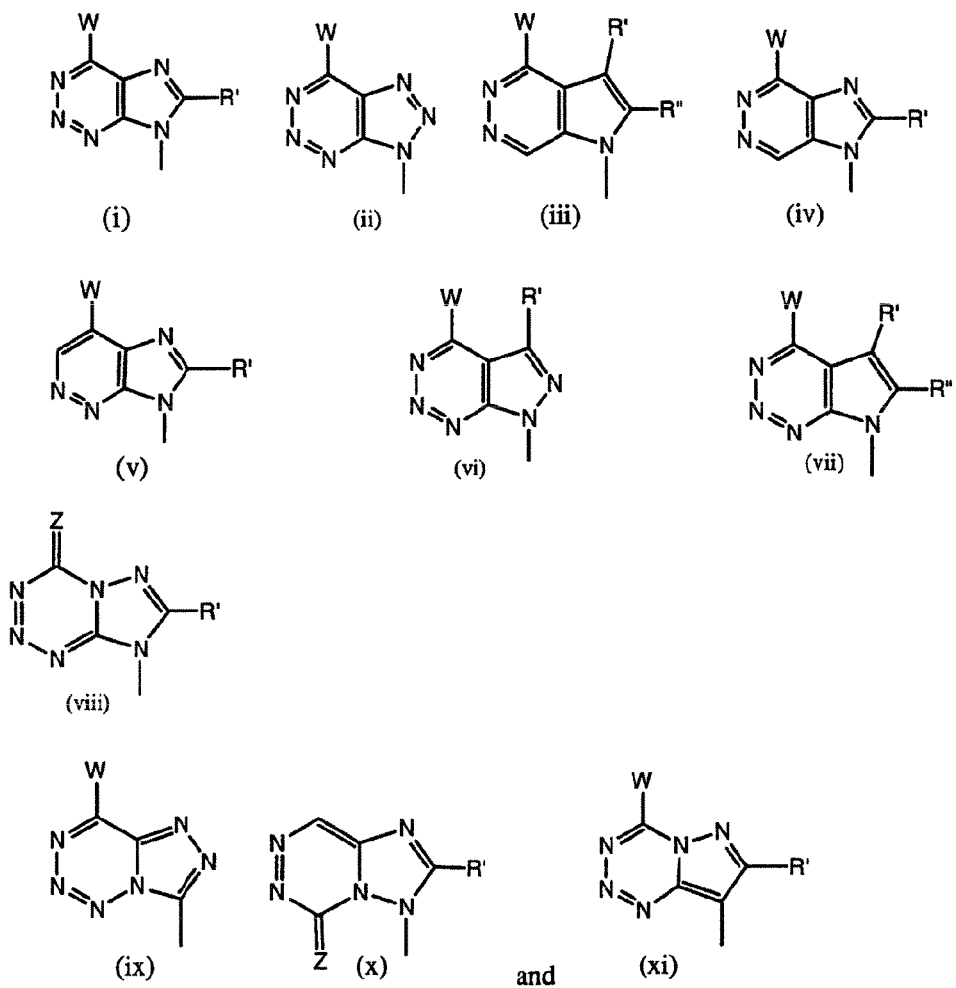
FIG. 3 shows structural depictions for preferred bases of the present invention.

The present invention provides a compound, method and composition for the treatment of a pestivirus, flavivirus and/or hepatitis C in humans or other host animals that includes administering an effective anti-pestivirus, anti-flavivirus or anti-HCV treatment amount of a beta-D- or beta-L-nucleoside as described herein, or a pharmaceutically acceptable salt or prodrug thereof, optionally in a pharmaceutically acceptable carrier. The compounds of this invention either possess antiviral activity, or are metabolized to a compound that exhibits such activity.

Flaviviruses included within the scope of this invention are discussed generally in *Fields Virology*, Editors: Fields, N., Knipe, D. M. and Howley, P. M.; Lippincott-Raven Publishers, Philadelphia, Pa.; Chapter 31 (1996). Specific flaviviruses include, without limitation: Absettarov; Alfuy; Apoi; Aroa; Bagaza; Banzi; Bououi; Bussuquara; Cacipacore; Carey Island; Dakar bat; Dengue viruses 1, 2, 3 and 4; Edge Hill; Entebbe bat; Gadgets Gully; Hanzalova; Hypr; Ilheus; Israel turkey meningoencephalitis; Japanese encephalitis; Jugra; Jutiapa; Kadam; Karshi; Kedougou; Kokoera; Koutango; Kumlinge; Kunjin; Kyasanur Forest disease; Langat; Louping ill; Meaban; Modoc; Montana myotis leukoencephalitis; Murray valley encephalitis; Naranjal; Negishi; Ntaya; Omsk hemorrhagic fever; Phnom-Penh bat; Powassan; Rio Bravo; Rocio; Royal Farm; Russian spring-summer encephalitis; Saboya; St. Louis encephalitis; Sal Vieja; San Perlita; Saumarez Reef; Sepik; Sokuluk; Spondweni; Stratford; Temusu; Tyuleniy; Uganda S, Usutu, Wesselsbron; West Nile; Yaounde; Yellow fever; and Zika.

Pestiviruses included within the scope of this invention are also discussed generally in *Fields Virology* (Id). Specific pestiviruses include, without limitation: bovine viral diarrhea virus ("VDV"); classical swine fever virus ("CSFV") also known as hog cholera virus); and border disease virus ("DV").

HCV is a member of the family, Flaviviridae; however, HCV now has been placed in a new monotypic genus, hepacivirus.

Active Compounds, Pharmaceutically Acceptable Salts and Prodrugs Thereof

In a first principal embodiment, a compound of the Formula (I), or a pharmaceutically acceptable salt or prodrug thereof, is provided:

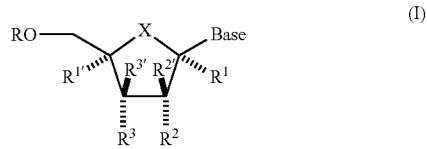

(I)

wherein

R is H, phosphate (including mono-, di-, or triphosphate or a stabilized phosphate prodrug) or phosphonate; optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), lipid, phospholipid, carbohydrate, peptide, cholesterol, an amino acid residue or derivative, or other pharmaceutically acceptable leaving group that is capable of providing H or phosphate when administered in vivo;

n is 0-2;

when X is $CH_2$, CHOH, CH-alkyl, CH-alkenyl, CH-alkynyl, C-dialkyl, CH—O-alkyl, CH—O-alkenyl, CH—O-alkynyl, CH—S-alkyl, CH—S-alkenyl, CH—S-alkynyl, CH-halogen, or C-(halogen)$_2$, then each $R^1$ and $R^{1'}$ is independently H, OH, optionally substituted alkyl including lower alkyl, azido, cyano, optionally substituted alkenyl or alkynyl, —C(O)O-(alkyl), —C(O)O(lower alkyl), —C(O)O-(alkenyl), —C(O)O-(alkynyl), —O(acyl), —O(lower acyl), —O(alkyl), —O(lower alkyl), —O(alkenyl), —O(alkynyl), halogen, halogenated alkyl, —$NO_2$, —$NH_2$, —NH(lower alkyl), —N(lower alkyl)$_2$, —NH(acyl), —N(acyl)$_2$, —C(O)$NH_2$, —C(O)NH(alkyl), —C(O)N(alkyl)$_2$, S(O)N-alkyl, S(O)N-alkenyl, S(O)N-alkynyl, or SCH-halogen, wherein alkyl, alkenyl, and/or alkynyl may optionally be substituted;

when X is O, S[O]$_n$, NH, N-alkyl, N-alkenyl, N-alkynyl, S(O)N-alkyl, S(O)N-alkenyl, S(O)N-alkynyl, or SCH-halogen, then each $R^1$ and $R^{1'}$ is independently H, optionally substituted alkyl including lower alkyl, azido, cyano, optionally substituted alkenyl or alkynyl, —C(O)O-(alkyl), —C(O)O (lower alkyl), —C(O)O-(alkenyl), —C(O)O-(alkynyl), halogenated alkyl, —C(O)NH₂, —C(O)NH(alkyl), —C(O)N(alkyl)₂, —C(H)=N—NH₂, C(S)NH₂, C(S)NH(alkyl), or C(S)N(alkyl)₂, wherein alkyl, alkenyl, and/or alkynyl may optionally be substituted;

each $R^2$ and $R^3$ is independently is OH, NH₂, SH, F, Cl, Br, I, CN, NO₂, —C(O)NH₂, —C(O)NH(alkyl), —C(O)N(alkyl)₂, N₃, optionally substituted alkyl including lower alkyl, optionally substituted alkenyl or alkynyl, halogenated alkyl, —C(O)O-(alkyl), —C(O)O(lower alkyl), —C(O)O-(alkenyl), —C(O)O-(alkynyl), —O(acyl), —O(alkyl), —O(alkenyl), —O(alkynyl), —OC(O)NH₂, NC, C(O)OH, SCN, OCN, —S(alkyl), —S(alkenyl), —S(alkynyl), —NH(alkyl), —N(alkyl)₂, —NH(alkenyl), —NH(alkynyl), an amino acid residue or derivative, a prodrug or leaving group that provides OH in vivo, or an optionally substituted 3-7 membered heterocyclic ring having O, S and/or N independently as a heteroatom taken alone or in combination;

each $R^{2'}$ and $R^{3'}$ independently is H; optionally substituted alkyl, alkenyl, or alkynyl; —C(O)O(alkyl), —C(O)O(lower alkyl), —C(O)O(alkenyl), —C(O)O(alkynyl), —C(O)NH₂, —C(O)NH(alkyl), —C(O)N(alkyl)₂, —), —O(lower acyl), —O(alkyl), —O(lower alkyl), —O(alkenyl), halogen, halogenated alkyl and particularly CF₃, azido, cyano, NO₂, —S(alkyl), —S(alkenyl), —S(alkynyl), NH₂, —NH(alkyl), —N(alkyl)₂, —NH(alkenyl), —NH(alkynyl), —NH(acyl), or —N(acyl)₂, and $R_3$ at 3'-C may also be OH; and Base is selected from the group consisting of:

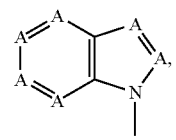
(A)

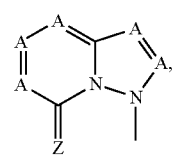
(B)

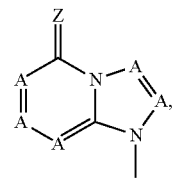
(C)

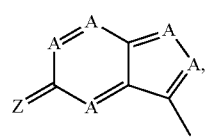
(D)

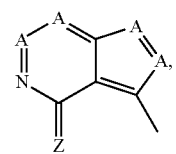
(E)

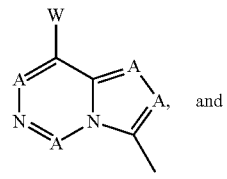
(F)
and

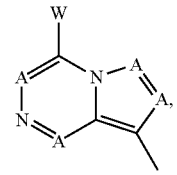
(G)

wherein
each A independently is N or C—$R^5$;
W is H, OH, —O(acyl), —O(C₁₋₄ alkyl), —O(alkenyl), —O(alkynyl), —OC(O)R⁴R⁴, —OC(O)NR⁴R⁴, SH, —), —S(C₁₋₄ alkyl), NH₂, NH(acyl), N(acyl)₂, NH(C₁₋₄ alkyl), N(C₁₋₄ alkyl)₂, —N(cycloalkyl) C₁₋₄ alkylamino, di(C₁₋₄ alkyl)amino, C₃₋₆ cycloalkylamino, halogen, C₁₋₄ alkyl, C₁₋₄ alkoxy, CN, SCN, OCN, SH, N₃, NO₂, NH=NH₂, N₃, NHOH, —C(O)NH₂, —C(O)NH(acyl), —C(O)N(acyl)₂, —C(O)NH(C₁₋₄ alkyl), —C(O)N(C₁₋₄ alkyl)₂, —C(O)N(alkyl)(acyl), or halogenated alkyl;
Z is O, S, NH, N—OH, N—NH₂, NH(alkyl), N(alkyl)₂, N-cycloalkyl, alkoxy, CN, SCN, OCN, SH, NO₂, NH₂, N₃, NH=NH, NH(alkyl), N(alkyl)₂, CONH₂, CONH(alkyl), or CON(alkyl)₂;
each $R^4$ is independently H, acyl, or C₁₋₆ alkyl;
each $R^5$ is independently H, Cl, Br, F, I, CN, OH, optionally substituted alkyl, alkenyl or alkynyl, carboxy, C(=NH)NH₂, C₁₋₄ alkoxy, C₁₋₄ alkyloxycarbonyl, N₃, NH₂, NH(alkyl), N(alkyl)₂, NO₂, N₃, halogenated alkyl especially CF₃, C₁₋₄ alkylamino, di(C₁₋₄ alkyl)amino, C₃₋₆ cycloalkylamino, C₁₋₆ alkoxy, SH, —S(C₁₋₄ alkyl), —S(C₁₋₄ alkenyl), —S(C₁₋₄ alkynyl), C₁₋₆ alkylthio, C₁₋₆ alkylsulfonyl, (C₁₋₄ alkyl)₀₋₂ aminomethyl, C₃₋₆ cycloalkylamino-alkenyl, -alkynyl, —(O)alkyl, —(O)alkenyl, —(O)alkynyl, —(O)acyl, —O(C₁₋₄ alkyl), —O(C₁₋₄ alkenyl), —O(C₁₋₄ alkynyl), —O—C(O)NH₂, —OC(O)N(alkyl), —OC(O)R'R", —C(O)OH, C(O)O-alkyl, C(O)O-alkenyl, C(O)O-alkynyl, S-alkyl, S-acyl, S-alkenyl, S-alkynyl, SCN, OCN, NC, —C(O)—NH₂, C(O)NH(alkyl), C(O)N(alkyl)₂, C(O)NH(acyl), C(O)N(acyl)₂, (S)—NH₂, NH-alkyl, N(dialkyl)₂, NH-acyl, N-diacyl, or a 3-7 membered heterocycle having O, S, or N taken independently in any combination;
each R' and R" independently is H, C₁₋₆ alkyl, C₂₋₆ alkenyl, C₂₋₆ alkynyl, halogen, halogenated alkyl, OH, CN, N₃, carboxy, C₁₋₄ alkoxycarbonyl, NH₂, C₁₋₄ alkylamino, di(C₁₋₄ alkyl)amino, C₁₋₆ alkoxy, C₁₋₆ alkylsulfonyl, or (C₁₋₄ alkyl)₀₋₂ aminomethyl; and
all tautomeric, enantiomeric and stereoisomeric forms thereof;
with the caveat that when X is S in Formula (I), then the compound is not 5-(4-amino-imidazo[4,5-d][1,2,3]triazin-7-yl)-2-hydroxymethyl-tetrahydro-thiophen-3-ol or 7-(4-hydroxy-5-hydroxy-methyl-tetrahydro-thiophen-2-yl)-3,7-dihydro-imidazo[4,5-d][1,2,3]triazin-4-one.

In a second principal embodiment, a compound of the Formula (II), or a pharmaceutically acceptable salt or prodrug thereof, is provided:

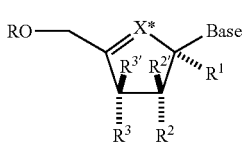

(II)

wherein:

R, $R^2$, $R^{2'}$, $R^3$, and $R^{3'}$ are all as defined above;

X* is $CY^3$;

$Y^3$ is hydrogen, alkyl, bromo, chloro, fluoro, iodo, azido, cyano, alkenyl, alkynyl, —C(O)O(alkyl), —C(O)O(lower alkyl), $CF_3$, —$CONH_2$, —CONH(alkyl), or —CON(alkyl)$_2$;

$R^1$ is H, OH, optionally substituted alkyl including lower alkyl, azido, cyano, optionally substituted alkenyl or alkynyl, —C(O)O-(alkyl), —C(O)O(lower alkyl), —C(O)O-(alkenyl), —C(O)O-(alkynyl), —O(acyl), —O(lower acyl), —O(alkyl), —O(lower alkyl), —O(alkenyl), —O(alkynyl), halogen, halogenated alkyl, —$NO_2$, —$NH_2$, —NH(lower alkyl), —N(lower alkyl)$_2$, —NH(acyl), —N(acyl)$_2$, —C(O)$NH_2$, —C(O)NH(alkyl), or —C(O)N(alkyl)$_2$, wherein an optional substitution on alkyl, alkenyl, and/or alkynyl may be one or more halogen, hydroxy, alkoxy or alkylthio groups taken in any combination;

Base is defined as above for formulae (A)-(G); and

A and Z are as defined above, with the caveat that when X is S in Formula (I), then the compound is not 5-(4-amino-imidazo[4,5-d][1,2,3]triazin-7-yl)-2-hydroxymethyl-tetrahydro-thiophen-3-ol or 7-(4-hydroxy-5-hydroxy-methyl-tetrahydro-thiophen-2-yl)-3,7-dihydro-imidazo[4,5-d][1,2,3]triazin-4-one; and all tautomeric, enantiomeric and stereoisomeric forms thereof.

In preferred embodiments, Bases (A)-(G) have a structure selected from the group consisting of:

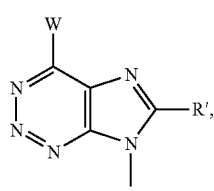

(i)

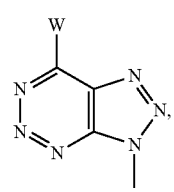

(ii)

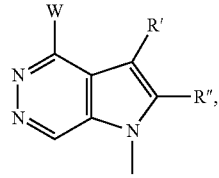

(iii)

-continued

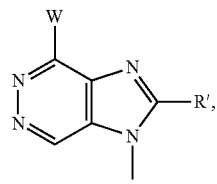

(iv)

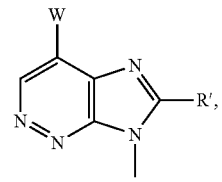

(v)

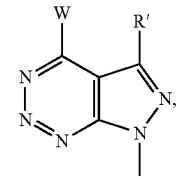

(vi)

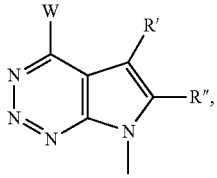

(vii)

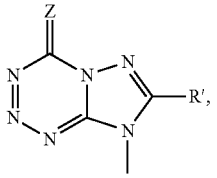

(viii)

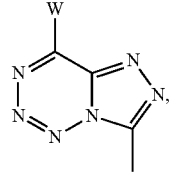

(ix)

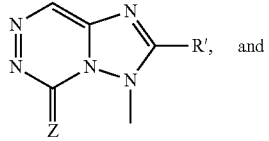

(x)

and

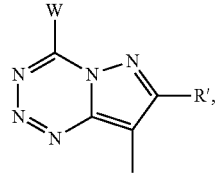

(xi)

wherein each R' and R" independently is H, $C_{1-6}$ alkyl, $C_{2-6}$ alkenyl, $C_{2-6}$ alkynyl, halogen, halogenated alkyl, OH, CN, $N_3$, carboxy, $C_{1-4}$ alkoxycarbonyl, $NH_2$, $C_{1-4}$ alkylamino, di($C_{1-4}$ alkyl)amino, $C_{1-6}$ alkoxy, $C_{1-6}$ alkylsulfonyl, ($C_{1-4}$ alkyl)$_{0-2}$ aminomethyl, as provided above in the definitions of A and Z for the Base Formulae (A)-(G);

each W is Cl, Br, I, F, halogenated alkyl, alkoxy, OH, SH, O-alkyl, S-alkyl, O-alkenyl, O-alkynyl, S-alkenyl, S-alkynyl, —OC(O)NR$^4$R$^4$, O-acyl, S-acyl, CN, SCN, OCN, NO$_2$, N$_3$, NH$_2$, NH(alkyl), N(alkyl)$_2$, NH-cycloalkyl, NH-acyl, NH=NH, CONH$_2$, CONH(alkyl), or CON(alkyl)$_2$;

each R$^4$ is independently H, acyl, or C$_{1-6}$ alkyl; and each Z is O, S, NH, N—OH, N—NH$_2$, NH(alkyl), N(alkyl)$_2$, N-cycloalkyl, alkoxy, CN, SCN, OCN, SH, NO$_2$, NH$_2$, N$_3$, NH=NH, NH(alkyl), N(alkyl)$_2$, CONH$_2$, CONH(alkyl), or CON(alkyl)$_2$.

In its preferred embodiments, the compounds of the present invention comprise nucleosides in which each variable in Formula (I) is selected from the following, in any combination: X is O or S; R is H or phosphate; R$_1$ is H, CH$_2$OH, or CONH$_2$; R$_2$ is OH or F; R$_3$ is alkyl, especially methyl or propynyl, or H at the 3' position; A is H, CH or N; Z is O, S, or NH; W is NH$_2$, Cl, OMe, OH, NH-cyclopropyl, S-Me; and each R' and R" independently is Cl, CN, CONH$_2$ or Me.

In its preferred embodiments for Formula (II), the compounds of the present invention comprise nucleosides in which each variable in Formula (II) is selected from the following, in any combination: X* is CH; R is H or phosphate; R$_1$ is H, CH$_2$OH, or CONH$_2$; R$_2$ is OH or F; R$_3$ is alkyl, especially methyl or propynyl, or H at the 3' position; A is H, CH or N; Z is O, S, or NH; W is NH$_2$, Cl, OMe, OH, NH-cyclopropyl, S-Me; and each R' and R" independently is Cl, CN, CONH$_2$ or Me.

In all embodiments, optional substituents are selected from the group consisting of one or more halogen, amino, hydroxy, carboxy and alkoxy groups or atoms, among others. It is to be understood that all stereoisomeric and tautomeric forms of the compounds shown are included herein.

In one particular embodiment, a compound of the Formula (III), or a pharmaceutically acceptable salt or prodrug thereof, is provided:

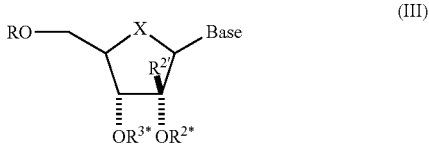

(III)

each R, R$^{2*}$, and R$^{3*}$ independently is H, phosphate (including mono-, di-, or triphosphate or a stabilized phosphate prodrug) or phosphonate; optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), lipid, phospholipid, carbohydrate, peptide, cholesterol, an amino acid residue or derivative, or other pharmaceutically acceptable leaving group that is capable of providing H or phosphate when administered in vivo;

X is O, S[O]$_n$, CH$_2$, CHOH, CH-alkyl, CH-alkenyl, CH-alkynyl, C-dialkyl, CH—O-alkyl, CH—O-alkenyl, CH—O-alkynyl, CH—S-alkyl, CH—S-alkenyl, CH—S-alkynyl, NH, N-alkyl, N-alkenyl, N-alkynyl, S(O)N-alkyl, S(O)N-alkenyl, S(O)N-alkynyl, SCH-halogen, or C-(halogen)$_2$, wherein alkyl, alkenyl or alkynyl optionally may be substituted;

n is 0-2;

each R$^{2'}$ independently is H; optionally substituted alkyl, alkenyl, or alkynyl; —C(O)O(alkyl), —C(O)O(lower alkyl), —C(O)O(alkenyl), —C(O)O(alkynyl), —C(O)NH$_2$, —C(O)NH(alkyl), —C(O)N(alkyl)$_2$, —OH, —O(acyl), —O(lower acyl), —O(alkyl), —O(lower alkyl), —O(alkenyl), halogen, halogenated alkyl and particularly CF$_3$, azido, cyano, NO$_2$, —S(alkyl), —S(alkenyl), —S(alkynyl), NH$_2$, —NH(alkyl), —N(alkyl)$_2$, —NH(alkenyl), —NH(alkynyl), —NH(acyl), or —N(acyl)$_2$; and Base is defined as above for formulae (A)-(G); and preferably is a Base as defined by structures (i)-(xi) above.

In one embodiment, the R$^{2'}$ is an optionally substituted alkyl, alkenyl, or alkynyl; halogen, halogenated alkyl and particularly CF$_3$, azido, or cyano. In a particular embodiment, R$^{2'}$ is an optionally substituted alkyl, alkenyl, or alkynyl; halogen, halogenated alkyl and particularly CF$_3$. In yet another particular embodiment, R$^{2'}$ is CH$_3$ or CF$_3$.

In one embodiment, each R, R$^{2*}$, and R$^{3*}$ is independently H, phosphate (including mono-, di-, or triphosphate or a stabilized phosphate prodrug) or phosphonate. In another embodiment, each R, R$^{2*}$, and R$^{3*}$ is independently H. In yet another embodiment, each R, R$^{2*}$, and R$^{3*}$ is independently H, acyl, or an amino acid acyl residue.

In one embodiment, X is O or S. In another embodiment, X is O.

In another particular embodiment, a compound of the Formula (IV), or a pharmaceutically acceptable salt or prodrug thereof, is provided:

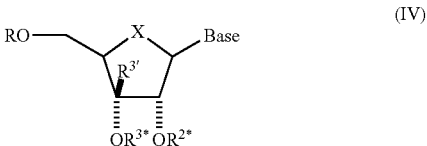

(IV)

each R, R$^{2*}$, and R$^{3*}$ independently is H, phosphate (including mono-, di-, or triphosphate or a stabilized phosphate prodrug) or phosphonate; optionally substituted alkyl including lower alkyl, optionally substituted alkenyl or alkynyl, acyl, —C(O)-(alkyl), —C(O)(lower alkyl), —C(O)-(alkenyl), —C(O)-(alkynyl), lipid, phospholipid, carbohydrate, peptide, cholesterol, an amino acid residue or derivative, or other pharmaceutically acceptable leaving group that is capable of providing H or phosphate when administered in vivo;

X is O, S[O]$_n$, CH$_2$, CHOH, CH-alkyl, CH-alkenyl, CH-alkynyl, C-dialkyl, CH—O-alkyl, CH—O-alkenyl, CH—O-alkynyl, CH—S-alkyl, CH—S-alkenyl, CH—S-alkynyl, NH, N-alkyl, N-alkenyl, N-alkynyl, S(O)N-alkyl, S(O)N-alkenyl, S(O)N-alkynyl, SCH-halogen, or C-(halogen)$_2$, wherein alkyl, alkenyl or alkynyl optionally may be substituted;

n is 0-2;

each R$^{3'}$ independently is H; optionally substituted alkyl, alkenyl, or alkynyl; —C(O)O(alkyl), —C(O)O(lower alkyl), —C(O)O(alkenyl), —C(O)O(alkynyl), —C(O)NH$_2$, —C(O)NH(alkyl), —C(O)N(alkyl)$_2$, —OH, —O(acyl), —O(lower acyl), —O(alkyl), —O(lower alkyl), —O(alkenyl), halogen, halogenated alkyl and particularly CF$_3$, azido, cyano, NO$_2$, —S(alkyl), —S(alkenyl), —S(alkynyl), NH$_2$, —NH(alkyl), —N(alkyl)$_2$, —NH(alkenyl), —NH(alkynyl), —NH(acyl), or —N(acyl)$_2$; and Base is defined as above for formulae (A)-(G); and preferably is a Base as defined by structures (i)-(xi) above.

In one embodiment, the $R^{3'}$ is an optionally substituted alkyl, alkenyl, or alkynyl; halogen, halogenated alkyl and particularly $CF_3$, azido, or cyano. In a particular embodiment, $R^{3'}$ is an optionally substituted alkyl, alkenyl, or alkynyl; halogen, halogenated alkyl and particularly $CF_3$. In yet another particular embodiment, $R^{3'}$ is $CH_3$ or $CF_3$.

In one embodiment, each R, $R^{2*}$, and $R^{3*}$ is independently H, phosphate (including mono-, di-, or triphosphate or a stabilized phosphate prodrug) or phosphonate. In another embodiment, each R, $R^{2*}$, and $R^{3*}$ is independently H. In yet another embodiment, each R, $R^{2*}$, and $R^{3*}$ is independently H, acyl, or an amino acid acyl residue.

In one embodiment, X is O or S. In another embodiment, X is O.

The beta-D- and beta-L-nucleosides of this invention belong to a class of anti-pestivirus, anti-flavivirus and anti-HCV agents that inhibit viral polymerase. Triphosphate nucleosides can be screened for their ability to inhibit viral polymerase, whether HCV, flavivirus or pestivirus, in vitro according to screening methods set forth below. Chiron Corporation developed a replicon system for testing potential anti-HCV compounds that utilizes a particular peptide sequence having an HCV protease-recognition site (U.S. Pat. No. 6,436,666; U.S. Pat. No. 6,416,946; U.S. Pat. No. 6,416,944; U.S. Pat. No. 6,379,886; and U.S. Pat. No. 6,326,151, to Chiron Corporation). Other systems for assessing the ability of compounds to inhibit HCV and related viruses include those of Rice (see U.S. Pat. No. 5,874,565) and the polymerase inhibition assay of Dr. Ralf Bartenschlager (see EP 1 043 399 A2).

An alternative means of assessing a compound's ability to inhibit HCV, pestivirus and/or flavivirus is through the use of predictive animal model systems. The model of choice for testing HCV is the chimpanzee, which has been used by the applicants. Chimpanzees provide an excellent mammalian system for study of anti-HCV compounds and an insight into the predictability or unpredictability of drug activity based on the closeness of their species relationship to humans.

The active compounds of the present invention can be administered in combination, alternation or sequential steps with another anti-HCV agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In particular, the present invention provides the following:

a) a beta-D- or beta-L-nucleoside compound of Formula (I)-(IV), or a pharmaceutically acceptable salt or prodrug thereof;

b) a pharmaceutical composition comprising a beta-D- or beta-L-nucleoside compound of Formula (I)-(IV), or a pharmaceutically acceptable salt or prodrug thereof, optionally together with a pharmaceutically acceptable carrier, excipient or diluent;

c) a pharmaceutical composition comprising a beta-D- or beta-L-nucleoside compound of Formula (I)-(IV), or a pharmaceutically acceptable salt or prodrug thereof, with one or more other effective antiviral agents, optionally with a pharmaceutically acceptable carrier or diluent;

d) a pharmaceutical composition for the treatment or prophylaxis of a pestivirus, flavivirus or HCV infection in a host, especially a host diagnosed as having or being at risk for such infection, comprising a beta-D- or beta-L-nucleoside compound of Formula (I)-(IV), or a pharmaceutically acceptable salt or prodrug thereof, together with a pharmaceutically acceptable carrier or diluent;

e) a pharmaceutical formulation comprising the beta-D- or beta-L-nucleoside compound of Formula (I)-(IV), or a pharmaceutically acceptable salt or prodrug thereof, together with a pharmaceutically acceptable carrier, excipient or diluent;

f) a method for the treatment of a pestivirus, flavivirus or HCV infection in a host comprising a beta-D- or beta-L-nucleoside compound of Formula (I)-(IV), or a pharmaceutically acceptable salt or prodrug thereof, optionally with a pharmaceutically acceptable carrier, excipient or diluent;

g) a method for the treatment of a pestivirus, flavivirus or HCV infection in a host comprising administering an effective amount of a beta-D- or beta-L-nucleoside compound of Formula (I)-(IV), or a pharmaceutically acceptable salt or prodrug thereof, with one or more other effective antiviral agents, optionally with a pharmaceutically acceptable carrier, excipient or diluent;

h) a method for the treatment of a pestivirus, flavivirus or HCV infection in a host comprising administering an effective amount of a beta-D- or beta-L-nucleoside compound of Formula (I)-(IV), or a pharmaceutically acceptable salt or prodrug thereof, with one or more other effective antiviral agents, optionally with a pharmaceutically acceptable carrier, excipient or diluent;

i) a method for the treatment of a pestivirus, flavivirus or HCV infection in a host comprising administering an effective amount of a beta-D- or beta-L-nucleoside compound of Formula (I)-(IV), or a pharmaceutically acceptable salt or prodrug thereof, with one or more other effective antiviral agents, optionally with a pharmaceutically acceptable carrier, excipient or diluent;

j) a method for the treatment of a pestivirus, flavivirus or HCV infection in a host comprising administering an effective amount of a beta-D- or beta-L-nucleoside compound of Formula (I)-(IV), or a pharmaceutically acceptable salt or prodrug thereof, with one or more other effective antiviral agents, optionally with a pharmaceutically acceptable carrier, excipient or diluent;

k) use of a beta-D- or beta-L-nucleoside compound of Formula (I)-(IV), or a pharmaceutically acceptable salt or prodrug thereof, optionally with a pharmaceutically acceptable carrier or diluent, for the treatment of a pestivirus, flavivirus or HCV infection in a host;

l) use of a beta-D- or beta-L-nucleoside compound of Formula (I)-(IV), or a pharmaceutically acceptable salt or prodrug thereof, with one or more other effective antiviral agents, optionally with a pharmaceutically acceptable carrier or diluent, for the treatment of a pestivirus, flavivirus and/or HCV infection in a host;

m) use of a beta-D- or beta-L-nucleoside compound of Formula (I)-(IV), or a pharmaceutically acceptable salt or prodrug thereof, optionally with a pharmaceutically acceptable carrier or diluent, in the manufacture of a medicament for the treatment of a pestivirus, flavivirus and/or HCV infection in a host;

n) use of a beta-D- or beta-L-nucleoside compound of Formula (I)-(IV), or a pharmaceutically acceptable salt or prodrug thereof, with one or more other effective antiviral agents and optionally with a pharmaceutically acceptable carrier, excipient or diluent, in the manufacture of a medicament for the treatment of a pestivirus, flavivirus and/or HCV infection in a host;

o) a beta-D- or beta-L-nucleoside compound of Formula (I)-(IV), or a pharmaceutically acceptable salt or prodrug thereof, substantially in the absence of enantiomers of the described nucleoside, or substantially isolated from other chemical entities;

p) a process for the preparation of a beta-D- or beta-L-nucleoside compound of Formula (I)-(IV), or a pharmaceutically acceptable salt or prodrug thereof, as provided in more detail below; and q) a process for the preparation of a beta-D- or beta-L-nucleoside compound of Formula (I)-(IV), or a pharmaceutically acceptable salt or prodrug thereof, substantially in the absence of enantiomers of the described nucleoside or substantially isolated from other chemical entities.

The active compound can be administered as any salt or prodrug that upon administration to the recipient is capable of providing directly or indirectly the parent compound, or that exhibits activity itself. Non-limiting examples are the pharmaceutically acceptable salts, which are alternatively referred to as "physiologically acceptable salts", and a compound that has been alkylated or acylated at the 5'-position or on the purine or pyrimidine base, thereby forming a type of "pharmaceutically acceptable prodrug". Further, the modifications can affect the biological activity of the compound, in some cases increasing the activity over the parent compound. This can easily be assessed by preparing the salt or prodrug and testing its antiviral activity according to the methods described herein, or other methods known to those skilled in the art.

Stereochemistry

It is appreciated that nucleosides of the present invention have several chiral centers and may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein. It being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

DEFINITIONS

The term "alkyl" as used herein, unless otherwise specified, refers to a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Moieties with which the alkyl group can be substituted with one or more substituents are selected from the group consisting of halo, including Cl, F, Br and I so as to form, for eg., CF$_3$, 2-Br-ethyl, CH$_2$F, CH$_2$Cl, CH$_2$CF$_3$, or CF$_2$CF$_3$; hydroxyl, for eg. CH$_2$OH; amino, for eg., CH$_2$NH$_2$, CH$_2$NHCH$_3$, or CH$_2$N(CH$_3$)$_2$; carboxylate; carboxamido; alkylamino; arylamino; alkoxy; aryloxy; nitro; azido, for eg., CH$_2$N$_3$; cyano, for eg., CH$_2$CN; thio; sulfonic acid; sulfate; phosphonic acid; phosphate; and phosphonate, either unprotected or protected as necessary, known to those skilled in the art, for eg., as taught in Greene et al., *Protective Groups in Organic Synthesis*, John Wiley and Sons, Second Edition (1991), incorporated herein by reference.

The term "lower alkyl" as used herein, and unless otherwise specified, refers to a C$_1$ to C$_6$ saturated straight, branched, or if appropriate, cyclic as in cyclopropyl, for eg., alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The terms "alkylamino" and "arylamino" refer to an amino group that has one or two alkyl or aryl substituents, respectively.

The term "protected" as used herein and, unless otherwise defined, refers to a group that is added to an oxygen, nitrogen or phosphorus atom to prevent its further reaction or for other purposes. Numerous oxygen and nitrogen protecting groups are known to those skilled in the art of organic synthesis.

The term "aryl" as used herein and, unless otherwise specified, refers to phenyl, biphenyl or naphthyl, and preferably phenyl. The term includes both substituted and unsubstituted moieties. The aryl group can be substituted with one or more moieties selected from the group consisting of alkyl, hydroxyl, amino, alkylamino, arylamino, alkoxy, aryloxy, nitro, cyano, thio, alkylthio, carboxamido, carboxylate, sulfonic acid, sulfate, phosphonic acid, phosphate, or phosphonate, either unprotected or protected as necessary, as known to those skilled in the art, for eg., as taught in Greene et al., *Protective Groups in Organic Synthesis*, John Wiley and Sons, Second Edition (1991), incorporated herein by reference.

The terms "alkaryl" and "akylaryl" refer to an alkyl group with an aryl substituent.

The terms "aralkyl" and "arylalkyl" refer to an aryl group with an alkyl substituent.

The term "halo" as used herein includes bromo, chloro, iodo and fluoro.

The term purine base includes, but is not limited to, adenine, 2-azapurine bases that are optionally substituted imidazo-triazines, imidazo-pyridazines, pyrrolo-pyridazines, pyrrolo-triazines, triazolo-triazines including triazolo[4,5-d]triazines, pyrazolo-triazines including pyrazolo[4,5-d]triazines, N$^6$-alkylpurines, N$^6$-acylpurines (wherein acyl is C(O)(alkyl, aryl, alkylaryl, or arylalkyl), N$^6$-benzylpurine, N$^6$-halopurine, N$^6$-vinylpurine, N$^6$-acetylenic purine, N$^6$-acyl purine, N$^6$-hydroxyalkyl purine, N$^6$-thioalkyl purine, N$^2$-alkylpurines, N$^2$-alkyl-6-thiopurines, C$^5$-hydroxyalkyl purine, N$^2$-alkylpurines, N$^2$-alkyl-6-thiopurines, triazolopyridinyl, imidazolopyridinyl, pyrrolopyrimidinyl, and pyrazolopyrimidinyl.

The Base maybe selected from the group consisting of:

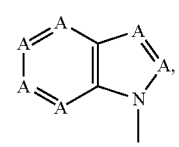
(A)

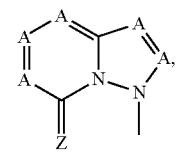
(B)

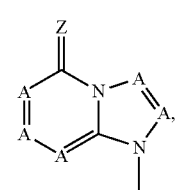
(C)

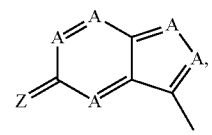
(D)

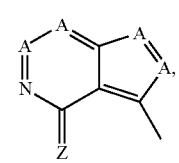
(E)

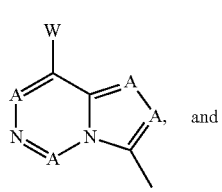
and
(F)

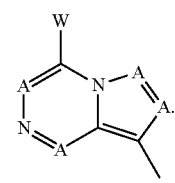
(G)

The term "acyl" refers to a carboxylic acid ester in which the non-carbonyl moiety of the ester group is selected from straight, branched, or cyclic alkyl or lower alkyl; alkoxyalkyl including methoxymethyl; aralkyl including benzyl; aryloxyalkyl such as phenoxymethyl; aryl including phenyl optionally substituted with halogen, C$_1$-C$_6$ alkyl or C$_1$-C$_6$ alkoxy; sulfonate esters such as alkyl or aralkyl sulphonyl including methanesulfonyl; the mono-, di- or triphosphate ester; trityl or monomethoxytrityl; substituted benzyl; trialkylsilyl as, for eg., dimethyl-t-butylsilyl or diphenylmethylsilyl. Aryl groups in the esters optimally comprise a phenyl group. The term "lower acyl" refers to an acyl group in which the non-carbonyl moiety is lower alkyl.

As used herein, the terms "substantially free of" and "substantially in the absence of" refer to a nucleoside composition that includes at least 85-90% by weight, preferably 95%-98% by weight, and even more preferably 99%-100% by weight, of the designated enantiomer of that nucleoside. In a preferred embodiment, the compounds listed in the methods and compounds of this invention are substantially free of enantiomers other than the one designated.

Similarly, the term "isolated" refers to a nucleoside composition that includes at least 85%-90% by weight, preferably 95%-98% by weight, and even more preferably 99%-100% by weight, of the nucleoside, the remainder comprising other chemical species or enantiomers.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

The term "host", as used herein, refers to a unicellular or multicellular organism in which the virus can replicate, including cell lines and animals, and preferably a human. Alternatively, the host can be carrying a part of the flavivirus or pestivirus genome, whose replication or function can be altered by the compounds of the present invention. The term host specifically refers to infected cells, cells transfected with all or part of the flavivirus or pestivirus genome and animals, in particular, primates (including chimpanzees) and humans. In most animal applications of the present invention, the host is a human patient. Veterinary applications, in certain indications, however, are clearly anticipated by the present invention such as in chimpanzees.

The term "pharmaceutically acceptable salt or prodrug" is used throughout the specification to describe any pharmaceutically acceptable form (ester, phosphate ester, salt of an ester or a related group) of a nucleoside compound, which, upon administration to a patient, provides the nucleoside compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example, hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against flavivirus, pestivirus or HCV, or are metabolized to a compound that exhibits such activity.

Nucleoside Prodrug Formulations

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono-, di- or triphosphate of the nucleoside reduces polarity and allows passage into cells. Examples of substituent groups that can replace one or more hydrogens on the phosphate moiety are alkyl, aryl, steroids, carbohydrates, including sugars, 1,2-diacylglycerol, alcohols, acyl (including lower acyl); alkyl (including lower alkyl); sulfonate ester including alkyl or arylalkyl sulfonyl including methanesulfonyl and benzyl, wherein the phenyl group is optionally substituted with one or more substituents as provided in the definition of an aryl given herein; optionally substituted arylsulfonyl; a lipid, including a phospholipid; an amino acid residue or derivative; a carbohydrate; a peptide; cholesterol; or other pharmaceutically acceptable leaving group which, when administered in vivo, provides a compound wherein $R^1$ is independently H or phosphate. Many more are described in R. Jones and N. Bischoferger, *Antiviral Research*, 1995, 27:1-17. Any of these can be used in combination with the disclosed nucleosides to achieve a desired effect.

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The active nucleoside can also be provided as a 5'-phosphoether lipid or a 5'-ether lipid, as disclosed in the following references, which are incorporated by reference herein: Kucera, L. S., N. Iyer, E. Leake, A. Raen, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses.* 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991.

Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); U.S. Pat. No. 5,194, 654 (Mar. 16, 1993, Hostetler et al., and U.S. Pat. No. 5,223, 263 (Jun. 29, 1993, Hostetler et al.); all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Combination and Alternation Therapy

It has been recognized that drug-resistant variants of HCV can emerge after prolonged treatment with an antiviral agent. Drug resistance most typically occurs by mutation of a gene that encodes for an enzyme used in viral replication. The efficacy of a drug against HCV infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Any of the HCV treatments described in the Background of the Invention can be used in combination or alternation with the compounds described in this specification. Nonlimiting examples include:

(1) Interferon

Interferons (IFNs) are compounds that have been commercially available for the treatment of chronic hepatitis for nearly a decade. IFNs are glycoproteins produced by immune cells in response to viral infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%-9% of patients chronically infected with HCV (Gary L. Davis. Gastroenterology 118:S104-S114, 2000).

A number of patents disclose HCV treatments using interferon-based therapies. For example, U.S. Pat. No. 5,980,884 to Blatt et al. discloses methods for re-treatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,908,621 to Glue et al. discloses the use of polyethylene glycol modified interferon for the treatment of HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Imakawa discloses the use of human interferon tau proteins for treating HCV. Other interferon-based treatments for HCV are disclosed in U.S. Pat. No. 5,676,942 to Testa et al., U.S. Pat. No. 5,372,808 to Blatt et al., and U.S. Pat. No. 5,849,696.

(2) Ribavirin (Battaglia, A. M. et al., Ann. Pharmacother, 2000, 34, 487-494); Berenguer, M. et al. Antivir. Ther., 1998, 3 (Suppl. 3), 125-136).

Ribavirin (1-β-D-ribofuranosyl-1-1,2,4-triazole-3-carboxamide) is a synthetic, non-interferon-inducing, broad spectrum antiviral nucleoside analog. It is sold under the trade names Virazole™ (The Merck Index, 11th edition, Editor: Budavari, S., Merck & Co., Inc., Rahway, N.J., p 1304, 1989); Rebetol (Schering Plough) and Co-Pegasus (Roche). U.S. Pat. No. 3,798,209 and RE29,835 (ICN Pharmaceuticals) disclose and claim ribavirin. Ribavirin is structurally similar to guanosine, and has in vitro activity against several DNA and RNA viruses including Flaviviridae (Gary L. Davis. Gastroenterology 118:S104-S114, 2000). U.S. Pat. No. 4,211,771 (to ICN Pharmaceuticals) discloses the use of ribavirin as an antiviral agent. Ribavirin reduces serum amino transferase levels to normal in 40% of patients, but it does not lower serum levels of HCV-RNA (Gary L. Davis. Gastroenterology 118:S104-S114, 2000). Thus, ribavirin alone is not effective in reducing viral RNA levels. Additionally, ribavirin has significant toxicity and is known to induce anemia.

Combination of Interferon and Ribavirin

Schering-Plough sells ribavirin as Rebetol® capsules (200 mg) for administration to patients with HCV. The U.S. FDA has approved Rebetol capsules to treat chronic HCV infection in combination with Schering's alpha interferon-2b products Intron® A and PEG-Intron™. Rebetol capsules are not approved for monotherapy (i.e., administration independent of Intron®A or PEG-Intron), although Intron A and PEG-Intron are approved for monotherapy (i.e., administration without ribavirin). Hoffman La Roche is selling ribavirin under the name Co-Pegasus in Europe and the United States, also for use in combination with interferon for the treatment of HCV. Other alpha interferon products include Roferon-A (Hoffmann-La Roche), Infergen® (Intermune, formerly Amgen's product), and Wellferon® (Wellcome Foundation) are currently FDA-approved for HCV monotherapy. Interferon products currently in development for HCV include: Roferon-A (interferon alfa-2a) by Roche, PEGASYS (pegylated interferon alfa-2a) by Roche, INFERGEN (interferon alfacon-1) by InterMune, OMNIFERON (natural interferon) by Viragen, ALBUFERON by Human Genome Sciences, REBIF (interferon beta-1a) by Ares-Serono, Omega Interferon by BioMedicine, Oral Interferon Alpha by Amarillo Biosciences, and Interferon gamma-1b by InterMune.

The combination of IFN and ribavirin for the treatment of HCV infection has been reported to be effective in the treatment of IFN naïve patients (for example, Battaglia, A. M. et al., Ann. Pharmacother. 34:487-494, 2000). Combination treatment is effective both before hepatitis develops and when histological disease is present (for example, Berenguer, M. et al. Antivir. Ther. 3 (Suppl. 3):125-136, 1998). Currently, the most effective therapy for HCV is combination therapy of pegylated interferon with ribavirin (2002 NIH Consensus Development Conference on the Management of Hepatitis C). However, the side effects of combination therapy can be significant and include hemolysis, flu-like symptoms, anemia, and fatigue (Gary L. Davis. Gastroenterology 118:S104-S114, 2000).

(3) Protease inhibitors have been developed for the treatment of Flaviviridae infections. Examples, include, but are not limited to the following Substrate-based NS3 protease inhibitors (see, for example, Attwood et al., Antiviral peptide derivatives, PCT WO 98/22496, 1998; Attwood et al., Antiviral Chemistry and Chemotherapy 1999, 10, 259-273; Attwood et al., Preparation and use of amino acid derivatives as anti-viral agents, German Patent Pub. DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (see, for example, Llinas-Brunet et al, Hepatitis C inhibitor peptide analogues, PCT WO 99/07734);

Non-substrate-based inhibitors such as 2,4,6-trihydroxy-3-nitro-benzamide derivatives (see, for example, Sudo K. et al., *Biochemical and Biophysical Research Communications,* 1997, 238, 643-647; Sudo K. et al. *Antiviral Chemistry and Chemotherapy,* 1998, 9, 186), including RD3-4082 and RD3-4078, the former substituted on the amide with a 14 carbon chain and the latter processing a para-phenoxyphenyl group;

Phenanthrenequinones possessing activity against protease, for example in a SDS-PAGE and/or autoradiography assay, such as, for example, Sch 68631, isolated from the fermentation culture broth of *Streptomyces* sp., (see, for example, Chu M. et al., *Tetrahedron Letters,* 1996, 37, 7229-7232), and Sch 351633, isolated from the fungus *Penicillium griseofulvum,* which demonstrates activity in a scintillation proximity assay (see, for example, Chu M. et al., *Bioorganic and Medicinal Chemistry Letters* 9, 1949-1952); and Selective NS3 inhibitors, for example, based on the macromolecule elgin c, isolated from leech (see, for example, Qasim M. A. et al., *Biochemistry,* 1997, 36, 1598-1607). Nanomolar potency against the HCV NS3 protease enzyme has been achieved by the design of selective inhibitors based on the macromolecule eglin c. Eglin c, isolated from leech, is a potent inhibitor of several serine proteases such as *S. griseus* proteases A and B, α-chymotrypsin, chymase and subtilisin.

Several U.S. patents disclose protease inhibitors for the treatment of HCV. Non-limiting examples include, but are not limited to the following. U.S. Pat. No. 6,004,933 to Spruce et al. discloses a class of cysteine protease inhibitors for inhibiting HCV endopeptidase. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor. The use of restriction enzymes to treat HCV is disclosed in U.S. Pat. No. 5,538,865 to Reyes et al. Peptides as NS3 serine protease inhibitors of HCV are disclosed in WO 02/008251 to Corvas International, Inc, and WO 02/08187 and WO 02/008256 to Schering Corporation. HCV inhibitor tripeptides are disclosed in U.S. Pat. Nos. 6,534,523, 6,410,531, and U.S. Pat. No. 6,420,380 to Boehringer Ingelheim and WO 02/060926 to Bristol Myers Squibb. Diaryl peptides as NS3 serine protease inhibitors of HCV are disclosed in WO 02/48172 to Schering Corporation. Imidazoleidinones as NS3 serine protease inhibitors of HCV are disclosed in WO 02/08198 to Schering Corporation and WO 02/48157 to Bristol Myers Squibb. WO 98/17679 to Vertex Pharmaceuticals and WO 02/48116 to Bristol Myers Squibb also disclose HCV protease inhibitors.

(4) Thiazolidine derivatives, for example, that show relevant inhibition in a reverse-phase HPLC assay with an NS3/4A fusion protein and NS5A/5B substrate (see, for example, Sudo K. et al., *Antiviral Research*, 1996, 32, 9-18), especially compound RD-1-6250, possessing a fused cinnamoyl moiety substituted with a long alkyl chain, RD4 6205 and RD4 6193;

(5) Thiazolidines and benzanilides, for example, as identified in Kakiuchi N. et at *J. EBS Letters* 421, 217-220; Takeshita N. et al. *Analytical Biochemistry*, 1997, 247, 242-246;

(6) Helicase inhibitors (see, for example, Diana G. D. et at, Compounds, compositions and methods for treatment of hepatitis C, U.S. Pat. No. 5,633,358; Diana G. D. et at, Piperidine derivatives, pharmaceutical compositions thereof and their use in the treatment of hepatitis C, PCT WO 97/36554);

(7) Polymerase inhibitors such as
   i) nucleotide analogues, such as gliotoxin (see, for example, Ferrari R. et al. *Journal of Virology*, 1999, 73, 1649-1654);
   ii) the natural product cerulenin (see, for example, Lohmann V. et al., *Virology*, 1998, 249, 108-118); and
   iii) non-nucleoside polymerase inhibitors, including, for example, compound R803 (see, for example, WO 04/018463 A2 and WO 03/040112 A1, both to Rigel Pharmaceuticals, Inc.); substituted diamine pyrimidines (see, for example, WO 03/063794 A2 to Rigel Pharmaceuticals, Inc.); benzimidazole derivatives (see, for example, *Bioorg. Med. Chem. Lett.*, 2004, 14:119-124 and *Bioorg. Med. Chem. Lett.*, 2004, 14:967-971, both to Boehringer Ingelheim Corporation); N,N-disubstituted phenylalanines (see, for example, *J. Biol. Chem.*, 2003, 278:9495-98 and *J. Med. Chem.*, 2003, 13:1283-85, both to Shire Biochem, Inc.); substituted thiophene-2-carboxylic acids (see, for example, *Bioorg. Med. Chem. Lett.*, 2004, 14:793-796 and *Bioorg. Med. Chem. Lett.*, 2004, 14:797-800, both to Shire Biochem, Inc.); α,γ-diketoacids (see, for example, *J. Med. Chem.*, 2004, 14-17 and WO 00/006529 A1, both to Merck & Co., Inc.); and meconic acid derivatives (see, for example, *Bioorg. Med. Chem. Lett.*, 2004, 3257-3261, WO 02/006246 A1 and WO03/062211 A1, all to IRBM Merck & Co., Inc.);

(8) Antisense phosphorothioate oligodeoxynucleotides (S-ODN) complementary, for example, to sequence stretches in the 5' non-coding region (NCR) of the virus (see, for example, Alt M. et al., *Hepatology*, 1995, 22, 707-717), or to nucleotides 326-348 comprising the 3' end of the NCR and nucleotides 371-388 located in the core coding region of the HCV RNA (see, for example, Alt M. et al., *Archives of Virology*, 1997, 142, 589-599; Galderisi U. et al., *Journal of Cellular Physiology*, 1999, 181, 251-257).

(9) Inhibitors of IRES-dependent translation (see, for example, Ikeda N et al., Agent for the prevention and treatment of hepatitis C, Japanese Patent Pub. JP-08268890; Kai Y. et al. Prevention and treatment of viral diseases, Japanese Patent Pub. JP-10101591).

(10) Nuclease-resistant ribozymes (see, for example, Maccjak, D. J. et al., *Hepatology* 1999, 30, abstract 995; U.S. Pat. No. 6,043,077 to Barber et al., and U.S. Pat. Nos. 5,869,253 and 5,610,054 to Draper et al.).

(11) Nucleoside analogs have also been developed for the treatment of Flaviviridae infections.

Idenix Pharmaceuticals, Ltd. discloses branched nucleosides, and their use in the treatment of HCV and flaviviruses and pestiviruses in US Patent Publication Nos. 2003/0050229 A1, 2004/0097461 A1, 2004/0101535 A1, 2003/0060400 A1, 2004/0102414 A1, 2004/0097462 A1, and 2004/0063622 A1 which correspond to International Publication Nos. WO 01/90121 and WO 01/92282. A method for the treatment of hepatitis C infection (and flaviviruses and pestiviruses) in humans and other host animals is disclosed in the Idenix publications that includes administering an effective amount of a biologically active 1', 2', 3' or 4'-branched β-D or β-L nucleosides or a pharmaceutically acceptable salt or prodrug thereof, administered either alone or in combination, optionally in a pharmaceutically acceptable carrier. See also U.S. Patent Publication Nos. 2004/0006002 and 2004/0006007 as well as WO 03/026589 and WO 03/026675. Idenix Pharmaceuticals, Ltd. also discloses in US Patent Publication No. 2004/0077587 pharmaceutically acceptable branched nucleoside prodrugs, and their use in the treatment of HCV and flaviviruses and pestiviruses in prodrugs. See also PCT Publication Nos. WO 04/002422, WO 04/002999, and WO 04/003000. Further, Idenix Pharmaceuticals, Ltd. also discloses in WO 04/046331 Flaviviridae mutations caused by biologically active 2'-branched β-D or β-L nucleosides or a pharmaceutically acceptable salt or prodrug thereof.

Biota Inc. discloses various phosphate derivatives of nucleosides, including 1', 2', 3' or 4'-branched β-D or β-L nucleosides, for the treatment of hepatitis C infection in International Patent Publication WO 03/072757.

Emory University and the University of Georgia Research Foundation, Inc. (UGARF) discloses the use of 2'-fluoro-nucleosides for the treatment of HCV in U.S. Pat. No. 6,348,587. See also US Patent Publication No. 2002/0198171 and International Patent Publication WO 99/43691.

BioChem Pharma Inc. (now Shire Biochem, Inc.) discloses the use of various 1,3-dioxolane nucleosides for the treatment of a Flaviviridae infection in U.S. Pat. No. 6,566,365. See also U.S. Pat. Nos. 6,340,690 and 6,605,614; US Patent Publication Nos. 2002/0099072 and 2003/0225037, as well as International Publication No. WO 01/32153 and WO 00/50424.

BioChem Pharma Inc. (now Shire Biochem, Inc.) also discloses various other 2'-halo, 2'-hydroxy and 2'-alkoxy nucleosides for the treatment of a Flaviviridae infection in US Patent Publication No. 2002/0019363 as well as International Publication No. WO 01/60315 (PCT/CA01/00197; filed Feb. 19, 2001).

ICN Pharmaceuticals, Inc. discloses various nucleoside analogs that are useful in modulating immune response in U.S. Pat. Nos. 6,495,677 and 6,573,248. See also WO 98/16184, WO 01/68663, and WO 02/03997.

U.S. Pat. No. 6,660,721; US Patent Publication Nos. 2003/083307 A1, 2003/008841 A1, and 2004/0110718; as well as International Patent Publication Nos. WO 02/18404; WO 02/100415, WO 02/094289, and WO 04/043159; filed by F. Hoffmann-La Roche AG, discloses various nucleoside analogs for the treatment of HCV RNA replication.

Pharmasset Limited discloses various nucleosides and antimetabolites for the treatment of a variety of viruses, including Flaviviridae, and in particular HCV, in US Patent Publication Nos. 2003/0087873, 2004/0067877, 2004/0082574, 2004/0067877, 2004/002479, 2003/0225029, and 2002/00555483, as well as International Patent Publication Nos. WO 02/32920, WO 01/79246, WO 02/48165, WO 03/068162, WO 03/068164 and WO 2004/013298.

Merck & Co., Inc. and Isis Pharmaceuticals disclose in US Patent Publication No. 2002/0147160, 2004/0072788, 2004/0067901, and 2004/0110717; as well as the corresponding International Patent Publication Nos. WO 02/057425 (PCT/US02/01531; filed Jan. 18, 2002) and WO 02/057287 (PCT/US02/03086; filed Jan. 18, 2002) various nucleosides, and in particular several pyrrolopyrimidine nucleosides, for the treatment of viruses whose replication is dependent upon RNA-dependent RNA polymerase, including Flaviviridae, and in particular HCV. See also WO 2004/000858, WO 2004/003138, WO 2004/007512, and WO 2004/009020.

US Patent Publication No. 2003/028013 A1 as well as International Patent Publication Nos. WO 03/051899, WO 03/061576, WO 03/062255 WO 03/062256, WO 03/062257, and WO 03/061385, filed by Ribapharm, also are directed to the use of certain nucleoside analogs to treat hepatitis C virus.

Genelabs Technologies disclose in US Patent Publication No. 2004/0063658 as well as International Patent Publication Nos. WO 03/093290 and WO 04/028481 various base modified derivatives of nucleosides, including 1', 2', 3' or 4'-branched β-D or β-L nucleosides, for the treatment of hepatitis C infection.

Eldrup et al. (Oral Session V, Hepatitis C Virus, Flaviviridae; 16 International Conference on Antiviral Research (Apr. 27, 2003, Savannah, Ga.) p. A75) described the structure activity relationship of 2'-modified nucleosides for inhibition of HCV.

Bhat et al (Oral Session V, Hepatitis C Virus, Flaviviridae; 16$^{th}$ International Conference on Antiviral Research (Apr. 27, 2003, Savannah, Ga.); p A75) describe the synthesis and pharmacokinetic properties of nucleoside analogues as possible inhibitors of HCV RNA replication. The authors report that 2'-modified nucleosides demonstrate potent inhibitory activity in cell-based replicon assays.

Olsen et al. (Oral Session V, Hepatitis C Virus, Flaviviridae; 16$^{th}$ International Conference on Antiviral Research (Apr. 27, 2003, Savannah, Ga.) p A76) also described the effects of the 2'-modified nucleosides on HCV RNA replication.

(12) Other miscellaneous compounds including 1-aminoalkylcyclohexanes (for example, U.S. Pat. No. 6,034,134 to Gold et al.), alkyl lipids (for example, U.S. Pat. No. 5,922,757 to Chojkier et al.), vitamin E and other antioxidants (for example, U.S. Pat. No. 5,922,757 to Chojkier et al.), squalene, amantadine, bile acids (for example, U.S. Pat. No. 5,846,964 to Ozeki et al.), N-(phosphonoacetyl)-L-aspartic acid (for example, U.S. Pat. No. 5,830,905 to Diana et al.), benzenedicarboxamides (for example, U.S. Pat. No. 5,633,388 to Diana et al.), polyadenylic acid derivatives (for example, U.S. Pat. No. 5,496,546 to Wang et al.), 2',3'-dideoxyinosine (for example, U.S. Pat. No. 5,026,687 to Yarchoan et al.), benzimidazoles (for example, U.S. Pat. No. 5,891,874 to Colacino et al.), plant extracts (for example, U.S. Pat. No. 5,837,257 to Tsai et al., U.S. Pat. No. 5,725,859 to Omer et al., and U.S. Pat. No. 6,056,961), and piperidenes (for example, U.S. Pat. No. 5,830,905 to Diana et al.).

(13) Other compounds currently in clinical development for treatment of hepatitis C virus include, for example: Interleukin-10 by Schering-Plough, IP-501 by Interneuron, Merimebodib VX-497 by Vertex, AMANTADINE® (Symmetrel) by Endo Labs Solvay, HEPTAZYME® by RPI, IDN-6556 by Idun Pharma., XTL-002 by XTL., HCV/MF59 by Chiron, CIVACIR® (Hepatitis C Immune Globulin) by NABI, LEVOVIRIN® by ICN/Ribapharm, VIRAMIDINE® by ICN/Ribapharm, ZADAXIN® (thymosin alfa-1) by Sci Clone, thymosin plus pegylated interferon by Sci Clone, CEPLENE® (histamine dihydrochloride) by Maxim, VX 950/LY 570310 by Vertex/Eli Lilly, ISIS 14803 by Isis Pharmaceutical/Elan, IDN-6556 by Idun Pharmaceuticals, Inc., JTK 003 by AKROS Pharma, BILN-2061 by Boehringer Ingelheim, CellCept (mycophenolate mofetil) by Roche, T67, a β-tubulin inhibitor, by Tularik, a therapeutic vaccine directed to E2 by Innogenetics, FK788 by Fujisawa Healthcare, Inc., IdB 1016 (Siliphos, oral silybin-phosphatdylcholine phytosome), RNA replication inhibitors (VP50406) by ViroPharma/Wyeth, therapeutic vaccine by Intercell, therapeutic vaccine by Epimmune/Genencor, IRES inhibitor by Anadys, ANA 245 and ANA 246 by Anadys, immunotherapy (Therapore) by Avant, protease inhibitor by Corvas/SChering, helicase inhibitor by Vertex, fusion inhibitor by Trimeris, T cell therapy by CellExSys, polymerase inhibitor by Biocryst, targeted RNA chemistry by PTC Therapeutics, Dication by Immtech, Int., protease inhibitor by Agouron, protease inhibitor by Chiron/Medivir, antisense therapy by AVI BioPharma, antisense therapy by Hybridon, hemopurifier by Aethlon Medical, therapeutic vaccine by Merix, protease inhibitor by Bristol-Myers Squibb/Axys, Chron-VacC, a therapeutic vaccine, by Tripep, UT 231B by United Therapeutics, protease, helicase and polymerase inhibitors by Genelabs Technologies, IRES inhibitors by Immusol, R803 by Rigel Pharmaceuticals, INFERGEN® (interferon alpha-con-1) by InterMune, OMNIFERON® (natural interferon) by Viragen, ALBUFERON® by Human Genome Sciences, REBIF® (interferon beta-1a) by Ares-Serono, Omega Interferon by BioMedicine, Oral Interferon Alpha by Amarillo Biosciences, interferon gamma, interferon tau, and Interferon gamma-1b by InterMune.

Pharmaceutical Compositions

Hosts, including humans, infected with pestivirus, flavivirus, HCV or another organism replicating through a RNA-dependent RNA viral polymerase, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for pestivirus, flavivirus or HCV will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to one containing 7 to 3000 mg, or 70 to 1400 mg of active ingredient per unit dosage form. An oral dosage in one embodiment is 50-1000 mg. In another embodiment, the dosage form contains 0.5-500 mg; or 0.5-100 mg; or 0.5-50 mg; or 0.5-25 mg; or 1.0-10 mg.

Ideally the active ingredient should be administered to achieve peak plasma concentrations of the active compound of from about 0.2 to 70 µM, preferably about 1.0 to 10 µM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

Processes for the Preparation of Active Compounds

The nucleosides of the present invention can be synthesized by any means known in the art. In particular, the synthesis of the present nucleosides can be achieved by either alkylating the appropriately modified sugar, followed by glycosylation or glycosylation followed by alkylation of the nucleoside, though preferably alkylating the appropriately modified sugar, followed by glycosylation. The following non-limiting embodiments illustrate some general methodology to obtain the nucleosides of the present invention.

A. General Synthesis of 1'-C-Branched Nucleosides

1'-C branched ribonucleosides of the following structures:

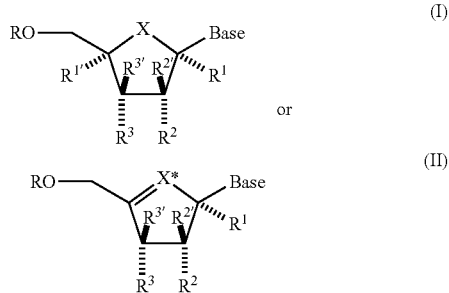

wherein

R is H, phosphate (including mono-, di-, or triphosphate or a stabilized phosphate prodrug) or phosphonate;

n is 0-2;

when X is CH$_2$, CHOH, CH-alkyl, CH-alkenyl, CH-alkynyl, C-dialkyl, CH—O-alkyl, CH—O-alkenyl, CH—O-alkynyl, CH—S-alkyl, CH—S-alkenyl, CH—S-alkynyl, CH-halogen, or C-(halogen)$_2$, then each R$^1$ and R$^{1'}$ is independently H, OH, optionally substituted alkyl including lower alkyl, azido, cyano, optionally substituted alkenyl or alkynyl, —C(O)O-(alkyl), —C(O)O(lower alkyl), —C(O)O-(alkenyl), —C(O)O-(alkynyl), —O(acyl), —O(lower acyl), —O(alkyl), —O(lower alkyl), —O(alkenyl), —O(alkynyl), halogen, halogenated alkyl, —NO$_2$, —NH$_2$, —NH(lower alkyl), —N(lower alkyl)$_2$, —NH(acyl), —N(acyl)$_2$, —C(O)NH$_2$, —C(O)NH(alkyl), —C(O)N(alkyl)$_2$, S(O)N-alkyl, S(O)N-alkenyl, S(O)N-alkynyl, SCH-halogen, wherein alkyl, alkenyl, and/or alkynyl maybe optionally substituted;

when X is O, S[O], NH, N-alkyl, N-alkenyl, N-alkynyl, S(O)N-alkyl, S(O)N-alkenyl, S(O)N-alkynyl, or SCH-halogen, then each R$^1$ and R$^{1'}$ is independently H, optionally substituted alkyl including lower alkyl, azido, cyano, optionally substituted alkenyl or alkynyl, —C(O)O-(alkyl), —C(O)O(lower alkyl), —C(O)O-(alkenyl), —C(O)O-(alkynyl), halogenated alkyl, —C(O)NH$_2$, —C(O)NH(alkyl), —C(O)N(alkyl)$_2$, —C(H)=N—NH$_2$, C(S)NH$_2$, C(S)NH(alkyl), or C(S)N(alkyl)$_2$, wherein alkyl, alkenyl, and/or alkynyl maybe optionally substituted;

when X* is CY$^3$;

then each R$^1$ is independently H, OH, optionally substituted alkyl including lower alkyl, azido, cyano, optionally substituted alkenyl or alkynyl, —C(O)O-(alkyl), —C(O)O(lower alkyl), —C(O)O-(alkenyl), —C(O)O-(alkynyl), —), —O(lower acyl), —O(alkyl), —O(lower alkyl), —O(alkenyl), —O(alkynyl), halogen, halogenated alkyl, —NO$_2$, —NH$_2$, —NH(lower alkyl), —N(lower alkyl)$_2$, —NH(acyl), —N(acyl)$_2$, —C(O)NH$_2$, —C(O)NH(alkyl), and —C(O)N(alkyl)$_2$, wherein an optional substitution on alkyl, alkenyl, and/or alkynyl may be one or more halogen, hydroxy, alkoxy or alkylthio groups taken in any combination; and Y$^3$ is hydrogen, alkyl, bromo, chloro, fluoro, iodo, azido, cyano, alkenyl, alkynyl, —C(O)O(alkyl), —C(O)O(lower alkyl), CF$_3$, —CONH$_2$, —CONH(alkyl), —CON(alkyl)$_2$;

each R$^2$ and R$^3$ independently is OH, NH$_2$, SH, F, Cl, Br, I, CN, NO$_2$, —C(O)NH$_2$, —C(O)NH(alkyl), —C(O)N(alkyl)$_2$, N$_3$, optionally substituted alkyl including lower alkyl, optionally substituted alkenyl or alkynyl, halogenated alkyl, —C(O)O-(alkyl), —C(O)O(lower alkyl), —C(O)O-(alkenyl), —C(O)O-(alkynyl), —O(acyl), —O(alkyl), —O(alkenyl), —O(alkynyl), —OC(O)NH$_2$, NC, C(O)OH, SCN, OCN, —S(alkyl), —S(alkenyl), —S(alkynyl), —NH(alkyl), —N(alkyl)$_2$, —NH(alkenyl), —NH(alkynyl), an amino acid residue or derivative, a prodrug or leaving group that provides OH in vivo, or an optionally substituted 3-7 membered heterocyclic ring having O, S and/or N independently as a heteroatom taken alone or in combination;

each R$^{2'}$ and R$^{3'}$ independently is H; optionally substituted alkyl, alkenyl, or alkynyl; —C(O)O(alkyl), —C(O)O(lower alkyl), —C(O)O(alkenyl), —C(O)O(alkynyl), —C(O)NH$_2$, —C(O)NH(alkyl), —C(O)N(alkyl)$_2$, —O(acyl), —O(lower acyl), —O(alkyl), —O(lower alkyl), —O(alkenyl), halogen, halogenated alkyl and particularly CF$_3$, azido, cyano, NO$_2$, —S(alkyl), —S(alkenyl), —S(alkynyl), NH$_2$, —NH(alkyl), —N(alkyl)$_2$, —), —NH(alkynyl), —NH(acyl), or —N(acyl)$_2$, and R$_3$ at 3'-C may also be OH;

Base is selected from the group consisting of:

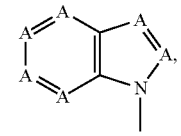

(A)

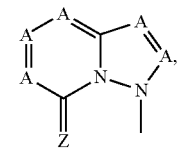

(B)

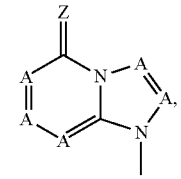

(C)

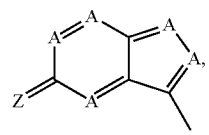

(D)

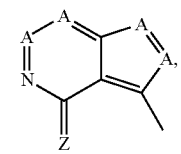

(E)

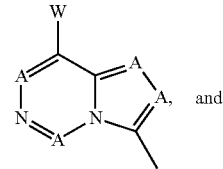

(F)

and

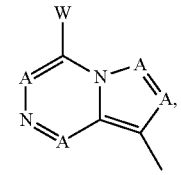

(G)

wherein each A independently is N or C—R$^5$;

W is H, OH, —O(acyl), —O(C$_{1-4}$ alkyl), —O(alkenyl), —O(alkynyl), —OC(O)R$^4$R$^4$R$^4$, —OC(O)NR$^4$R$^4$, SH, —S(acyl), —S(C$_{1-4}$ alkyl), NH$_2$, NH(acyl), N(acyl)$_2$, NH(C$_{1-4}$ alkyl), N(C$_{1-4}$ alkyl)$_2$, —N(cycloalkyl) C$_{1-4}$ alkylamino, di(C$_{1-4}$ alkyl)amino, C$_{3-6}$ cycloalkylamino, halogen, C$_{1-4}$ alkyl, C$_{1-4}$ alkoxy, CN, SCN, OCN, SH, N$_3$, NO$_2$, NH=NH$_2$, N$_3$, NHOH, —C(O)NH$_2$, —C(O)NH(acyl), —C(O)N(acyl)$_2$, —C(O)NH(C$_{1-4}$ alkyl), —C(O)N(C$_{1-4}$ alkyl)$_2$, —C(O)N(alkyl)(acyl), or halogenated alkyl;

Z is O, S, NH, N—OH, N—NH$_2$, NH(alkyl), N(alkyl)$_2$, N-cycloalkyl, alkoxy, CN, SCN, OCN, SH, NO$_2$, NH$_2$, N$_3$, NH=NH, NH(alkyl), N(alkyl)$_2$, CONH$_2$, CONH(alkyl), or CON(alkyl)$_2$, each R$^4$ is independently H, acyl, or C$_{1-6}$ alkyl;

each $R^5$ is independently H, Cl, Br, F, I, CN, OH, optionally substituted alkyl, alkenyl or alkynyl, carboxy, C(=NH)NH$_2$, C$_{1-4}$ alkoxy, C$_{1-4}$ alkyloxycarbonyl, N$_3$, NH$_2$, NH(alkyl), N(alkyl)$_2$, NO$_2$, N$_3$, halogenated alkyl especially CF$_3$, C$_{1-4}$ alkylamino, di(C$_{1-4}$ alkyl)amino, C$_{3-6}$ cycloalkylamino, C$_{1-6}$ alkoxy, SH, —S(C$_{1-4}$ alkyl), —S(C$_{1-4}$ alkenyl), —S(C$_{1-4}$ alkynyl), C$_{1-6}$ alkylthio, C$_{1-6}$ alkylsulfonyl, (C$_{1-4}$ alkyl)$_{0-2}$ aminomethyl, C$_{3-6}$ cycloalkylamino-alkenyl, -alkynyl, —(O)alkyl, —(O)alkenyl, —(O)alkynyl, —(O)acyl, —O(C$_{1-4}$ alkyl), —O(C$_{1-4}$ alkenyl), —O(C$_{1-4}$ alkynyl), —O—C(O)NH$_2$, —OC(O)N(alkyl), —OC(O)R'R'', —C(O)OH, C(O)O-alkyl, C(O)O-alkenyl, C(O)O-alkynyl, S-alkyl, S-acyl, S-alkenyl, S-alkynyl, SCN, OCN, NC, —C(O)—NH$_2$, C(O)NH(alkyl), C(O)N(alkyl)$_2$, C(O)NH(acyl), C(O)N(acyl)$_2$, (S)—NH$_2$, NH-alkyl, N(dialkyl)$_2$, NH-acyl, N-diacyl, or a 3-7 membered heterocycle having O, S, or N taken independently in any combination;

each R' and R'' independently is H, C$_{1-6}$ alkyl, C$_{2-6}$ alkenyl, C$_{2-6}$ alkynyl, halogen, halogenated alkyl, OH, CN, N$_3$, carboxy, C$_{1-4}$ alkoxycarbonyl, NH$_2$, C$_{1-4}$ alkylamino, di(C$_{1-4}$ alkyl)amino, C$_{1-6}$ alkoxy, C$_{1-6}$ alkylsulfonyl, or (C$_{1-4}$ alkyl)$_{0-2}$ aminomethyl; and all tautomeric, enantiomeric and stereoisomeric forms thereof;

with the caveat that when X is S in Formula (I), then the compound is not 5-(4-amino-imidazo[4,5-d][1,2,3]triazin-7-yl)-2-hydroxymethyl-tetrahydro-thiophen-3-ol or 7-(4-hydroxy-5-hydroxy-methyl-tetrahydro-thiophen-2-yl)-3,7-dihydro-imidazo[4,5-d][1,2,3]triazin-4-one, can be prepared according to Schemes 1, 2 or 7 below.

Modification from the Lactone

The key starting material for this process is an appropriately substituted lactone. The lactone may be purchased or can be prepared by any known means including standard epimerization, substitution and cyclization techniques. The lactone optionally can be protected with a suitable protecting group, preferably with an acyl or silyl group, by methods well known to those skilled in the art, as taught by Greene et al., *Protective Groups in Organic Synthesis*, John Wiley and Sons, Second Edition, 1991. The protected lactone can then be coupled with a suitable coupling agent, such as an organometallic carbon nucleophile like a Grignard reagent, an organolithium, lithium dialkylcopper or $R^6$—SiMe$_3$ in TAF with the appropriate non-protic solvent at a suitable temperature, to give the 1'-alkylated sugar.

The optionally activated sugar can then be coupled to the base by methods well known to those skilled in the art, as taught by Townsend, *Chemistry of Nuceleotides*, Plenum Press, 1994. For example, an acylated sugar can be coupled to a silylated base with a Lewis acid such as tin tetrachloride, titanium tetrachloride, or trimethylsilyltriflate in the appropriate solvent at a suitable temperature.

Subsequently, the nucleoside can be deprotected by methods well known to those skilled in the art, as taught by Greene et al., *Protective Groups in Organic Synthesis*, John Wiley and Sons, Second Edition, 1991.

In a particular embodiment, the 1'-C-branched ribonucleoside is desired. The synthesis of a ribonucleoside is shown in Scheme 1. Alternatively, deoxyribonucleoside is desired. To obtain these nucleosides, the formed ribonucleoside an optionally be protected by methods well known to those skilled in the art, as taught by Greene et al., *Protective Groups in Organic Synthesis*, John Wiley and Sons, Second Edition, 1991, and then the 2'-OH can be reduced with a suitable reducing agent. Optionally, the 2'-OH can be activated to facilitate reduction as, for example, via the Barton reduction.

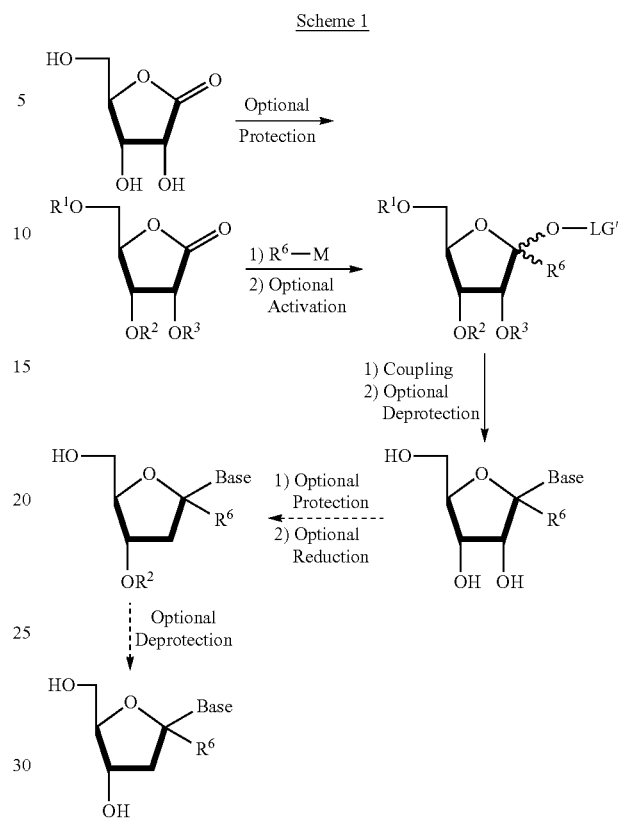

Scheme 1

Alternative Method for the Preparation of 1'-C-Branched Nucleosides

The key starting material for this process is an appropriately substituted hexose. The hexose can be purchased or can be prepared by any known means including standard epimerization (as, for example, via alkaline treatment), substitution and coupling techniques. The hexose can be protected selectively to give the appropriate hexafuranose, as taught by Townsend, *Chemistry of Nucleosides and Nucleotides*, Plenum Press, 1994.

The 1'-OH optionally can be activated to a suitable leaving group such as an acyl group or a halogen via acylation or halogenation, respectively. The optionally activated sugar can then be coupled to the base by methods well known to those skilled in the art, as taught by Townsend, *Chemistry of Nucleosides and Nucleotides*, Plenum Press, 1994. For example, an acylated sugar can be coupled to a silylated base with a Lewis acid, such as tin tetrachloride, titanium tetrachloride, or trimethylsilyltriflate in an appropriate solvent at a suitable temperature. Alternatively, a halo-sugar can be coupled to a silylated base in the presence of trimethylsilyltriflate.

The 1'-CH$_2$—OH, if protected, selectively can be deprotected by methods well known in the art. The resultant primary hydroxyl can be reduced to give the methyl, using a suitable reducing agent. Alternatively, the hydroxyl can be activated prior to reduction to facilitate the reaction, i.e., via the Barton reduction. In an alternate embodiment, the primary hydroxyl can be oxidized to the aldehyde, then coupled with a carbon nucleophile such as a Grignard reagent, an organolithium, lithium dialkylcopper or $R^6$—SiMe$_3$ in TAF with an appropriate non-protic solvent at a suitable temperature.

In a particular embodiment, the 1'-C-branched ribonucleoside is desired. The synthesis of a ribonucleoside is shown in Scheme 2. Alternatively, deoxyribonucleoside is desired. To obtain these nucleosides, the formed ribonucleoside optionally can be protected by methods well known to those skilled in the art, as taught by Greene et al., *Protective Groups in Organic Synthesis*, John Wiley and Sons, Second Edition, 1991, and then the 2'-OH can be reduced with a suitable reducing agent. Optionally, the 2'-OH can be activated to facilitate reduction as, for example, via the Barton reduction.

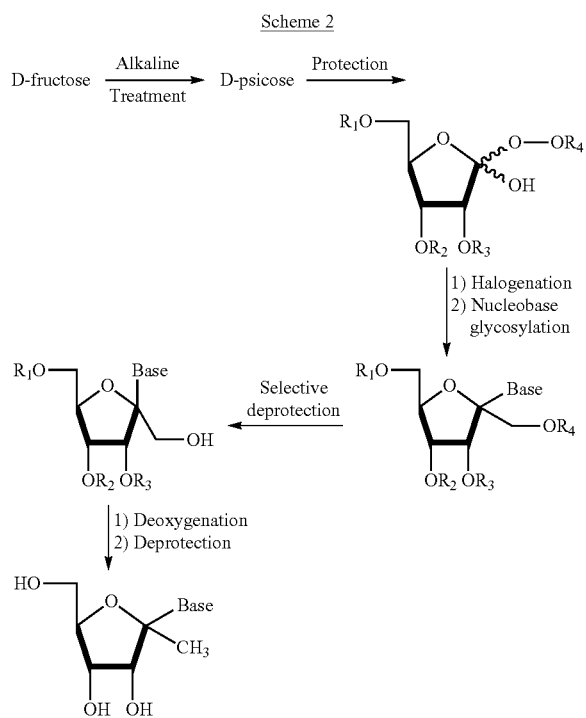

Scheme 2

In addition, the L-enantiomers corresponding to the compounds of the invention can be prepared following the same general methods (1 or 2), beginning with the corresponding L-sugar or nucleoside L-enantiomer as the starting material.

General Synthesis of 2'-C-Branched Nucleosides

2'-C-branched ribonucleosides of the following structures:

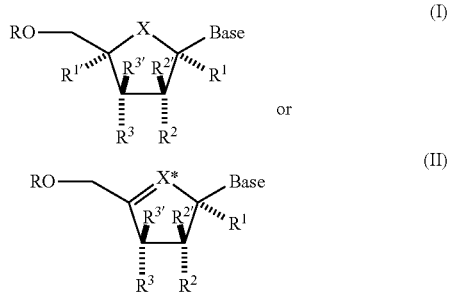

wherein R, $R^1$, $R^{1'}$, $R^2$, $R^{2'}$, $R^3$, $R^{3'}$, X, X*, and Base are all described above, can be prepared according to Schemes 3 or 4 below.

Glycosylation of the Nucleobase with an Appropriately Modified Sugar

The key starting material for this process is an appropriately substituted sugar with a 2'-OH and 2'-H, with an appropriate leaving group (LG), such as an acyl or halogen group, for example. The sugar can be purchased or can be prepared by any known means including standard epimerization, substitution, oxidation and/or reduction techniques. The substituted sugar can then be oxidized with an appropriate oxidizing agent in a compatible solvent at a suitable temperature to yield the 2'-modified sugar. Possible oxidizing agents are Jones' reagent (a mixture of chromic and sulfuric acids), Collins' reagent (dipyridine Cr(VI)oxide), Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molydate, $NarO_2$-CAN, NaOCl in HOAc, copper chromate, copper oxide, Raney nickel, palladium acetate, Meerwin-Pondorf-Verley reagent (aluminum t-butoxide with another ketone) and N-bromosuccinimide.

Then coupling of an organometallic carbon nucleophile such as a Grignard reagent, an organolithium, lithium dialkylcopper or $R^6$—$SiMe_3$ in TAF with the ketone and an appropriate non-protic solvent at a suitable temperature, yields the 2'-alkylated sugar. The alkylated sugar optionally can be protected with a suitable protecting group, preferably with an acyl or silyl group, by methods well known to those skilled in the art, as taught by Greene et al., *Protective Groups in Organic Synthesis*, John Wiley and Sons, Second Edition, 1991.

The optionally protected sugar can then be coupled to the base by methods well known to those skilled in the art, as taught by Townsend, *Chemistry of Nucleosides and Nucleotides*, Plenum Press, 1994. For example, an acylated sugar can be coupled to a silylated base with a Lewis acid, such as tin tetrachloride, titanium tetrachloride, or trimethylsilyltriflate in an appropriate solvent at a suitable temperature. Alternatively, a halo-sugar can be coupled to a silylated base in the presence of trimethylsilyltriflate.

Subsequently, the nucleoside can be deprotected by methods well known to those skilled in the art, as by Greene et al., *Protective Groups in Organic Synthesis*, John Wiley and Sons, Second Edition, 1991.

In a particular embodiment, the 2'-C-branched ribonucleoside is desired, the synthesis of which is shown in Scheme 3. Alternatively, a deoxyribonucleoside is desired. To obtain these nucleosides, the formed ribonucleoside can optionally be protected by methods well known to those skilled in the art, as by Greene et al., *Protective Groups in Organic Synthesis*, John Wiley and Sons, Second Edition, 1991, and then the 2'-OH can be reduced with a suitable reducing agent. Optionally, the 2'-OH can be activated to facilitate reduction, such as, for example, by the Barton reduction.

Scheme 3

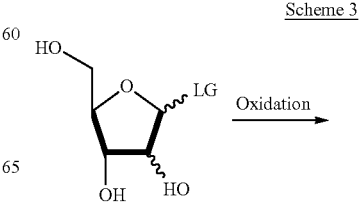

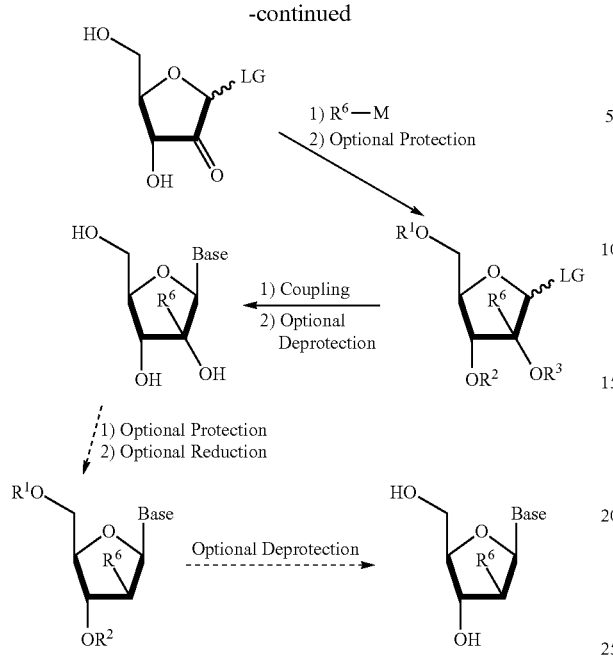

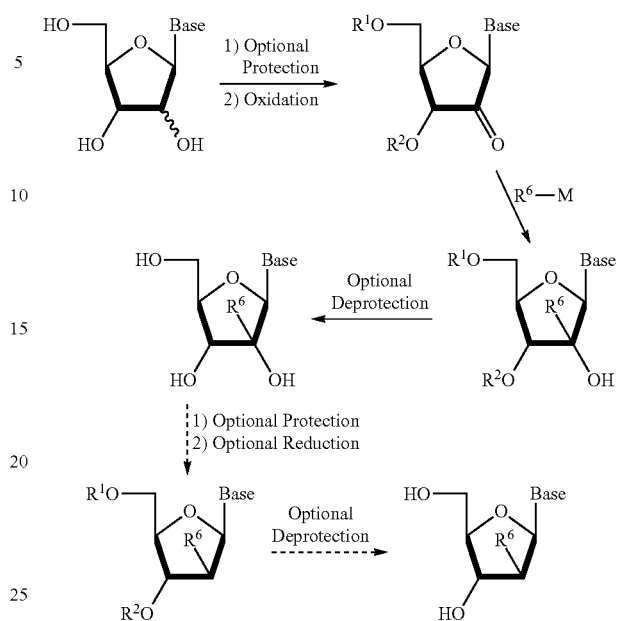

Modification of a Pre-Formed Nucleoside

The key starting material for this process is an appropriately substituted nucleoside with a 2'-OH and 2'-H. The nucleoside can be purchased or can be prepared by any known means including standard coupling techniques. The nucleoside optionally can be protected with suitable protecting groups, preferably with acyl or silyl groups, by methods well known to those skilled in the art, as described in Greene et al., *Protective Groups in Organic Synthesis*, John Wiley and Sons, Second Edition, 1991.

The appropriately protected nucleoside then can be oxidized with an appropriate oxidizing agent in a compatible solvent at a suitable temperature to yield the 2'-modified sugar. Possible oxidizing agents include Jones' reagent (a mixture of chromic and sulfuric acids), Collins' reagent (dipyridine Cr(VI)oxide), Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molydate, $NarO_2$-CAN, NaOCl in HOAc, copper chromate, copper oxide, Raney nickel, palladium acetate, Meerwin-Pondorf-Verley reagent (aluminum t-butoxide with another ketone) and N-bromosuccinimide.

Subsequently, the nucleoside can be deprotected by methods well known to those skilled in the art, as by Greene et al., *Protective Groups in Organic Synthesis*, John Wiley and Sons, Second Edition, 1991.

In a particular embodiment, a 2'-C-branched ribonucleoside is desired, the synthesis of which is shown in Scheme 4. Alternatively, the deoxyribonucleoside may be desired. To obtain these nucleosides, the formed ribonucleoside optionally may be protected by methods well known to those skilled in the art, as by Greene et al., *Protective Groups in Organic Synthesis*, John Wiley and Sons, Second Edition, 1991, and then the 2'-OH can be reduced with a suitable reducing agent. Optionally, the 2'-OH can be activated to facilitate reduction such as, for example, by the Barton reduction.

In another embodiment of the invention, the L-enantiomers are desired. These L-enantiomers corresponding to the compounds of the invention may be prepared following the same general methods given above, but beginning with the corresponding L-sugar or nucleoside L-enantiomer as the starting material.

C. General Synthesis of 3'-C-Branched Nucleosides

3'-C-branched ribonucleosides of the following structures:

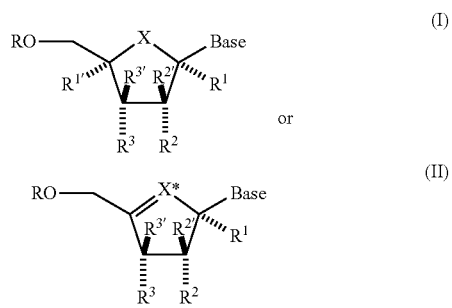

wherein R, $R^1$, $R^{1'}$, $R^2$, $R^{2'}$, $R^3$, $R^{3'}$, X, X*, and Base are all as described above, can be prepared according to Schemes 5 or 6 below.

Glycosylation of the Nucleobase with an Appropriately Modified Sugar (Scheme 5)

The key starting material for this process is an appropriately substituted sugar with a 3'-OH and a 3'-H, with an appropriate leaving group (LG) such as, for example, an acyl group or a halogen. The sugar can be purchased or can be prepared by any known means including standard epimerization, substitution, oxidation and/or reduction techniques. The substituted sugar then can be oxidized by an appropriate oxidizing agent in a compatible solvent at a suitable temperature to yield the 3'-modified sugar.

Possible oxidizing agents include Jones' reagent (a mixture of chromic and sulfuric acids), Collins' reagent (dipyridine Cr(VI)oxide), Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molydate, $NarO_2$-CAN, NaOCl in HOAc, copper chromate, copper oxide, Raney nickel, palladium acetate, Meerwin-Pondorf-Verley reagent (aluminum t-butoxide with another ketone) and N-bromosuccinimide.

Then coupling of an organometallic carbon nucleophile such as a Grignard reagent, an organolithium, lithium dialkylcopper or $R^6$—$SiMe_3$ in TAF with the ketone and an appropriate non-protic solvent at a suitable temperature, yields the 3'-C-branched sugar. The 3'-C-branched sugar optionally can be protected with a suitable protecting group, preferably with an acyl or silyl group, by methods well known to those skilled in the art, as taught by Greene et al., *Protective Groups in Organic Synthesis*, John Wiley and Sons, Second Edition, 1991.

The optionally protected sugar can then be coupled to the base by methods well known to those skilled in the art, as taught in Townsend, *Chemistry of Nucleosides and Nucleotides*, Plenum Press, 1994. For example, an acylated sugar can be coupled to a silylated base with a Lewis acid, such as tin tetrachloride, titanium tetrachloride, or trimethylsilyltriflate in an appropriate solvent at a suitable temperature. Alternatively, a halo-sugar can be coupled to a silylated base in the presence of trimethylsilyltriflate.

Subsequently, the nucleoside can be deprotected by methods well known to those skilled in the art, as by Greene et al., *Protective Groups in Organic Synthesis*, John Wiley and Sons, Second Edition, 1991.

In a particular embodiment, the 3'-C-branched ribonucleoside is desired, the synthesis of which is shown in Scheme 5. Alternatively, a deoxyribonucleoside is desired. To obtain these nucleosides, the formed ribonucleoside can optionally be protected by methods well known to those skilled in the art, as by Greene et al., *Protective Groups in Organic Synthesis*, John Wiley and Sons, Second Edition, 1991, and then the 2'-OH can be reduced with a suitable reducing agent. Optionally, the 2'-OH can be activated to facilitate reduction, such as, for example, by the Barton reduction.

Scheme 5

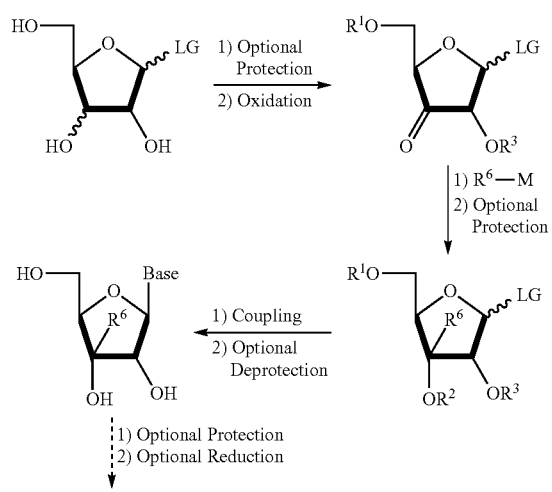

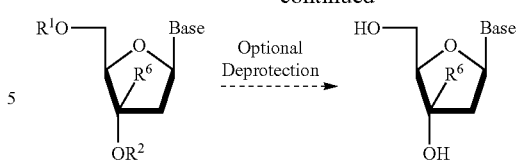

Modification of a Pre-Formed Nucleoside.

The key starting material for this process is an appropriately substituted nucleoside with a 3'-OH and 3'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al., *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents include Jones' reagent (a mixture of chromic and sulfuric acids), Collins' reagent (dipyridine Cr(VI)oxide), Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molydate, $NarO_2$-CAN, NaOCl in HOAc, copper chromate, copper oxide, Raney nickel, palladium acetate, Meerwin-Pondorf-Verley reagent (aluminum t-butoxide with another ketone) and N-bromosuccinimide.

Subsequently, the nucleoside can be deprotected by methods well known to those skilled in the art, as by Greene et al., *Protective Groups in Organic Synthesis*, John Wiley and Sons, Second Edition, 1991.

In a particular embodiment, the 3'-C-branched ribonucleoside is desired, the synthesis of which is shown in Scheme 6. Alternatively, a deoxyribonucleoside is desired. To obtain these nucleosides, the formed ribonucleoside can optionally be protected by methods well known to those skilled in the art, as by Greene et al., *Protective Groups in Organic Synthesis*, John Wiley and Sons, Second Edition, 1991, and then the 2'-OH can be reduced with a suitable reducing agent. Optionally, the 2'-OH can be activated to facilitate reduction, such as, for example, by the Barton reduction.

Scheme 6

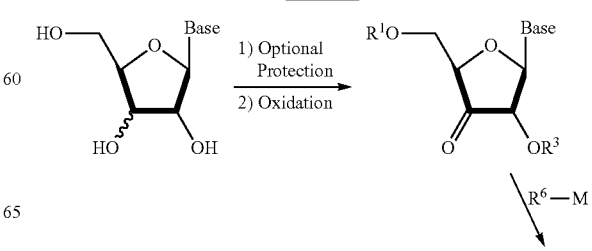

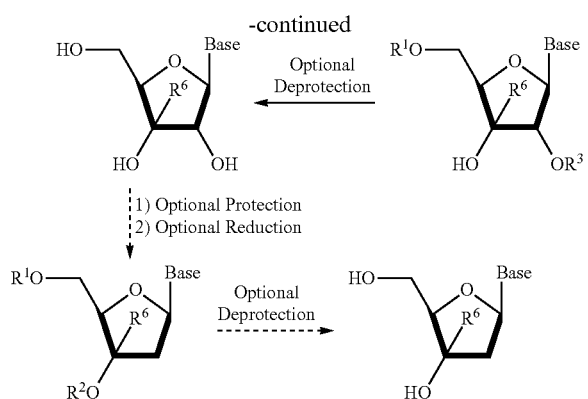

In another embodiment of the invention, the L-enantiomers are desired. These L-enantiomers corresponding to the compounds of the invention may be prepared following the same general methods given above, but beginning with the corresponding L-sugar or nucleoside L-enantiomer as the starting material.

General Synthesis of 4'-C-Branched Nucleosides

4'-C-branched ribonucleosides of the following structures:

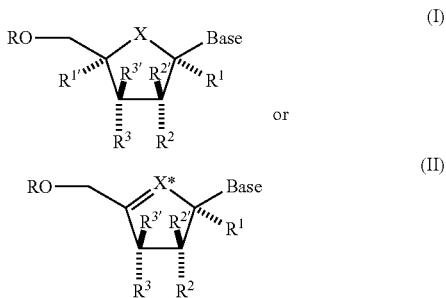

wherein R, R$^1$, R$^{1'}$, R$^2$, R$^{2'}$, R$^3$, R$^{3'}$, X, X*, and Base are all as described above, can be prepared according to the following general methods.

Modification from the Pentodialdo-Furanose.

The key starting material for this process is an appropriately substituted pentodialdo-furanose. The pentodialdo-furanose can be purchased or can be prepared by any known means including standard epimerization, substitution and cyclization techniques.

In a preferred embodiment, the pentodialdo-furanose is prepared from the appropriately substituted hexose. The hexose can be purchased or can be prepared by any known means including standard epimerization (for eg., via alkaline treatment), substitution, and coupling techniques. The hexose can be in either the furanose form or cyclized by any means known in the art, such as methodology taught by Townsend in *Chemistry of Nucleosides and Nucleotides*, Plenum Press, 1994, preferably by selectively protecting the hexose, to give the appropriate hexafuranose.

The 4'-hydroxymethylene of the hexafuranose then can be oxidized with an appropriate oxidizing agent in a compatible solvent at a suitable temperature to yield the 4'-aldo-modified sugar. Possible oxidizing agents are Swern reagents, Jones' reagent (a mixture of chromic and sulfuric acids), Collins' reagent (dipyridine Cr(VI)oxide), Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NarO_2$-CAN, NaOCl in HOAc, copper chromate, copper oxide, Raney nickel, palladium acetate, Meerwin-Pondorf-Verley reagent (aluminum t-butoxide with another ketone) and N-bromosuccinimide, although using $H_3PO_4$, DMSO and DCC in a mixture of benzene/pyridine at room temperature is preferred.

Then the pentodialdo-furanose optionally can be protected with a suitable protecting group, preferably with an acyl or silyl group, by methods well known to those skilled in the art, as taught by Greene et al., *Protective Groups in Organic Synthesis*, John Wiley and Sons, Second Edition, 1991. In the presence of a base, such as sodium hydroxide, the protected pentodialdo-furanose then can be coupled with a suitable electrophilic alkyl, halogeno-alkyl (such as $CF_3$), alkenyl or alkynyl (i.e., allyl), to obtain the 4'-alkylated sugar. Alternatively, the protected pentodialdo-furanose can be coupled with a corresponding carbonyl, such as formaldehyde, in the presence of a base like sodium hydroxide and with an appropriate polar solvent like dioxane, at a suitable temperature, and then reduced with an appropriate reducing agent to provide the 4'-alkylated sugar. In one embodiment, the reduction is carried out using PhOC(S)Cl and DMAP in acetonitrile at room temperature, followed by reflux treatment with ACCN and TMSS in toluene.

The optionally activated sugar can be coupled to the base by methods well known to those skilled in the art, as taught by Townsend in *Chemistry of Nucleosides and Nucleotides*, Plenum Press, 1994. For example, an acylated sugar can be coupled to a silylated base with a Lewis acid, such as tin tetrachloride, titanium tetrachloride, or trimethylsilyltriflate in an appropriate solvent at room temperature.

Subsequently, the nucleoside can be deprotected by methods well known to those skilled in the art, as by Greene et al., *Protective Groups in Organic Synthesis*, John Wiley and Sons, Second Edition, 1991.

In a particular embodiment, the 4'-C-branched ribonucleoside is desired. Alternatively, a deoxyribonucleoside is desired. To obtain these nucleosides, the formed ribonucleoside can optionally be protected by methods well known to those skilled in the art, as by Greene et al., *Protective Groups in Organic Synthesis*, John Wiley and Sons, Second Edition, 1991, and then the 2'-OH can be reduced with a suitable reducing agent. Optionally, the 2'-OH can be activated to facilitate reduction, such as, for example, by the Barton reduction.

In another embodiment of the invention, the L-enantiomers are desired. These L-enantiomers corresponding to the compounds of the invention may be prepared following the same general methods given above, but beginning with the corresponding L-sugar or nucleoside L-enantiomer as the starting material.

Methods for Ribofuranosyl-2-azapurine Synthesis

Preparation of 1'-C-methyl-ribofuranosyl-2-azapurine via 6-amino-9-(1-deoxy-beta-D-psicofuranosyl) purine As an alternative method of preparation, the title compound can be prepared according to the published procedure of Farkas and Sorm (J. Farkas and F. Sorm, "Nucleic acid components and their analogues. XCIV. Synthesis of 6-amino-9-(1-deoxy-beta-D-psicofuranosyl)purine," *Collect. Czech. Chem. Commun.*, 1967, 32:2663-7; and J. Farkas, *Collect. Czech. Chem. Commun.*, 1966, 31:1535 (Scheme 7).

In a similar manner, but using the appropriate sugar and 2-azapurine base corresponding to the desired product compound, a variety of Formula (I) and/or Formula (II) compounds can be prepared.

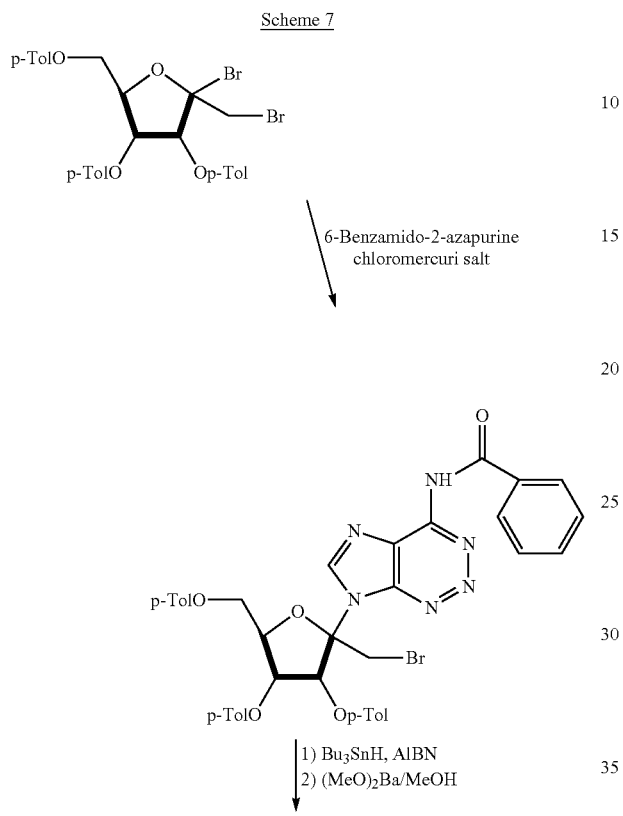

Alternative Methods for Ribofuranosyl-Purine Analogue Synthesis

Preparation of ribofuranosyl-purine analogues: 2-aza-3,7-dideazaadenosine derivative compounds Preparation of 2-aza-3,7-dideazaadenosine derivative compounds may be prepared according to the published synthesis of L. Towsend et al., *Bioorganic & Med. Chem. Letters*, 1991, 1(2):111-114, where the starting material, ethyl-3-cyanopyrrole-2-carboxylate 4 was synthesized by Huisgen & Laschtuvka, according to the procedure provided in *Chemische Berichte*, 1960, 93:65-81, as shown in Scheme 8:

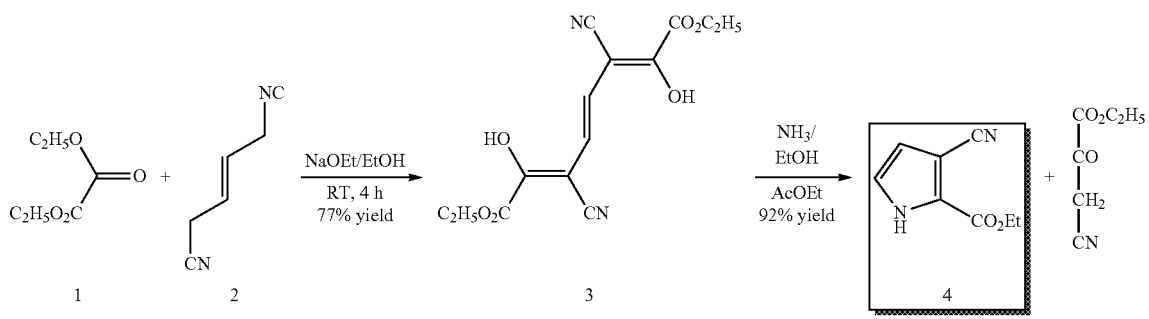

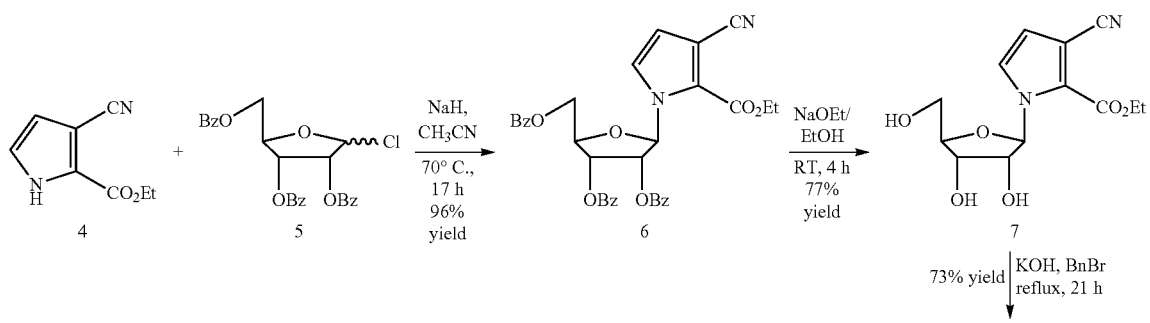

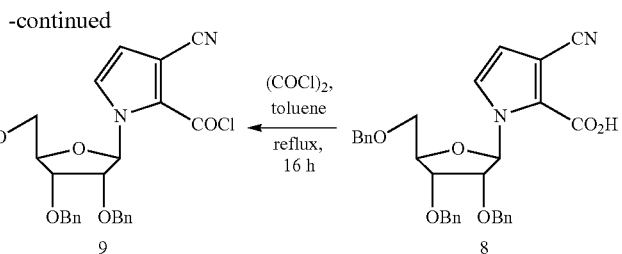
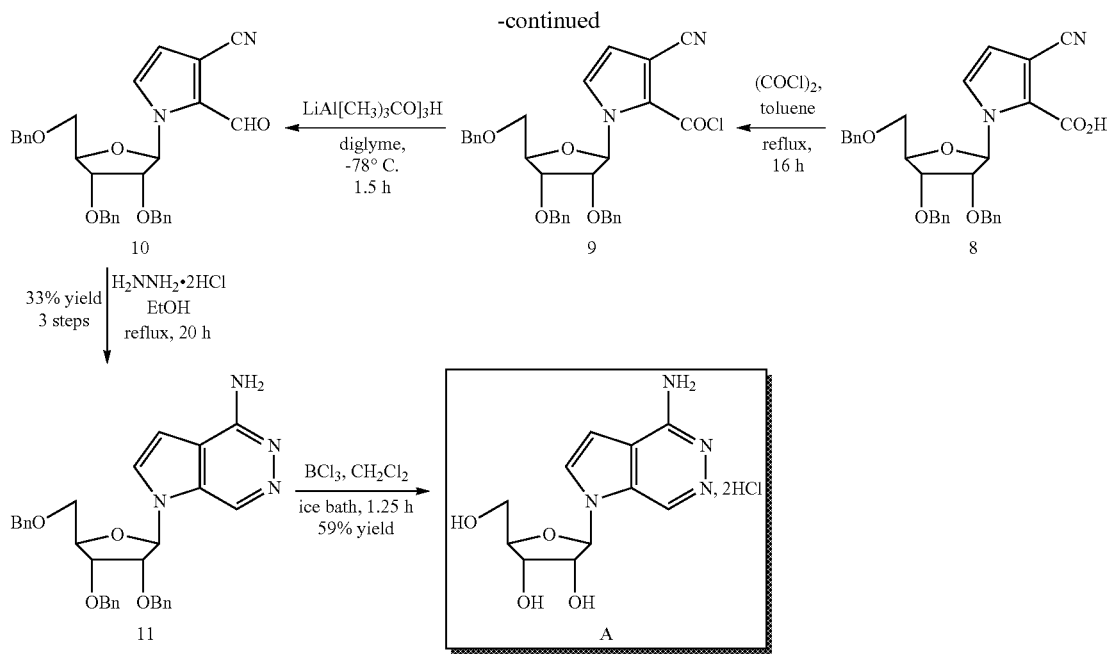
Preparation of ribofuranosyl-purine analogues: 2-aza-3-deazaadenosine derivative compounds
Preparation of 2-aza-3-deazaadenosine derivative compounds may be prepared according to the published synthesis of B. Otter et al., *J. Heterocyclic Chem.*, 1984, 481-89 shown in Scheme 9. The commercially available starting material used is the 4,5-dichloro-6-pyridazone 12.
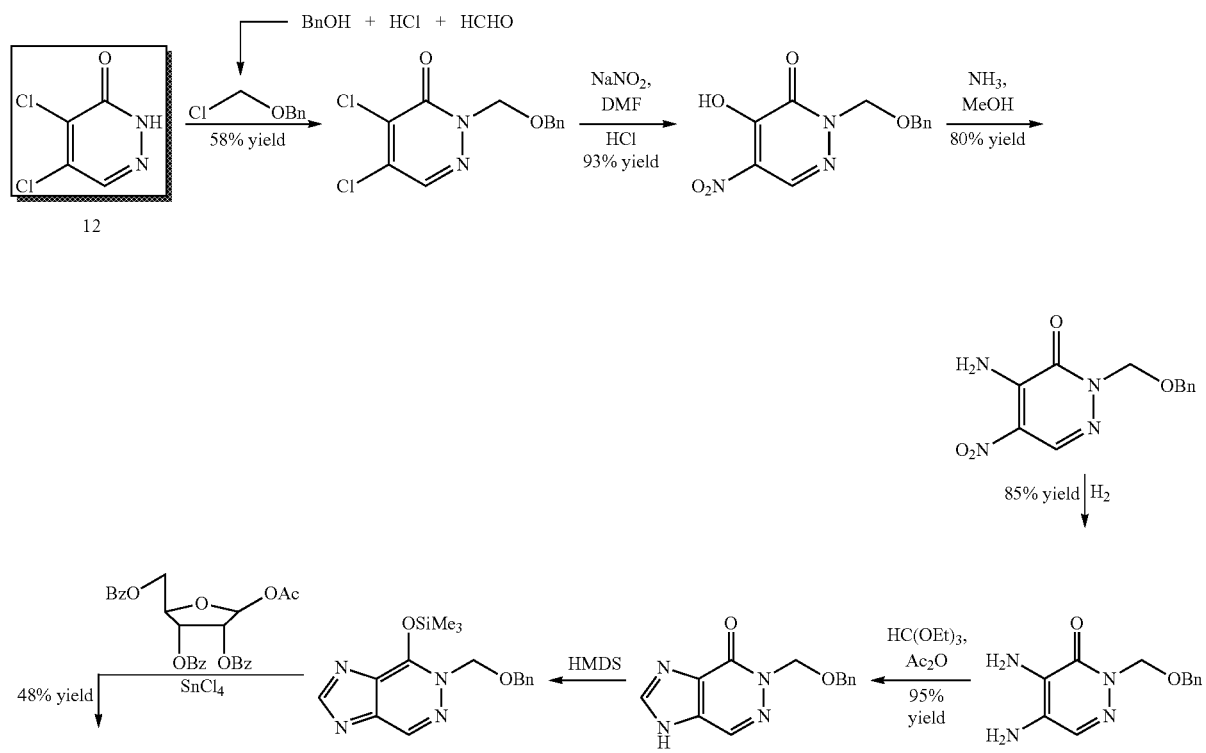

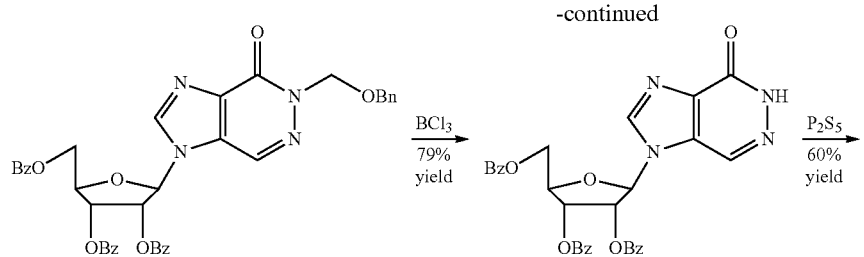
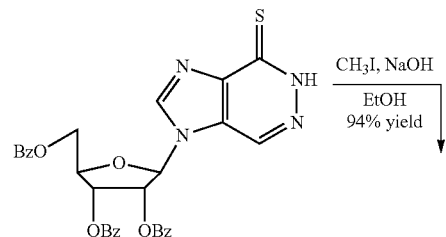
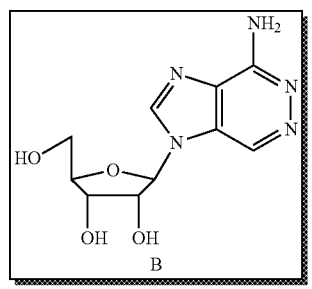
An alternative preparation of 2-aza-3-deazaadenosine derivative compounds that utilizes a chlorination step is that according to R. Panzica, *J. Chem. Soc. Perkin Trans I*, 1989, 1769-1774 and *J. Med. Chem.*, 1993, 4113-4120, shown in Scheme 10:
Scheme 10
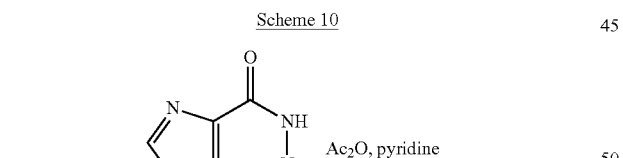
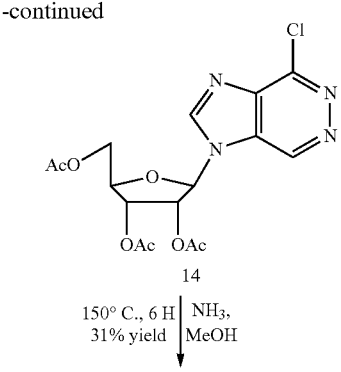
-continued
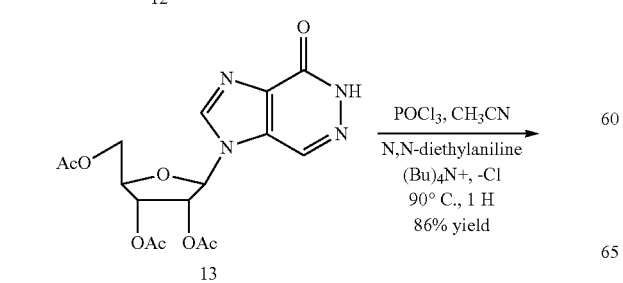

Preparation of purine analogues for nucleosides: optionally substituted 2,8-diaza-3,7-dideazaadenine derivative compounds Preparation of certain 2,8-diaza-3,7-dideazaadenosine derivative compounds may be prepared according to the published synthesis by Oda et al. in *J. Heterocyclic Chem.*, 1984, 21:1241-55 and *Chem. Pharm. Bull.*, 1984, 32(11):4437-46, as shown in Scheme 11. The starting material is commercially available 4,5-dichloro-6-pyridazone 12.

Scheme 11

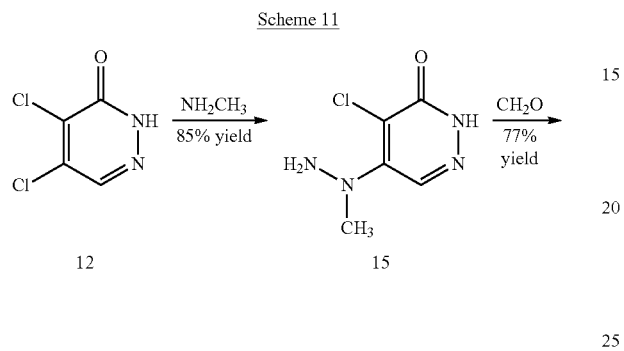

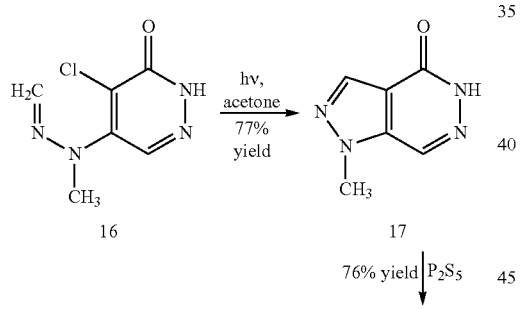

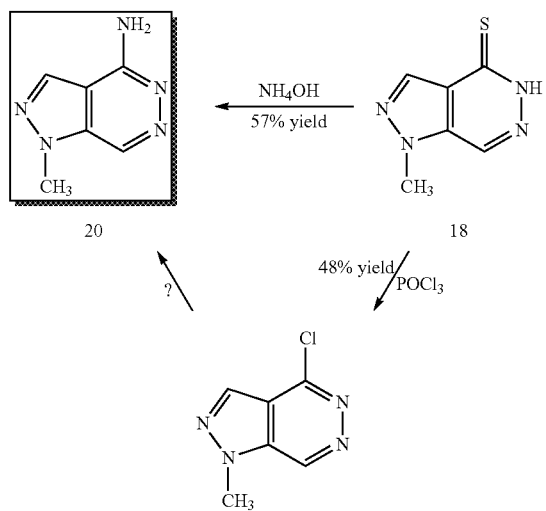

Preparation of purine analogues for nucleosides: 2,8-diaza-3-deazaadenosine derivative compounds Preparation of certain 2,8-diaza-3-deazaadenosine derivative compounds may be prepared according to the published synthesis by Panzica et al. in *J. Heterocyclic Chem.*, 1982, 285-88, *J. Med. Chem.*, 1993, 4113-20, and *Bioorg. & Med. Chem. Letters.*, 1996, 4(10):1725-31, as provided in Scheme 12. The key intermediate 27 was prepared via a 1,3-dipolar cycloaddition reaction between the 2,3,5-tri-O-benzoyl-β-D-ribofuranosyl azide 26 and methyl-hydroxy-2-butylnoate 25. A ribofuranosyl azide 26 synthesis was described by A. Stimac et al., *Carbohydrate Res.*, 1992, 232(2):359-65, using SnCl$_4$ catalyzed azidolysis of 1-O-Acetyl-2,3,5-tri-O-benzoyl-β-D-ribofuranose with Me$_3$SiN$_3$ in CH$_2$Cl$_2$ at room temperature.

Scheme 12

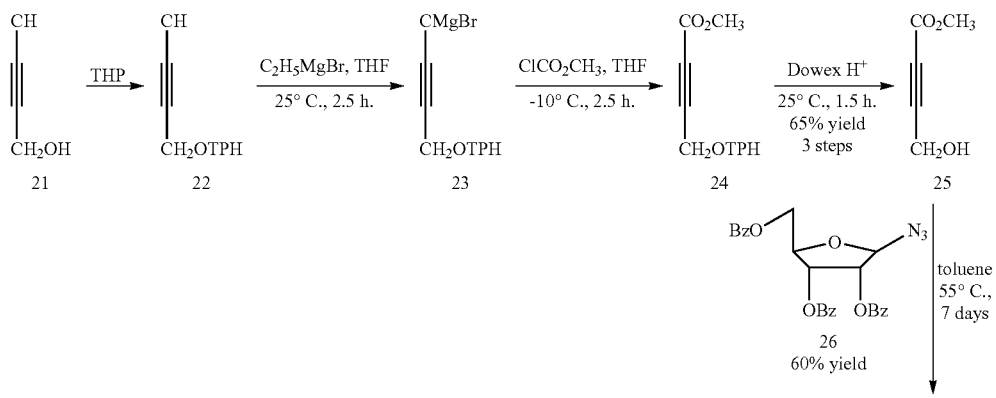

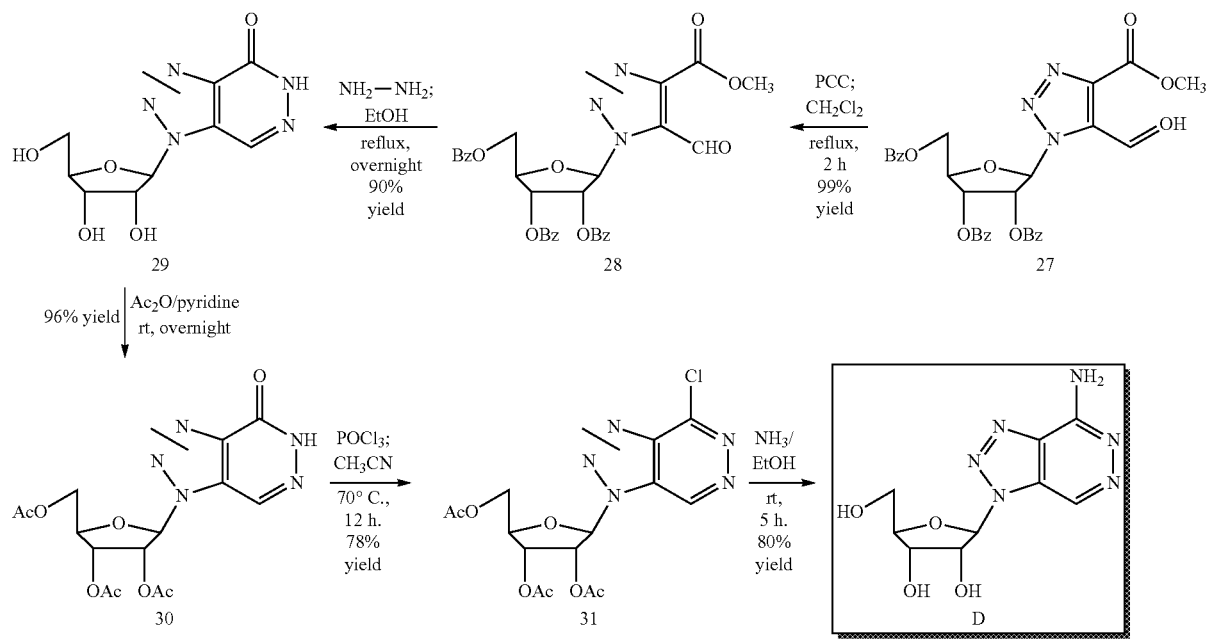

Preparation of purine analogues for nucleosides: alternative preparation of 2,8-diaza-3-deazaadenine derivative compounds 2,8-diaza-3-deazaadenine derivative compounds may be prepared (see Scheme 13) according to the published synthesis by Chen et al. in *J. Heterocyclic Chem.*, 1982, 285-88; however, no condensation of this compound with ribofuranose is found.

Preparation of ribofuranosyl-2-azapurines via use of protective groups

As an alternative method of preparation, the compounds of the present invention can also be prepared by synthetic methods well known to those skilled in the art of nucleoside and nucleotide chemistry, such as taught by Townsend in *Chemistry of Nucleosides and Nucleotides*, Plenum Press, 1994.

Scheme 13

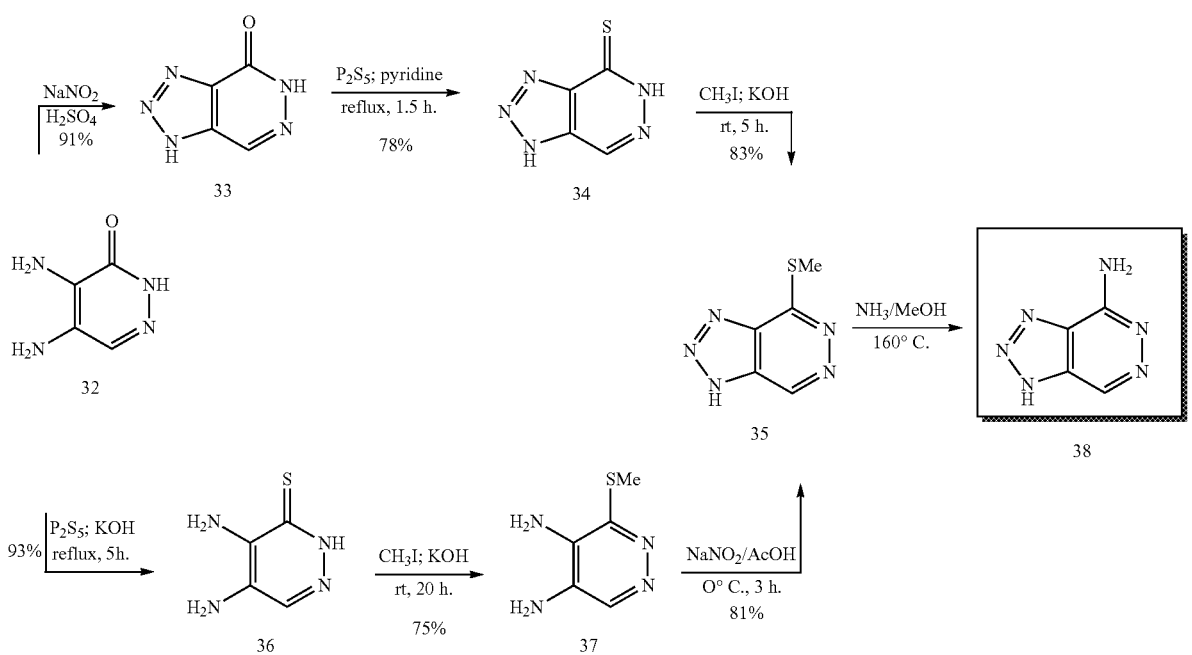

A representative general synthetic method is provided in Scheme 14. The starting material is a 3,5-is-O-protected beta-D-alkyl ribofuranoside, but it will be understood that any 2', 3', or 5'-position may carry a protecting group to shield it from reacting. The 2'-C—OH then is oxidized with a suitable oxidizing agent in a compatible solvent at a suitable temperature to yield the 2'-keto-modified sugar. Possible oxidizing agents are Swern reagents, Jones' reagent (a mixture of chromic and sulfuric acids), Collins' reagent (dipyridine Cr(VI)oxide), Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molydate, $NarO_2$-CAN, NaOCl in HOAc, copper chromate, copper oxide, Raney nickel, palladium acetate, Meerwin-Pondorf-Verley reagent (aluminum t-butoxide with another ketone) and N-bromosuccinimide.

The introduction of a "Z" substituent on any of base formulae (i)-(vi) optionally may be performed subsequent to the initial addition of protecting groups. For example, the introduction of an amino group for "Z" is accomplished by the addition of an appropriate amine in an appropriate solvent to the 2'-C-halo intermediate just prior to the last step of removal of the protecting groups. Appropriate amines include alcoholic or liquid ammonia to generate a primary amine (—$NH_2$), an alkylamine to generate a secondary amine (—NHR), or a dialkylamine to generate a tertiary amine (—NRR').

Finally, the nucleoside can be deprotected by methods well known to those skilled in the art, as by Greene et al., *Protective Groups in Organic Synthesis*, John Wiley and Sons, Second Edition, 1991. It is to be noted that this reaction scheme can be used for joining any of the purine nucleoside analogue bases provided for in Schemes 8-13 with a ribofuranosyl moiety.

Scheme 14

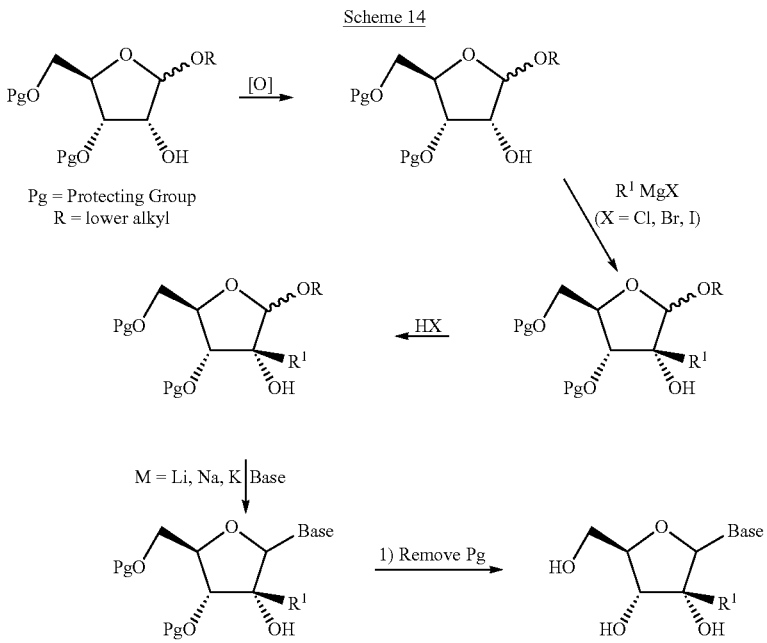

Next, addition of a Grignard reagent, such as, for example, an alkyl-, alkenyl- or alkynyl-magnesium halide like $CH_3MgBr$, $CH_3CH_2MgBr$, vinylMgBr, allylMgBr and ethynylMgBr, or an alkyl-, alkenyl- or alkynyl-lithium, such as $CH_3Li$, in a suitable organic solvent, such as, for example, diethyl ether or THF, across the double bond of the 2'-carbonyl group provides a tertiary alcohol at this position. The addition of a hydrogen halide in a suitable solvent, such as, for example, Hr in HOAc, in the subsequent step provides a leaving group (LG) such as, for example, a chloro, bromo or iodo, at the C-1 anomeric carbon of the sugar ring that later generates a nucleosidic linkage. Other suitable LGs include C-1 sulfonates such as, for example, methanesulfonate, trifluoromethanesulfonate and/or p-toluenesulfonate.

The introduction in the next step of a metal salt (Li, Na or K) of an appropriately substituted 2-azapurine in a suitable organic solvent such as, for example, THF, acetonitrile of DMF, results in the formation of the desired nucleosidic linkage and addition of the desired 2-azapurine base. This displacement reaction may be catalyzed by a phase transfer catalyst like TDA-1 or triethylbenzylammonium chloride.

The present invention is described by way of illustration in the following examples. It will be understood by one of ordinary skill in the art that these examples are in no way limiting and that variations of detail can be made without departing from the spirit and scope of the present invention.

EXAMPLES

The test compounds were dissolved in DMSO at an initial concentration of 200 µM and then were serially diluted in culture medium.

Unless otherwise stated, bay hamster kidney (HK-21) (ATCC CCL-10) and bos Taurus (T) (ATCC CRL 1390) cells were grown at 37° C. in a humidified $CO_2$ (5%) atmosphere. HK-21 cells were passaged in Eagle MEM additioned of 2 mM L-glutamine, 10% fetal ovine serum (FS, Gibco) and Earle's SS adjusted to contain 1.5 g/L sodium bicarbonate and 0.1 mM non-essential amino acids. T cells were passaged in Dulbecco's modified Eagle's medium with 4 mM L-glutamine and 10% horse serum (HS, Gibco), adjusted to contain 1.5 g/L sodium bicarbonate, 4.5 g/L glucose and 1.0 mM sodium pyruvate. The vaccine strain 17D (YFV-17D) (Stamaril®, Pasteur Merieux) and Bovine Viral Diarrhea virus (BVDV) (ATCC VR-534) were used to infect HK and T cells, respectively, in 75 cm² bottles. After a 3 day incubation period at 37° C., extensive cytopathic effect was observed. Cultures were freeze-thawed three times, cell debris were removed by centrifugation and the supernatant was aliquoted and stored at −70° C. YFV-17D and VDV were titrated in HK-21 and T cells, respectively, that were grown to confluency in 24-well plates.

The following examples are derived by selection of an appropriate, optionally substituted sugar or cyclopentane ring coupled with an optionally substituted 2-azapurine base, and prepared according to the following synthetic schemes:

Example 1: Synthesis of optionally substituted 1'-C-branched-ribofuranosyl, -sulfonyl, -thiophenyl or cyclopentanyl-2-azapurines;

Example 2: Synthesis of optionally substituted 2'-C-branched-ribofuranosyl, -sulfonyl, -thiophenyl or cyclopentanyl-2-azapurines;

Example 3: Synthesis of optionally substituted 3'-C-branched-ribofuranosyl, -sulfonyl, -thiophenyl or cyclopentanyl-2-azapurines;

Example 4: Synthesis of optionally substituted 4'-C-branched-ribofuranosyl, -sulfonyl, -thiophenyl or cyclopentanyl-2-azapurines;

Examples 5-13: Synthesis of specific compounds of the present invention; and

Examples 14-18: Biologic test results of representative examples of compounds of the present invention.

Example 1

1'-C-branched ribofuranosyl, -sulfonyl or cyclopentanyl-2-azapurine, optionally substituted The title compound is prepared according to Schemes 1, 2, or 7. In a similar manner but using the appropriate sugar or cyclopentane ring and optionally substituted 2-azapurine base, the following nucleosides of Formulae (I) or (II) may be prepared:

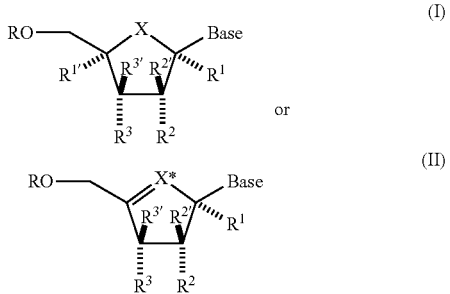

wherein: base may be any of the Formulae (A)-(G) as described herein where R in each instance may exist in mono-, di- or triphosphate form.

Alternatively, the Dimroth rearrangement may be used for making 2-azapurines from the corresponding purine base. In this reaction, an N-alkylated or N-arylated imino heterocycle undergoes rearrangement to its corresponding alkylamino or arylamino heterocycle.

Example 1a

1'-C-hydroxymethyl-2-azaadenosine

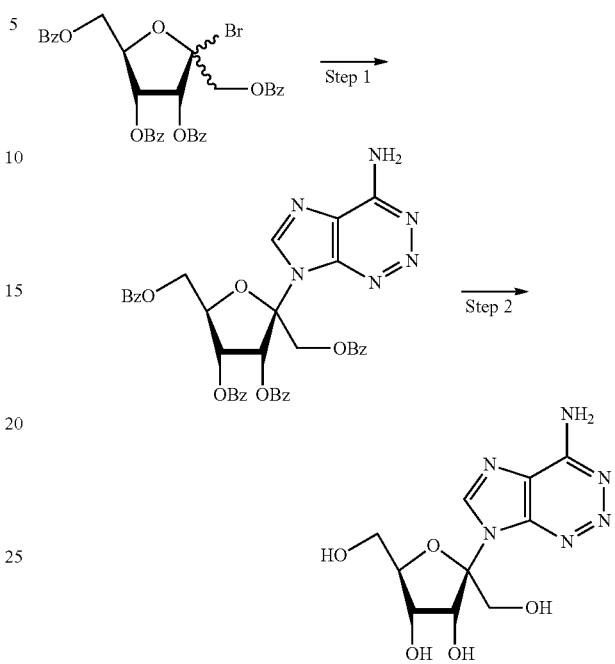

Step 1: 2-azaadenine, NaH, ACN, rt, 24 hrs; Step 2: MeONa/MeOH.

The starting material 2-azaadenine may be prepared starting from malonitrile by the synthesis taught by D. W. Wooley, *Journal of Biological Chemistry*, (1951), 189:401.

Example 2

2'-C-branched ribofuranosyl, -sulfonyl or cyclopentanyl-2-azapurine, optionally substituted The title compound is prepared according to Schemes 3, 4, or through protection of appropriately selected substituent groups in Schemes 7 or 8. In a similar manner but using the appropriate sugar or cyclopentane ring and optionally substituted 2-azapurine base, the following nucleosides of Formulae (I) or (II) may be prepared:

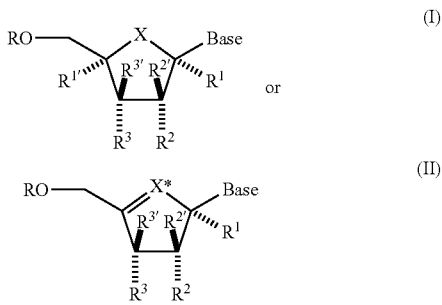

wherein: base may be any of the Formulae (A)-(G) as described herein where R in each instance may exist in mono-, di- or triphosphate form.

Alternatively, the Dimroth rearrangement may be used for making 2-azapurines from the corresponding purine base. In this reaction, an N-alkylated or N-arylated imino heterocycle undergoes rearrangement to its corresponding alkylamino or arylamino heterocycle.

Example 2a

2'-C-methyl-2-azaadenosine

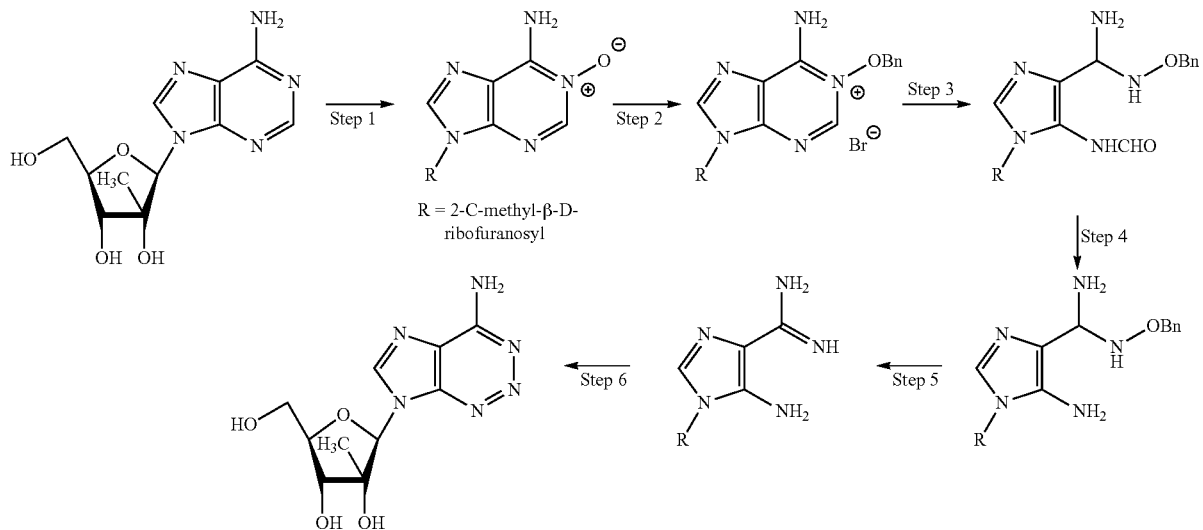

R = 2-C-methyl-β-D-ribofuranosyl (Synthesis according to the procedure of J. A. Montgomery, Nucleic Acid Chemistry, 1978, Part II, 681-685 starting with 2'-C-methyladenosine.)
Step 1: $H_2O_2$, AcOH, 80%; Step 2: BnBr, DMAc, Step 3: NaOH, $H_2O$, EtOH, 30%, Step 4: $NH_3$/MeOH, 80° C., 2 days, 60%; Step 5: $H_2$/Pd/C, 3 atm, MeOH, 30% Step 6: $NaNO_2$, AcOH, $H_2O$, 50%.

4-Amino-7-(2-C-methyl-β-D-ribofuranosyl)imidazo[4,5-d]-v-triazine (2'-C-methyl-2-azaadenosine)

$^1$H NMR (DMSO-$d_6$) δ 8.82 (s, 1H, H8), 7.97 (br, 2H, $NH_2$), 6.12 (s, 1H, H1'), 5.22-5.51 (m, 3H, 3OH), 3.70-4.17 (m, 4H, H3', H4', 2H5'), 0.80 (s, 3H, $CH_3$). $^{13}$C NMR (DMSO-$d_6$) δ 153, 146, 142, 116, 92, 83, 79, 72, 60, 20. m/z (FAB>0) 565 (2M+H)$^+$, 283 (M+H)$^+$, (FAB<0) 563 (2M−H)$^-$.

Alternatively, 2-azaadenosine shown as the final product in Example 2.a. may be prepared starting with adenosine, according to the procedure of J. A. Montgomery, *Nucleic Acid Chemistry*, 1978, Part II, 681-685 starting with 2'-C-methyladenosine, or via 2-azainosine in a synthetic procedure taught by R. P. Panzica, *Journal of Heterocyclic Chemistry*, 1972, 9:623-628 starting with AICA riboside.

Example 2b

2'-C-methyl-pyrrolo-4-amino-1,2,3-triazine

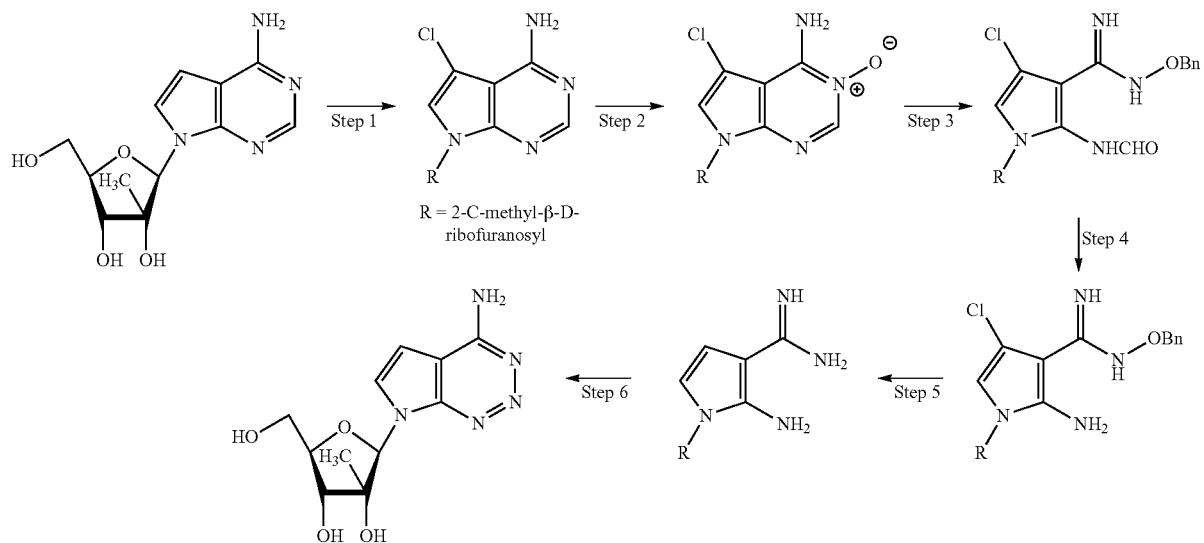

R = 2-C-methyl-β-D-ribofuranosyl

Step 1: NCS, DMF; Step 2: mcPBA, AcOH; Step 3: a) BnBr, DMAc; b) NaOH, H₂O, EtOH, Step 4: NH₃/MeOH, 80° C., Step 5: H₂/Pd/C, MeOH; Step 6: NaNO₂, AcOH, H₂O.

Example 3

3'-C-branched ribofuranosyl, -sulfonyl or cyclopentanyl-2-azapurine, optionally substituted The title compound is prepared according to Schemes 5, 6, or through protection of appropriately selected substituent groups in Scheme 8. In a similar manner but using the appropriate sugar or cyclopentane ring and optionally substituted 2-azapurine base, the following nucleosides of Formulae (I) and (II) may be prepared:

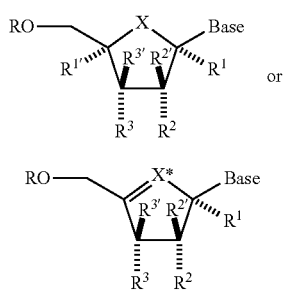

wherein: base may be any of the Formulae (A)-(G) as described herein where R in each instance may exist in mono-, di- or triphosphate form.

Alternatively, the Dimroth rearrangement may be used for making 2-azapurines from the corresponding purine base. In this reaction, an N-alkylated or N-arylated imino heterocycle undergoes rearrangement to its corresponding alkylamino or arylamino heterocycle.

Example 4

4'-C-branched ribofuranosyl, -sulfonyl or cyclopentanyl-2-azapurine, optionally substituted The title compound is prepared according to modification from the corresponding pentodialdo-furanose. In a similar manner but using the appropriate sugar or cyclopentane ring and optionally substituted 2-azapurine base, the following nucleosides of Formulae (I) or (II) may be prepared:

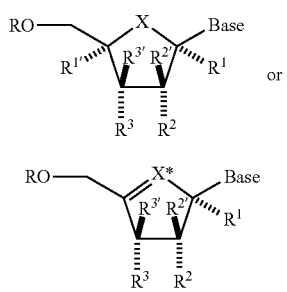

wherein: base may be any of the Formulae (A)-(G) as described herein where R in each instance may exist in mono-, di- or triphosphate form.

Alternatively, the Dimroth rearrangement may be used for making 2-azapurines from the corresponding purine base. In this reaction, an N-alkylated or N-arylated imino heterocycle undergoes rearrangement to its corresponding alkylamino or arylamino heterocycle.

Example 5

Synthesis of 4-amino-1-(β-D-ribofuranosyl)imidazo[4,5]pyridazine

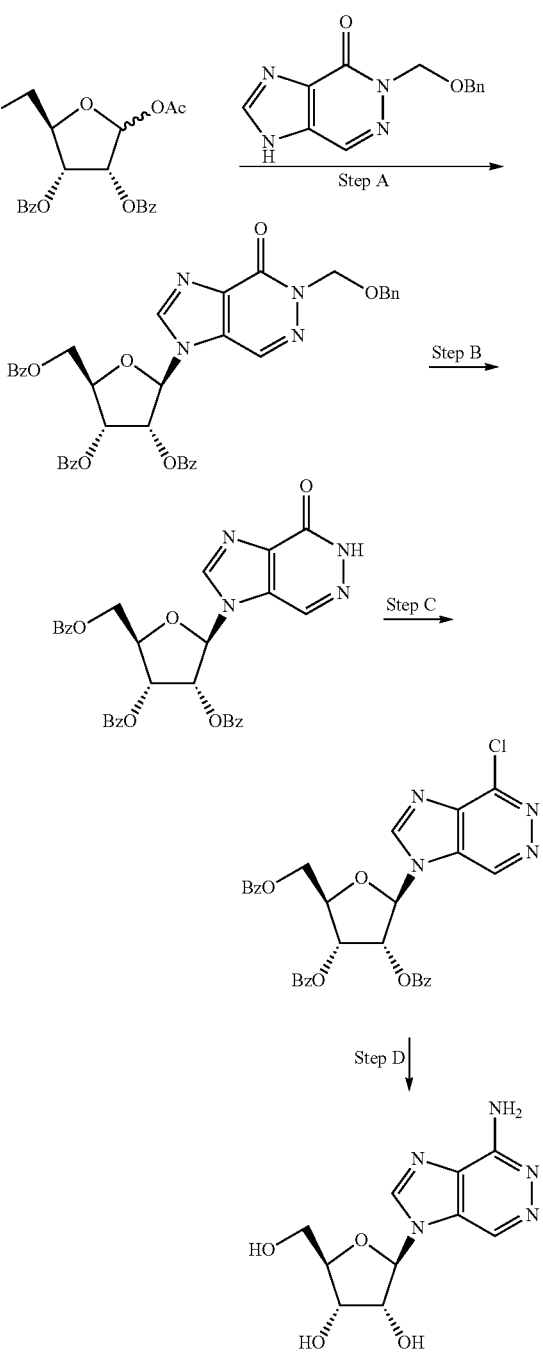

Step A: 1-(2,3,5-tri-O-Benzoyl-β-D-ribofuranosyl-5-benzyloxymethylimidazo[4,5-d]pyridazin-4-one The 5-benzyloxymethylimidazo[4,5-d]pyridazine (500 mg, 1.95 mmol) [for preparation see *Journal of Heterocyclic Chemistry*, 1984, Vol 21. 481] was heated at reflux in hexamethyldisilazane (6 mL) for 1 hour. The mixture was evaporated to dryness to give a slight yellow syrup which was dissolved in dry 1,2-dichloroethane (20 mL). The 1-O-acetyl-2,3,5-tri-O-benzoyl-β-ribofuranose (1.04 g, 2.06 mmol) and stannic chloride (0.4 mL, 3.44 mmol) were added at 20° C. and the mixture was stirred for 3 hours. The reaction mixture was poured into an aqueous solution of sodium hydrogenocarbonate, filtrated through a pad of celite and washed by dichloromethane. The organic layer was evaporated to dryness to give a yellow foam. The crude product was purified on silica gel using n-hexane/ethyl acetate (3/2) as eluant to give the title compound (703 mg) as a white powder.

$^1$H NMR (DMSO-$d_6$) δ ppm: 4.39 (s, 2H, $CH_2$), 4.60 (m, 2H), 4.73 (m, 1H), 5.34 (dd, 2H, $CH_2$), 5.77-5.88 (m, 2H, H2' and H3'), 6.56 (m, 1H, H1'), 6.98-7.10 (m, 5H), 7.23-7.32 (m, 6H), 7.41-7.51 (m, 3H), 7.68-7.73 (m, 2H), 7.74-7.8 (m, 4H), 8.51 (s, 1H), 8.52 (s, 1H).

Step B: 1-(2,3,5-tri-O-Benzoyl-β-D-ribofuranosyl)imidazo[4,5-d]pyridazin-4-one To a solution containing the compound from Step B (500 mg, 0.7 mmol), in dry dichloromethane (25 mL) was added a pre-cooled (−78° C.) solution of boron trichloride 1M (5 mL) at −78° C. and stirred for 2 hours at −78° C. A mixture of methanol/dichloromethane (1/1) was added to the mixture at −78° C. and then at 20° C. The reaction mixture was evaporated to dryness to give a yellow powder. The crude product was purified on silica gel using n-hexane/ethyl acetate (3/2) as eluant to give the title compound (400 mg) as a yellow powder.

$^1$H NMR (DMSO-$d_6$) δ ppm: 4.77-4.98 (m, 3H, H4', 2H5'), 5.95-6.12 (m, 2H, H2' and H3'), 6.65 (m, 1H, H1'), 7.39-7.76 (m, 9H), 7.84-8.06 (m, 6H), 8.64-5.79 (m, 2H, H3 and H8), 12.84 (br, 1H, NH).

Mass spectrum: m/z (FAB>0) 581 (M+H)$^+$, (FAB<0) 579 (M−H)$^−$

Step C: 4-chloro-1-(2,3,5-tri-O-Benzoyl-β-D-ribofuranosyl)imidazo[4,5-d]pyridazine A solution containing the compound from Step B (1.32 g, 2.27 mmol), the N,N-diethylaniline (365 μL), tetrabutylammonium chloride (1.2 g), freshly distilled phosphorus chloride (1.3 μL) and anhydrous acetonitrile (17 mL) was stirred at 90° C. for 1 hour. The reaction mixture was poured over cracked ice/water. The aqueous layer was extracted with dichloromethane (3×60 mL). The organic layer was washed with sodium hydrogenocarbonate 5%, water and was evaporated to dryness. The crude product was purified on silica gel using n-hexane/ethyl acetate (3/1) as eluant to give the title compound (404 mg) as a yellow powder.

$^1$H NMR (DMSO-$d_6$) δ ppm: 4.82-6.87 (m, 2H), 4.9-6.95 (m, 1H), 6.0-6.08 (m, 1H), 6.12-6.19 (m, 1H), 6.90 (d, 1H, J=5.2 Hz, H1'), 7.47-7.73 (m, 9H), 7.88-8.12 (m, 6H), 9.10 (s, 1H, H8), 9.90 (s, 1H, H3)

Step D: 4-amino-1-(β-D-ribofuranosyl)imidazo[4,5-d]pyridazine

The compound from Step C (420 mg, 0.7 mmol) was added to a solution of ammonia in methanol and stirred in a steel bomb at 150° C. for 6 hours. The reaction mixture was evaporated to dryness to afford a brown oil which was purified on silica gel reverse-phase (C18) using water as eluant to give the title compound (50 mg) as a yellow powder.

$^1$H NMR (DMSO-$d_6$) δ ppm: 3.58-4.48 (m, 5H, H2', H3', H4', 2H5'), 5.14-5.68 (m, 3H, 3×OH), 5.90 (s, 1H, H1'), 6.61 (br, 2H, $NH_2$), 8.59 (s, 1H, H8), 9.12 (s, 1H, H3)

Example 6

Synthesis of 1-(β-D-ribofuranosyl)imidazo[4,5-d]pyridazin-4-one

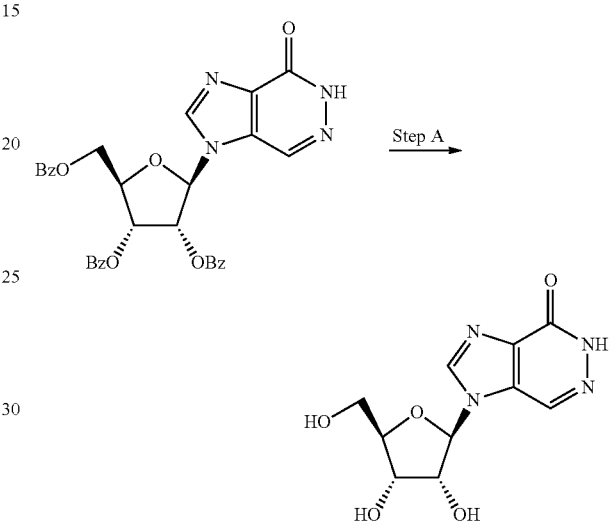

1-(2,3,5-tri-O-Benzoyl-β-D-ribofuranosyl)imidazo[4,5-d]pyridazin-4-one (555 mg, 0.9 mmol) was added to a solution of sodium methylate (205 mg) in methanol (25 mL) and stirred at 20° C. for 2 hours. The reaction mixture was evaporated to dryness. The residue was dissolved in water and washed with ethyl acetate. The aqueous layer was concentrated under pressure. The crude product was purified on silica gel reverse-phase (C18) using water as eluant to give the title compound (220 mg) as a white powder.

$^1$H NMR (DMSO-$d_6$) δ ppm: 3.59-3.62 (m, 2H), 4.02 (m, 1H), 4.11 (m, 1H), 4.22 (m, 1H), 5.16-5.72 (m, 3H, 3×OH), 5.91 (s, 1H, H1'), 8.52 (s, 1H, H8), 8.68 (s, 1H, H3), 12.75 (br, 1H, NH).

Mass spectrum: m/z (FAB>0) 537 (2M+H)$^+$, 269 (M+H)$^+$, (FAB<0) 535 (2M+H)$^+$, 267 (M−H)$^−$

Example 7

Synthesis of 4-amino-1-(2-C-methyl-β-D-ribofuranosyl)imidazo[4,5-d]pyridazine

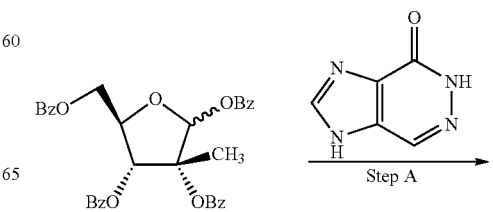

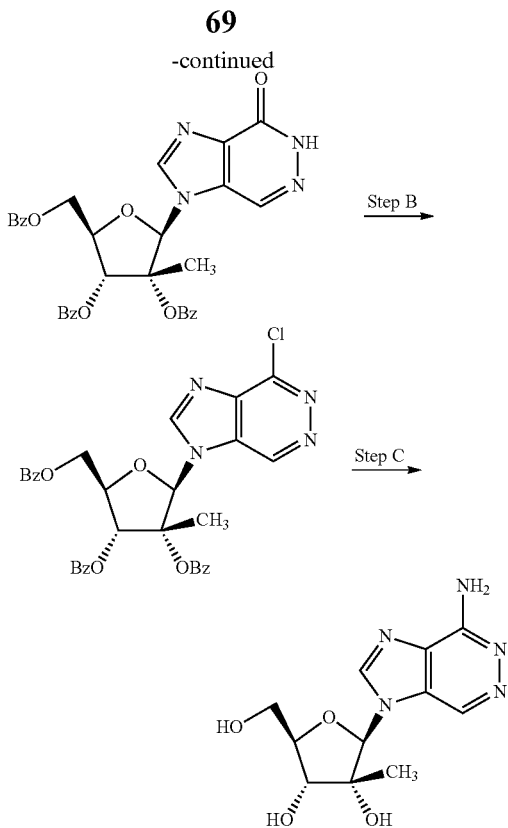

Step A: 1-(2-C-methyl-2,3,5-tri-O-Benzoyl-β-D-ribofuranosyl)imidazo[4,5-d]pyridazin-4-one To a suspension of imidazo[4,5-d]pyridazine (3.48 g, 25.5 mmol) [for preparation see *Journal of Heterocyclic Chemistry*, 1969, Vol 6, 93] in dry acetonitrile (35 mL) was added 1,2,3,5-tetra-O-benzoyl-2-C-methyl-β-D-ribofuranose (14.48 g, 25.0 mmol) at 20° C. and stirred for 15 mn. DBU (11.5 mL, 76.3 mmol) was added at 0° C. and the solution was stirred for 15 mn at 0° C. TMSOTf (24.7 mL, 127.8 mmol) was added at 0° C. and the mixture was heated at 80° C. for 20 hours. The reaction mixture was poured into an aqueous solution of sodium hydrogenocarbonate and extracted by ethyl acetate. The organic layer was evaporated to dryness to give a yellow powder. The crude product was purified on silica gel using dichloromethane/methanol (99.3/0.7) as eluant to give a slight yellow powder which was crystallized from isopropanol to give the title compound (2.45 g) as a white powder.

$^1$H NMR (DMSO-$d_6$) δ ppm: 1.48 (s, 3H, CH$_3$), 4.75-4.96 (m, 3H, H4', 2H5'), 5.81 (d, 1H, J=5.5 Hz, H3'), 6.99 (s, 1H, H1'), 7.39-7.72 (m, 9H), 7.92-8.08 (m, 6H), 8.64 (s, 1H, H8), 8.71 (s, 1H, H3), 12.89 (br, 1H, NH).

Mass spectrum: m/z (FAB>0) 1189 (2M+H)$^+$, 585 (M+H)$^+$, (FAB<0) 593 (M−H)$^−$ Step B: 4-chloro-1-(2-C-methyl-2,3,5-tri-O-Benzoyl-β-D-ribofuranosyl)imidazo[4,5-d]pyridazine A solution containing the compound from Step A (300 mg, 0.50 mmol), the N,N-diethylaniline (1.2 mL) and freshly distilled phosphorus chloride (24 mL) was stirred at reflux for 1 hour. The reaction mixture was evaporated to dryness. Dichloromethane was added to the residue and the organic layer poured over cracked ice/water. The aqueous layer was extracted with dichloromethane. The organic layer was washed with sodium hydrogenocarbonate 5%, water and was evaporated to dryness. The crude product was purified on silica gel using diethyl ether/petrol ether (1/1) as eluant to give the title compound (295 mg) as a white powder.

$^1$H NMR (DMSO-$d_6$) δ ppm: 1.5 (s, 3H, CH$_3$), 4.8-5.0 (m, 3H, H4', 2H5'), 5.85 (d, 1H, J=5.5 Hz, H3'), 7.15 (s, 1H, H1'), 7.38-8.08 (m, 15H), 9.15 (s, 1H, H8), 9.90 (s, 1H, H3)

Step C: 4-amino-1-(2-C-methyl-β-D-ribofuranosyl)imidazo[4,5-d]pyridazine

The compound from Step B (590 mg, 0.96 mmol) was added to a solution of ammonia in methanol and stirred in a steel bomb at 150° C. for 6 hours. The reaction mixture was evaporated to dryness to remove methanol. The crude product was purified on silica gel reverse-phase (C18) using water as eluant to give the title compound (35 mg) as a white powder.

$^1$H NMR (DMSO-$d_6$) δ ppm: 0.70 (s, 3H, CH$_3$), 3.64-3.98 (m, 4H, H3', H4', 2H5'), 5.23-5.44 (m, 3H, 3OH), 5.98 (s, 1H, H1'), 6.63 (br, 2H, NH$_2$), 8.68 (s, 1H, H8), 9.05 (s, 1H, H3)

$^{13}$C NMR (DMSO-$d_6$) δ ppm: 155, 143, 132, 131, 129, 93, 83, 79, 72, 20.

Mass spectrum: m/z (FAB>0) 282 (M+H)$^+$, (FAB<0) 280 (M−H)$^−$

Example 8

Synthesis of the 4-substituted-1-(2-C-methyl-β-D-ribofuranosyl) imidazo[4,5-d]pyridazine

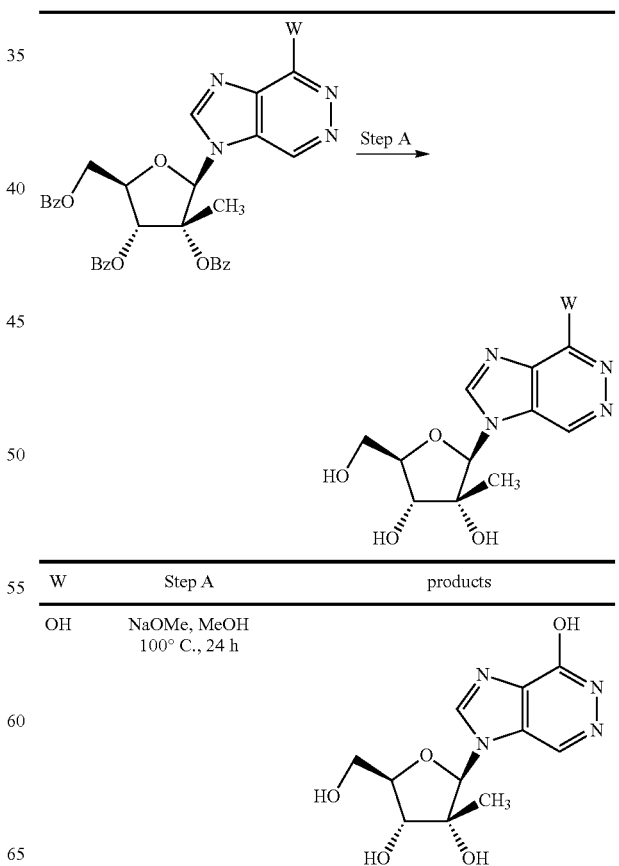

| W | Step A | products |
|---|--------|----------|
| OH | NaOMe, MeOH 100° C., 24 h | OH |

-continued

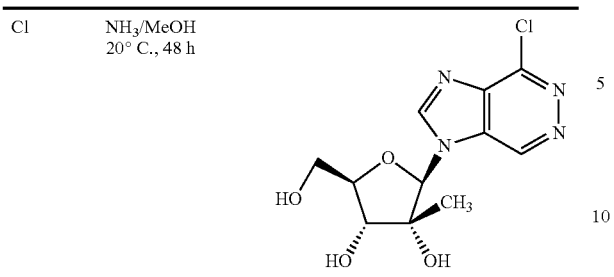

1-(2-C-methyl-β-D-ribofuranosyl)imidazo[4,5-d]pyridazin-4-one

¹H NMR (DMSO-d₆) δ ppm: 1.17 (s, 3H, CH₃), 3.44-3.59 (m, 1H), 3.68-3.78 (m, 1H), 3.86-3.94 (m, 1H), 4.11-4.21 (m, 1H), 4.8-5.4 (m, 3H, 3OH), 6.05 (s, 1H, H1'), 8.35 (s, 1H, H8), 8.37 (s, 1H, H3), 12.67 (br, 1H, NH).
Mass spectrum m/z (FAB>0) 283 (2M+H)⁺, 281 (M+H)⁺

4-chloro-1-(2-C-methyl-β-D-ribofuranosyl)imidazo[4,5-d]pyridazine

¹H NMR (DMSO-d₆) δ ppm: 0.72 (s, 3H, CH₃), 3.69-4.06 (m, 4H, H3', H4', 2H5'), 5.34-5.51 (m, 3H, 3OH), 6.19 (s, 1H, H1'), 9.18 (s, 1H, H8), 9.87 (s, 1H, H3)
Mass spectrum: m/z (FAB>0) 301 (M+1H)⁺, (FAB<0) 299 (M−H)⁻

Example 9

Synthesis of the 4,7-diamino-imidazo[4,5-d]pyridazine nucleosides

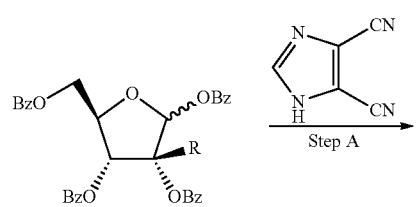

Step A:

To a suspension of 4,5-dicyanoimidazole (1 eq.) [for preparation see *Journal of Organic Chemistry*, 1976, Vol 41, 713] in dry DMF (0.2 M) was added the protected β-D-ribofuranose derivatives (1 eq.) at 20° C. DBU (3 eq.) was added at 0° C. and the solution was stirred for 20 mn at 0° C. TMSOTf (4 eq.) was added at 0° C. and the mixture was heated at 60° C. for 1 hour. The reaction mixture was poured into an aqueous solution of sodium hydrogenocarbonate and extracted by dichloromethane. The organic layer was evaporated to dryness to give a yellow powder. The crude product was purified on silica gel using diethyl ether/petrol ether as eluant to give the title compound (see the following table 1).

Step B:

The compound from Step A (1 eq.) was stirred with hydrazine monohydrate (20 eq.) and acetic acid (1.4 eq.) at 75° C. for several hours (see the following table 1). The reaction mixture was poured into water. The aqueous layer was washed by dichloromethane and evaporated under pressure. The residue was purified on reverse-phase column to give the title compound (see the following table 1).

TABLE 1

| R | products from Step A | yield (Step A) | experiments (Step B) | products from Step B | yield (Step A) |
|---|---|---|---|---|---|
| H | (structure) | 63% | 75° C. for 1.5 h. | (structure) | 58% (white powder) |

TABLE 1-continued

| R | products from Step A | yield (Step A) | experiments (Step B) | products from Step B | yield (Step A) |
|---|---|---|---|---|---|
| CH$_3$ | (structure: BzO-ribofuranosyl-CH$_3$-imidazole-dicyano) | 62% | 75° C. for 20 h. | (structure: 4,7-diamino-1-(2-C-methyl-β-D-ribofuranosyl)imidazo[4,5-d]pyridazine) | 15% (white powder) |

4,7-diamino-1-β-D-ribofuranosylimidazo[4,5-d]pyridazine $^1$H NMR (DMSO-d$_6$) δ ppm: 3.58-4.32 (m, 5H, H2', H3', H4', 2H5'), 5.10-5.90 (br, 7H, 2NH$_2$, 3OH), 6.11 (s, 1H, H1'), 8.50 (s, 1H, H8)
$^{13}$C NMR (DMSO-d$_6$) δ ppm: 151, 144, 142, 132, 122, 89, 86, 75, 70, 61.
Mass spectrum: m/z (FAB>0) 283 (M+H)$^+$, (FAB<0) 281 (M−H)$^−$ 4,7-diamino-1-(2-C-methyl-β-D-ribofuranosyl)imidazo[4,5-d]pyridazine $^1$H NMR (DMSO-d$_6$) δ ppm: 0.75 (s, 3H, CH$_3$), 3.67-3.76 (m, 1H), 3.84-3.94 (m, 3H), 5.32 (m, 3H, 3OH), 5.43 (br, 1H, NH$_2$), 5.71 (br, 1H, NH$_2$), 6.21 (s, 1H, H1'), 8.78 (s, 1H, H8)
$^{13}$C NMR (DMSO-d$_6$) δ ppm: 151, 144, 142, 132, 123, 92, 83, 78, 71, 59, 20.
Mass spectrum: m/z (FAB>0) 593 (2M+H)$^+$, 297 (M+H)$^+$, (FAB<0) 295 (M−H)$^−$ Example 10

Synthesis of 4,7-disubstituted-imidazo[4,5-d]pyridazine nucleosides

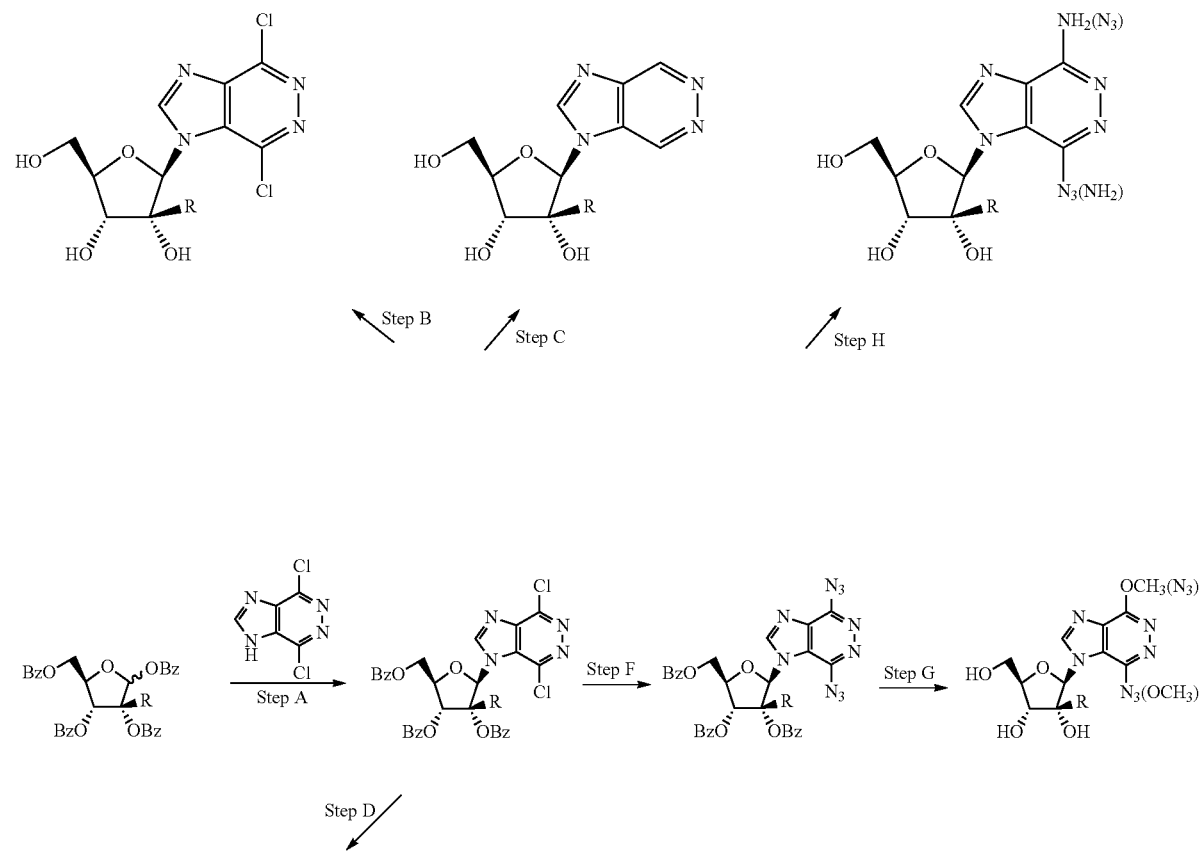

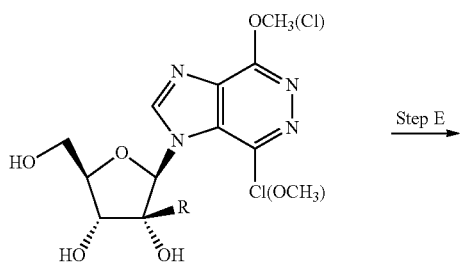 Step E 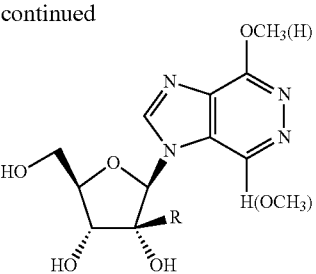

Step A: Typical procedure for the preparation of the protected 4,7-dichloroimidazo[4,5-d]pyridazine nucleosides The 4,7-dichloroimidazo[4,5-d]pyridazine [for preparation see *Journal of Heterocyclic Chemistry*, 1968, Vol 5, 13] (1 eq.) was heated at reflux in hexamethyldisilazane for 12 hours. The mixture was evaporated to dryness to give a solid which was dissolved in 1,2-dichloroethane. The protected β-D-ribofuranose derivatives (1.1 eq.) and stannic chloride (1.4 eq.) were added at 20 C. and the solution was stirred for 3 hours. The reaction mixture was poured into an aqueous solution of sodium hydrogenocarbonate, filtrated through a pad of celite and washed by dichloromethane. The organic layer was evaporated to dryness. The crude product was purified on silica gel using dichloromethane/acetone (40/1) as eluant to give the title compound (see the following table 2).

Step B: Typical procedure for the preparation of the 4,7-dichloroimidazo[4,5-d]pyridazine nucleosides The compound from Step A (1 eq.) was stirred with sodium methoxide (0.1 eq.) in methanol for several hours. The reaction mixture was evaporated under pressure. Water was added to the residue. The aqueous layer was washed by ethyl acetate and was evaporated under pressure. The residue was purified on reverse-phase column to give the title compound (see the following table 2).

Step C: Typical procedure for the preparation of the imidazo[4,5-d]pyridazine nucleosides A mixture of the compound from Step A (1 eq.), palladium on charcoal (10%), sodium acetate (4.2 eq.) in acetyl acetate was stirred under hydrogen until the compound from Step A was consumed. The reaction mixture was evaporated under pressure and was purified on silica gel to give the title protected compound which was stirred with sodium methoxide (3.3 eq.) in methanol. The reaction mixture was evaporated under pressure. Water was added to the residue. The aqueous layer was washed by ethyl acetate and was evaporated under pressure. The residue was purified on reverse-phase column to give the title compound (see the following table 2).

Step D: Typical procedure for the preparation of the chloro-methoxy-imidazo[4,5-d]pyridazine nucleosides The compound from Step A (1 eq.) was stirred with sodium methoxide (3.3 eq.) in methanol 0.3M at 20° C. for several hours. The reaction mixture was evaporated under pressure. Water was added to the residue. The aqueous layer was washed by ethyl acetate and was evaporated under pressure. The residue was purified on reverse-phase column to give a compound whose regioselectivity was not given (see the following table 2).

Step E: Typical procedure for the preparation of the methoxy-imidazo[4,5-d]pyridazine nucleosides A mixture of the compound from Step D (1 eq.), palladium on charcoal (10%), sodium acetate (4.2 eq.) in water/ethanol (1/1) was stirred under hydrogen until the compound from Step A was consumed. The reaction mixture was evaporated under pressure and was purified on reverse-phase column to give the title compound whose regioselectivity was not given (see the following table 2).

Step F: Typical procedure for the preparation of the protected 4,7-diazidoimidazo[4,5-d]pyridazine nucleosides The compound from Step A (1 eq.) was treated at 50° C. with sodium azide (1.5 eq.) in DMF. Water was added to the mixture. The aqueous layer was extracted by ethyl acetate. The organic layer was evaporated under pressure. The crude product was purified on silica gel using diethyl ether/petrol ether (7/3) as eluant to give the title compound (see the following table 2).

Step G: Typical procedure for the preparation of the azido-methoxy-imidazo[4,5-d]pyridazine nucleosides The compound from Step F (1 eq.) was stirred at 50° C. with sodium methoxide (1 eq.) in methanol. The reaction mixture was evaporated under pressure. Water was added to the residue. The aqueous layer was washed by ethyl acetate and was evaporated under pressure. The residue was purified on reverse-phase column using water/acetonitrile as eluant to give the title compound whose regioselectivity was not given (see the following table 2).

Step H: Typical procedure for the preparation of the amino-azido-imidazo[4,5-d]pyridazine nucleosides A mixture of the compound from Step F (1 eq.), palladium on charcoal (10%), sodium acetate (4.2 eq.) in ethyl acetate was stirred under hydrogen until the compound from Step F was consumed. The reaction mixture was filtrated over celite and was evaporated under pressure The crude product was purified on silica gel to give the title protected compound whose regioselectivity was not given (see the following table 1). This compound was stirred with sodium methoxide (3 eq.) in methanol. The reaction mixture was evaporated under pressure. Water was added to the residue. The aqueous layer was washed by ethyl acetate and was evaporated under pressure.

The residue was purified on reverse-phase column to give the title compound whose regioselectivity was not given (see the following table 2).

TABLE 2

| experiments | products | yield |
|---|---|---|
| Step A | [imidazo-pyridazine with 4,7-diCl, ribose with BzO at 5', 3', 2'-OBz] | 60% (white powder) |
| Step A | [imidazo-pyridazine with 4,7-diCl, ribose with BzO at 5', 3'-OBz, 2'-CH₃, 2'-OBz] | 34% (white powder) |
| Step B | [imidazo-pyridazine with 4,7-diCl, ribose with HO at 5', 3'-OH, 2'-CH₃, 2'-OH] | (white powder) |
| Step C | [imidazo-pyridazine unsubstituted, ribose with HO, CH₃, OH] | 71% (white powder) |
| Step D | [imidazo-pyridazine with OCH₃(Cl) and Cl(OCH₃), ribose HO/OH] | 55% (white powder) |
| Step E | [imidazo-pyridazine with OCH₃(H) and H(OCH₃), ribose HO/OH] | 55% (white powder) |
| Step F | [imidazo-pyridazine with 4,7-diN₃, ribose BzO/OBz] | 50% (yellow powder) |
| Step F | [imidazo-pyridazine with 4,7-diN₃, ribose BzO, CH₃, OBz] | 50% (yellow powder) |
| Step G | [imidazo-pyridazine with N₃(OCH₃) and OCH₃(N₃), ribose HO, CH₃, OH] | 36% (beige powder) |
| Step H | [imidazo-pyridazine with NH₂(N₃) and N₃(NH₂), ribose BzO, CH₃, OBz] | 98% (white powder) |
| Step H | [imidazo-pyridazine with NH₂(N₃) and N₃(NH₂), ribose HO, CH₃, OH] | 49% (white powder) |

4,7-dichloro-1-(2,3,5-tri-O-Benzoyl-β-D-ribofuranosyl)imidazo[4,5-d]pyridazine $^1$H NMR (DMSO-d$_6$) δ ppm: 4.8-5.0 (m, 3H, H4', 2H5'), 6.05 (s, 1H, H3'), 6.25 (s, 1H, H2'), 7.1 (d, 1H, J=4 Hz, H1'), 7.4-8.0 (m, 15H), 9.25 (s, 1H, H8).
Mass spectrum: m/z (FAB>0) 633 (M+H)$^+$

4,7-dichloro-1-(2-C-methyl-2,3,5-tri-O-Benzoyl-β-D-ribofurnosyl)imidazo[4,5-d]pyridazine $^1$H NMR (DMSO-d$_6$) δ ppm: 1.65 (s, 3H, CH$_3$), 4.9-5.0 (m, 3H, H4', 2H5'), 5.8 (s, 1H, H3'), 7.35-8.05 (m, 16H including H1'), 9.3 (s, 1H, H8).

4,7-dichloro-1-(2-C-methyl-β-D-ribofuranosyl)imidazo[4,5-d]pyridazine $^1$H NMR (DMSO-d$_6$) δ ppm: 0.84 (s, 3H, CH$_3$), 3.77 (m, 1H), 3.88-4.04 (m, 3H), 5.30-5.60 (m, 3H, OH), 6.5 (s, 1H, H1'), 9.44 (s, 1H, H8).

1-(2-C-methyl-β-D-ribofuranosyl)imidazo[4,5-d]pyridazine $^1$H NMR (DMSO-d$_6$) δ ppm: 0.80 (s, 3H, CH$_3$), 3.75 (m, 1H), 3.80-4.00 (m, 3H), 5.40 (br, 3H, OH), 6.2 (s, 1H, H1'), 9.0 (s, 1H), 9.65 (s, 1H), 9.85 (s, 1H).

7-chloro-4-methoxy-1-β-D-ribofuranosylimidazo[4,5-d]pyridazine or 4-chloro-7-methoxy-1-β-D-ribofuranosylimidazo[4,5-d]pyridazine $^1$H NMR (DMSO-d$_6$) δ ppm: 3.6-4.5 (m, 8H, 2H5', H4', H3', H2', OCH$_3$), 5.40 (m, 3H, OH), 6.2 (s, 1H, H1'), 9.0 (s, 1H, H8).
675 (2M+H)$^+$, Mass spectrum: m/z (FAB>0) 317 (M+H)$^+$, (FAB<0) 315 (M−H)$^−$

4-methoxy-1-β-D-ribofuranosylimidazo[4,5-d]pyridazine or 7-methoxy-1-β-D-ribofuranosylimidazo[4,5-d]pyridazine $^1$H NMR (DMSO-d$_6$) δ ppm: 3.54-3.79 (m, 2H), 3.95 (m, 1H), 4.15 (m, 1H, H3'), 4.2 (s, 3H, OCH$_3$), 4.4 (m, 1H, H2'), 5.05-5.70 (m, 3H, OH), 6.2 (d, 1H, J=4.8 Hz, H1'), 8.95 (s, 1H), 9.3 (s, 1H).
$^{13}$C NMR (DMSO-d$_6$) δ ppm: 154, 145, 143, 142, 121, 90, 85, 75, 70, 61, 55.
Mass spectrum: m/z (FAB>0) 283 (M+H)$^+$, (FAB<0) 281 (M−H)$^−$

4,7-diazido-1-(2,3,5-tri-O-Benzoyl-β-D-ribofuranosyl)imidazo[4,5-d]pyridazine $^1$H NMR (DMSO-d$_6$) δ ppm: 4.81-5.1 (m, 3H, H4', 2H5'), 6.24-6.49 (m, 2H, H2', H3'), 7.2 (d, 1H, J=5 Hz, H1'), 7.4-8.0 (m, 15H), 9.12 (s, 1H, H8).
Mass spectrum: m/z (FAB>0) 647 (M+H)$^+$

4,7-diazido-1-(2-C-methyl-2,35-tri-O-Benzoyl-β-D-ribofuranosyl)imidazo[4,5-d]pyridazine $^1$H NMR (DMSO-d$_6$) δ ppm: 1.6 (s, 3H, CH$_3$), 4.96 (m, 3H, H4', 2H5'), 6.02 (m, 1H, H3'), 7.24 (s, 1H, H1'), 7.40-7.52 (m, 6H), 7.60-7.71 (m, 3H), 7.93-8.1 (m, 6H), 9.10 (s, 1H, H8).
Mass spectrum: m/z (FAB>0) 661 (M+H)$^+$

4-azido-7-methoxy-(2-C-methyl-β-D-ribofuranosyl)imidazo[4,5-d]pyridazine or 7-azido-4-methoxy-1-(2-C-methyl-β-D-ribofuranosyl)imidazo[4,5-d]pyridazine $^1$H NMR (DMSO-d$_6$) δ ppm: 0.75 (s, 3H, CH$_3$), 3.70-3.98 (m, 2H), 4.05 (m, 2H), 4.2 (s, 3H, OCH$_3$), 5.32-5.61 (br, 3H, OH), 6.36 (d, 1H, J=5.7 Hz, H1'), 9.18 (s, 1H, H8),
$^{13}$C NMR (DMSO-d$_6$) δ ppm: 156, 143, 136, 129, 123, 94, 83, 79, 71, 59, 57, 20.
Mass spectrum: m/z (FAB>0) 675 (2M+H)$^+$, 338 (M+H)$^+$, (FAB<0) 673 (2M−H)$^−$, 336 (M−H)

4 amino-7-azido-1-(2-C-methyl-2,3,5-tri-O-Benzoyl-β-D-ribofuranosyl)imidazo[4,5-d]pyridazine or 7-amino-4-azido-1-(2-C-methyl-2,3,5-tri-O-Benzoyl-β-D-ribofuranosyl) imidazo[4,5-d]pyridazine $^1$H NMR (DMSO-d$_6$) δ ppm: 01.64 (s, 3H, CH$_3$), 4.95 (m, 3H), 6.06 (m, 1H, H3'), 7.18 (s, 1H, H1'), 7.40-7.52 (m, 6H), 7.63-7.74 (m, 5H, including NH$_2$), 7.91-8.04 (m, 6H), 8.96 (s, 1H, H8),
Mass spectrum: m/z (FAB>0) 1269 (2M+H)$^+$, 635 (M+H)$^+$, (FAB<0) 633 (M−H)$^−$

4-amino-7-azido-(2-C-methyl-β-D-ribofuranosylimidazo[4,5-d]pyridazine or 7-amino-4-azido-1-(2-C-methyl-β-D-ribofuranosyl)imidazo[4,5-d]pyridazine $^1$H NMR (DMSO-d$_6$) δ ppm: 0.75 (s, 3H, CH$_3$), 3.65-4.15 (m, 4H), 5.30-5.55 (br, 3H, 3×OH), 6.27 (s, 1H, H1'), 7.63 (br, 2H, NH$_2$), 9.03 (s, 1H, H8),
Mass spectrum: m/z (FAB>0) 323 (M+H)$^+$, (FAB<0) 321 (M−H)

Example 11

Synthesis of 4-amino-6-substituted-imidazo[4,5-d]-v-triazine

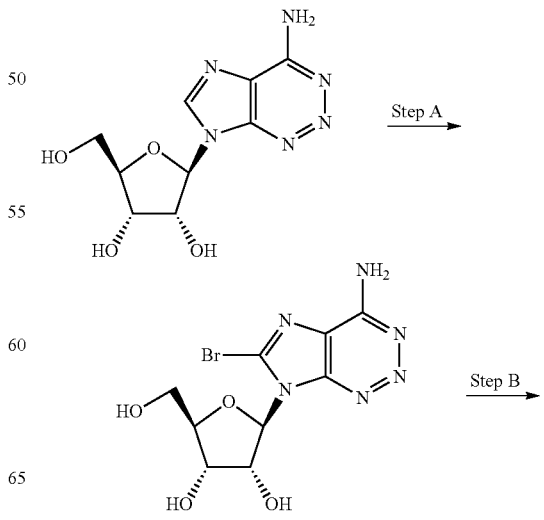

-continued

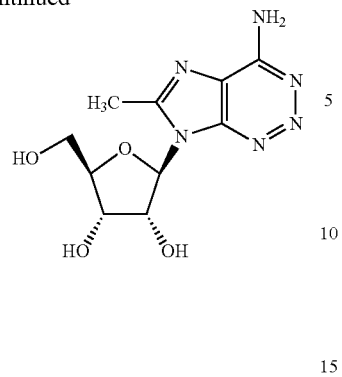

Step A: 4-amino-6-bromo-7-(β-D-ribofuranosyl)imidazo[4,5-d]-v-triazine

The 2-azaadenosine [for preparation see Patent WO 01/16149, 2001] (70 mg, 0.26 mmol) was added to a solution of sodium acetate 0.5M (1.4 mL). The solution was heated until the 2-azaadenosine was solubilized. A solution of bromine (100 μL of $Br_2$ in 10 mL of water) (6.3 mL, 1.22 mmol) was added and the mixture was stirred at 20° C. for 3 days. A second portion of the bromine's solution (6.3 mL, 1.22 mmol) was added and the mixture was stirred at 20° C. for 3 hours. The reaction mixture was evaporated to dryness. The crude product was purified on silica gel reverse-phase (C18) using water/acetonitrile (9/1) as eluant to give the title compound as a yellow powder.

$^1$H NMR (DMSO-ds) δ ppm: 3.55 (m, 1H, $H_5'$), 3.71 (m, 1H, $H_5'$), 4.01 (m, 1H, $H_4'$), 4.31 (m, 1H, $H_3'$), 5.17 (m, 1H, $H_2'$), 5.19 (m, 1H, OH), 5.36 (m, 1H, OH), 5.58 (m, 1H, OH), 5.93 (d, 1H, J=6.47 Hz, $H_1'$), 8.08 (br, 2H, $NH_2$).

Mass spectrum: m/z (FAB>0) 349 $(M+2H)^+$, m/z (FAB<0) 345 $(M-2H)^-$.

Step B: 4-amino-6-methyl-7-(β-D-ribofuranosyl)imidazo[4,5-d]-v-triazine

The compound from Step A (112 mg, 0.3 mmol) was heated at reflux in hexamethyldisilazane (15 mL) for 16 hours. The mixture was evaporated to dryness to give a syrup which was dissolved in dry THF (12 mL). $PPh_3$ (10 mg; 0.04 mmol), $PdCl_2$ (3.5 mg; 0.02 mmol) and $AlMe_3$ (100 μl; 0.94 mmol) were added. The mixture was reflux for 5 hours. The mixture was evaporated to dryness. The crude product was dissolved in methanol (30 mL) in the presence of ammonium chloride. The mixture was evaporated to dryness and the residue was purified on silica gel reverse-phase (C18) using water/acetonitrile (from 9/1 to 6/4) as eluant to give the title compound (35 mg) as a yellow powder.

$^1$H NMR (DMSO-$d_6$) δ ppm: 2.67 (s, 3H, $CH_3$), 3.60 (m, 1H, $H_5'$), 3.72 (m, 1H, $H_5'$), 4.03 (m, 1H, $H_4'$), 4.24 (m, 1H, $H_3'$), 4.93 (m, 1H, $H_2'$), 5.48 (m, 3H, OH), 5.92 (d, 1H, J=6.82 Hz, $H_1'$), 7.78 (br, 2H, $NH_2$).

Mass spectrum: m/z (FAB>0) (FAB>0) 283 $(M+H)^+$, m/z (FAB<0) 281 $(M-H)^-$.

Example 12

Synthesis of imidazo[4,5-d]-v-triazin-4-one nucleosides

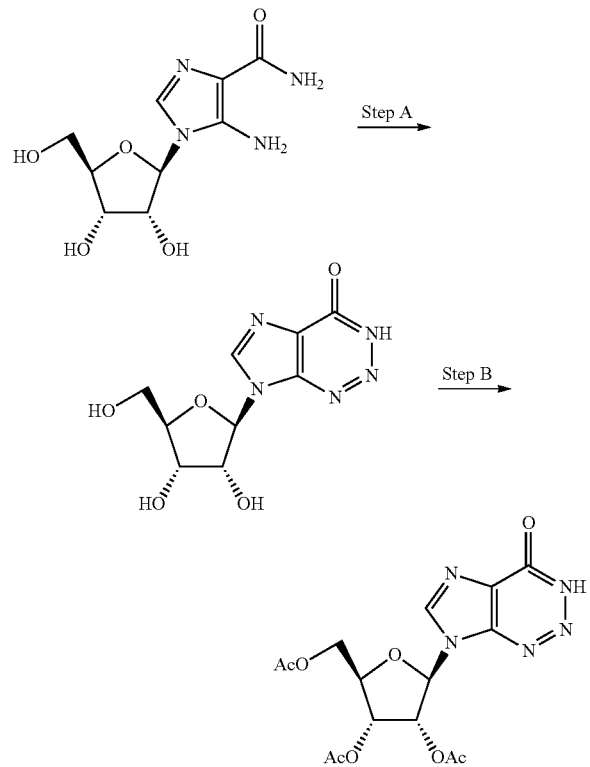

Step A: 7-(β-D-Ribofuranosyl)imidazo[4,5-d]-v-triazin-4-one

The AICAR [for preparation see Synthesis, 2003, No 17, 2639] (1 g, 3.87 mmol) was added to a solution of chlorhydrique acid 6N (25 mL) at −30° C. A solution of sodium nitrite 3M (4 ml, 11.62 mmol) was added and the mixture was stirred at −30° for 2 hours. A pre-cooled (−30° C.) solution of ethanol (25 mL) was added. A solution of ammonia (28%) was added at −20° C. to pH=7. The reaction mixture was evaporated to dryness. The crude product was purified on silica gel reverse-phase (C18) using water as eluant to give the title compound (0.81 gr) as a white powder.

$^1$H NMR (DMSO-$d_6$) δ ppm: 3.58 (d, 1H, J=11.85 Hz, $H_5'$), 3.70 (d, 1H, J=11.85 Hz, $H_5'$), 4.00 (dd, 1H, J=3.92 Hz, 4.02 Hz, $H_4'$), 4.18 (dd, 1H, J=4.27 Hz, 4.78 Hz, $H_3'$), 4.54 (dd, 1H, J=4.86 Hz, 5.19 Hz, $H_2'$), 5.18 (br, 1H, OH), 5.35 (br, 1H, OH), 5.73 (br, 1H, OH), 6.08 (d, 1H, J=5.11 Hz, H1'), 8.65 (s, 1H, $H_8$).

Step B: 7-(2,3,5-Tri-O-acétyl-β-D-ribofuranosyl)imidazo[4,5-d]-v-triazin-4-one

The compound from Step A (1.68 gr, 6.24 mmol) was stirred in pyridine (20 mL). The anhydride acetic (2.3 ml, 25 mmol) was added and the mixture was stirred at 20° C. for 16 hours. The mixture was evaporated to dryness to give a syrup which was dissolved in water. The aqueous layer was extracted by acetyl acetate. The organic layer was evaporated to dryness to give the title compound (1.5 gr) as a brown foam.

$^1$H NMR (DMSO-$d_6$) δ ppm: 2.04 (s, 3H, $COCH_3$), 2.09 (s, 3H, $COCH_3$), 2.10 (s, 3H, $COCH_3$), 4.39 (m, 3H, 2×$H_5'$ et $H_4'$), 5.53 (dd, 1H, J=4.39 Hz, 5.4 Hz, $H_3'$), 5.80 (t, 1H, J=5.4 Hz, $H_2'$), 6.26 (d, 1H, J=5.4 Hz, $H_1'$), 8.15 (s, 1H, $H_8$).

Example 13

Alternative Methods for Ribofuranosyl-Purine Analogues Synthesis

I. Preparation of 4-methylamino-7-(β-D-ribofuranosyl)imidazo[4,5-d]-v-triazine

The 4-methylamino-7-(β-D-ribofuranosyl)imidazo[4,5-d]-v-triazine Va may be prepared according the following synthesis, where the starting material used is the AICAR I. The AICAR may be prepared according to the published synthesis of Y. Yamamoto and N. Kohyama, *Synthesis,* 2003, 17:2639-2646.

The other synthesis of 4-methylamino-7-(β-D-ribofuranosyl)imidazo[4,5-d]-v-triazine Va was described from 2-azainosine II according to the published synthesis of L. Towsend and Co, *Nucleosides, Nucleotides & Nucleic Acids,* 2000, 19 (1&2):39-68.

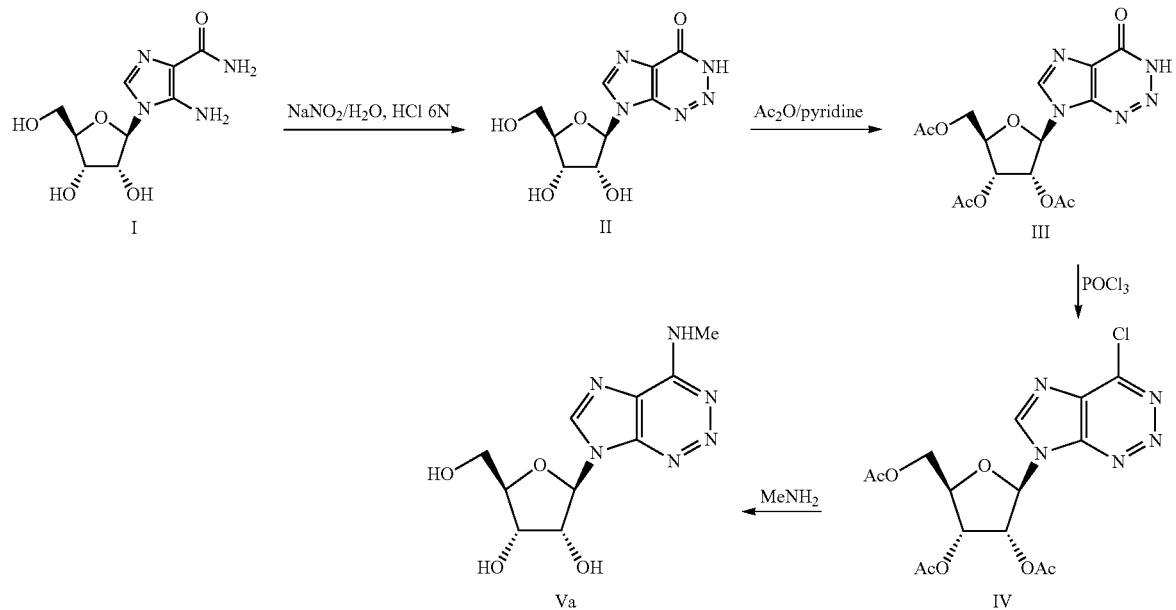

II. Preparation of 4-substituted-7-(2,3-dideoxy-β-D-glycero-pentofuranosyl)-imidazo-[4,5-d]-v-triazine derivative compounds The 4-substituted-7-(2,3-dideoxy-β-D-glycero-pentofuranosyl)imidazo[4,5-d]-v-triazine compounds IXa, IXb and IXc may be prepared according the following synthesis according to the published synthesis of R. Panzica and Co, *Bioorganic & Medicinal Chemistry,* 1999, 7:2373-2379.

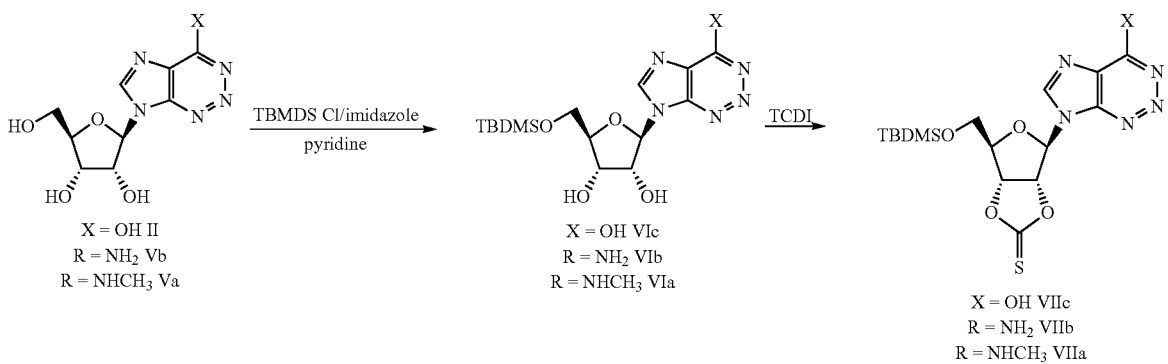

-continued

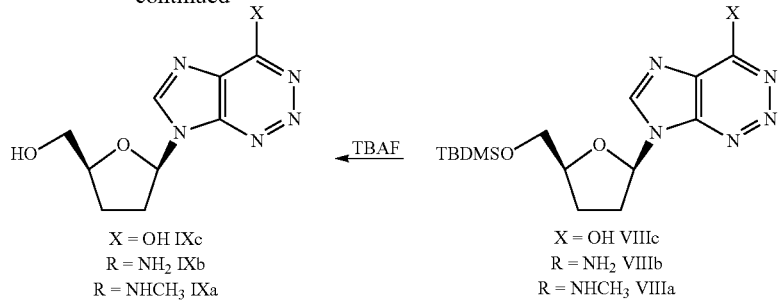

X = OH IXc
R = NH₂ IXb
R = NHCH₃ IXa

X = OH VIIIc
R = NH₂ VIIIb
R = NHCH₃ VIIIa

III. Preparation of 4-substituted-7-(2,3-dideoxy-β-D-glycero-pent-2-ene-furanosyl)-imidazo-[4,5-d]-v-triazine derivative compounds 4-substituted-7-(2,3-dideoxy-β-D-glycero-pent-2-ene-furanosyl)-imidazo-[4,5-d]-v-triazine derivative compounds XIa, XIb and XIc may be prepared according the following synthesis:

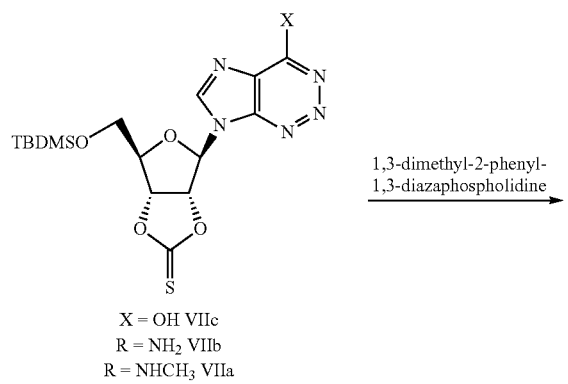

X = OH VIIc
R = NH₂ VIIb
R = NHCH₃ VIIa

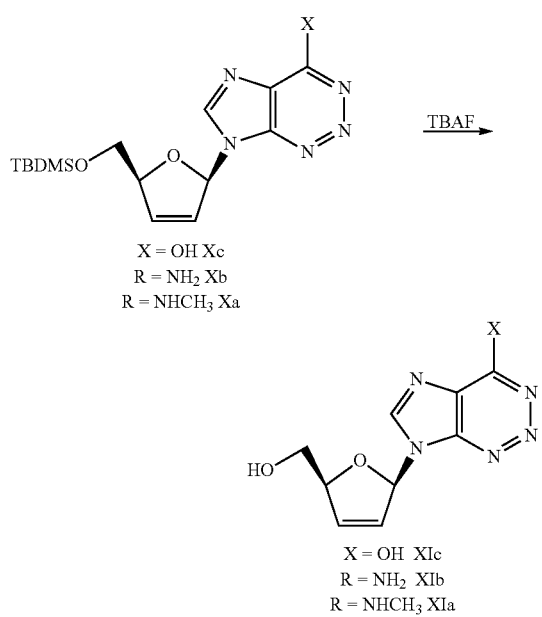

X = OH Xc
R = NH₂ Xb
R = NHCH₃ Xa

X = OH XIc
R = NH₂ XIb
R = NHCH₃ XIa

Example 14

Phosphorylation Assay of Nucleoside to Active Triphosphate

To determine the cellular metabolism of the compounds, HepG2 cells are obtained from the American Type Culture Collection (Rockville, Md.), and are grown in 225 cm² tissue culture flasks in minimal essential medium supplemented with non-essential amino acids, 1% penicillin-streptomycin. The medium is renewed every three days, and the cells are subcultured once a week. After detachment of the adherent monolayer with a 10 minute exposure to 30 mL of trypsin-EDTA and three consecutive washes with medium, confluent HepG2 cells are seeded at a density of $2.5 \times 10^6$ cells per well in a 6-well plate and exposed to 10 μM of [³H] labeled active compound (500 dpm/pmol) for the specified time periods. The cells are maintained at 37° C. under a 5% $CO_2$ atmosphere. At the selected time points, the cells are washed three times with ice-cold phosphate-buffered saline (PS). Intracellular active compound and its respective metabolites are extracted by incubating the cell pellet overnight at −20° C. with 60% methanol followed by extraction with an additional 20 μl of cold methanol for one hour in an ice bath. The extracts are then combined, dried under gentle filtered air flow and stored at −20° C. until HPLC analysis.

Example 15

Bioavailability Assay in Cynomolgus Monkeys

Within 1 week prior to the study initiation, the cynomolgus monkey is surgically implanted with a chronic venous catheter and subcutaneous venous access port (VAP) to facilitate lood collection and underwent a physical examination including hematology and serum chemistry evaluations and the body weight was recorded. Each monkey (six total) receives approximately 250 μCi of ³H activity with each dose of active compound at a dose level of 10 mg/kg at a dose concentration of 5 mg/mL, either via an intravenous olus (3 monkeys, IV), or via oral gavage (3 monkeys, PO). Each dosing syringe is weighed before dosing to gravimetrically determine the quantity of formulation administered. Urine samples are collected via pan catch at the designated intervals (approximately 18-0 hours pre-dose, 0-4, 4-8 and 8-12 hours post-dosage) and processed. blood samples are collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples are analyzed for the maximum concentration ($C_{max}$), time when the maximum concentration is achieved ($T_{max}$), area under the curve (AUC), half life of the dosage concentration ($T_{1/2}$), clearance (CL), steady state volume and distribution ($V_{ss}$) and bioavailability (F).

Example 16

Bone Marrow Toxicity Assay

Human one marrow cells are collected from normal healthy volunteers and the mononuclear population are separated by Ficoll-Hypaque gradient centrifugation as described previously by Sommadossi J-P, Carlisle R. "Toxicity of 3'-azido-3'-deoxythymidine and 9-(1,3-dihydroxy-2-propoxymethyl)guanine for normal human hematopoietic progenitor cells in vitro" Antimicrobial Agents and Chemotherapy 1987; 31:452-454; and Sommadossi J-P, Schinazi R F, Chu C K, Xie M-Y. "Comparison of cytotoxicity of the (−)- and (+)-enantiomer of 2',3'-dideoxy-3'-thiacytidine in normal human one marrow progenitor cells" *Biochemical Pharmacology* 1992; 44:1921-1925. The culture assays for CFU-GM and FU-E are performed using a bilayer soft agar or methylcellulose method. Drugs are diluted in tissue culture medium and filtered. After 14 to 18 days at 37° C. in a humidified atmosphere of 5% $CO_2$ in air, colonies of greater than 50 cells are counted using an inverted microscope. The results are presented as the percent inhibition of colony formation in the presence of drug compared to solvent control cultures.

Example 17

Mitochondria Toxicity Assay

HepG2 cells are cultured in 12-well plates as described above and exposed to various concentrations of drugs as taught by Pan-Zhou X-R, Cui L, Zhou X-J, Sommadossi J-P, Darley-Usmer V M. "Differential effects of antiretroviral nucleoside analogs on mitochondrial function in HepG2 cells" Antimicro Agents Chemother 2000; 44:496-503. Lactic acid levels in the culture medium after 4 day drug exposure are measured using a Boehringer lactic acid assay kit. Lactic acid levels are normalized by cell number as measured by hemocytometer count.

Example 18

Cytotoxicity Assay

Cells are seeded at a rate of between $5\times10^3$ and $5\times10^4$/well into 96-well plates in growth medium overnight at 37° C. in a humidified $CO_2$ (5%) atmosphere. New growth medium containing serial dilutions of the drugs is then added. After incubation for 4 days, cultures are fixed in 50% TCA and stained with sulforhodamine. The optical density was read at 550 nm. The cytotoxic concentration was expressed as the concentration required to reduce the cell number by 50% ($CC_{50}$). The preliminary results are tabulated in the Table 3 below.

TABLE 3

| MDK versus Human Hepatoma | |
|---|---|
| Compound | $CC_{50}$, µM MDK |
| β-D-4'-$CH_3$-riboG | >250 |
| β-D-4'-$CH_3$-ribo-4-thioU | >250 |
| β-D-4'-$CH_3$-riboC | >250 |

TABLE 3-continued

| MDK versus Human Hepatoma | |
|---|---|
| Compound | $CC_{50}$, µM MDK |
| β-D-4'-$CH_3$-ribo-5-fluoroU | >167 |
| β-D-4'-$CH_3$-riboT | >250 |
| β-D-4'-$CH_3$-riboA | >250 |

This invention has been described with reference to its preferred embodiments. Variations and modifications of the invention will be obvious to those skilled in the art from the foregoing detailed description of the invention. It is intended that all of these variations and modifications be included within the scope of this invention.

We claim:

1. A method of treating a host infected with HCV, comprising administering an effective amount of a ribofuranonucleoside of Formula (I):

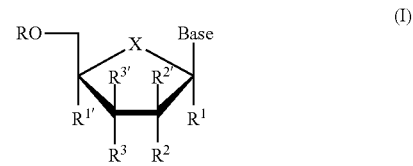

or a pharmacologically acceptable salt thereof,
wherein:
R is H, mono-, di-, or triphosphate; or phosphonate;
X is O, S(O)$_n$, $CH_2$, CHOH, CH-alkyl, CH-alkenyl, CH-alkynyl, C-dialkyl, CH—O-alkyl, CH—O-alkenyl, CH—O-alkynyl, CH—S-alkyl, CH—S-alkenyl, CH—S-alkynyl, NH, N-alkyl, N-alkenyl, N-alkynyl, S(O)NH-alkyl, S(O)NH-alkenyl, S(O)NH-alkynyl, or C-(halogen)$_2$, wherein alkyl, alkenyl, or alkynyl may optionally be substituted;
n is 0-2;
such that when X is $CH_2$, CHOH, CH-alkyl, CH-alkenyl, CH-alkynyl, C-dialkyl, CH—O-alkyl, CH—O-alkenyl, CH—O-alkynyl, CH—S-alkyl, CH—S-alkenyl, CH—S-alkynyl, CH-halogen, or C-(halogen)$_2$;
then each $R^1$ and $R^{1'}$ is independently H, OH, optionally substituted alkyl, lower alkyl, azido, cyano, optionally substituted alkenyl or alkynyl, —C(O)O-(alkyl), —C(O)O(lower alkyl), —C(O)O-(alkenyl), —C(O)O-(alkynyl), —O(acyl), —O(lower acyl), —O(alkyl), —O(lower alkyl), —O(alkenyl), —O(alkynyl), halogen, halogenated alkyl, —$NO_2$, —$NH_2$, —NH(lower alkyl), —N(lower alkyl)$_2$, —NH(acyl), —N(acyl)$_2$, —C(O)$NH_2$, —C(O)NH(alkyl), —C(O)N(alkyl)$_2$, S(O)NH-alkyl, S(O)NH-alkenyl, or S(O)NH-alkynyl; wherein alkyl, alkenyl, and/or alkynyl may optionally be substituted; and
such that when X is O, S(O)$_n$, NH, N-alkyl, N-alkenyl, N-alkynyl, S(O)NH-alkyl, S(O)NH-alkenyl, or S(O)NH-alkynyl;
then each $R^1$ and $R^{1'}$ is independently H, optionally substituted alkyl, lower alkyl, azido, cyano, optionally substituted alkenyl or alkynyl, —C(O)O-(alkyl), —C(O)O (lower alkyl), —C(O)O-(alkenyl), —C(O)O-(alkynyl), halogenated alkyl, —C(O)$NH_2$, —C(O)NH(alkyl), —C(O)N(alkyl)$_2$, —C(H)=N—$NH_2$, C(S)$NH_2$, C(S)

NH(alkyl), or C(S)N(alkyl)₂, wherein alkyl, alkenyl, and/or alkynyl may optionally be substituted;

each R² and R³ independently is OH, NH₂, SH, F, Cl, Br, I, CN, NO₂, —C(O)NH₂, —C(O)NH(alkyl), —C(O)N(alkyl)₂, N₃, optionally substituted alkyl, lower alkyl, optionally substituted alkenyl or alkynyl, halogenated alkyl, —C(O)O-(alkyl), —C(O)O(lower alkyl), —C(O)O-(alkenyl), —C(O)O-(alkynyl), —O(acyl), —O(alkyl), —O(alkenyl), —O(alkynyl), —OC(O)NH₂, NC, C(O)OH, SCN, OCN, —S(alkyl), —S(alkenyl), —S(alkynyl), —NH(alkyl), —N(alkyl)₂, —NH(alkenyl), —NH(alkynyl), or an optionally substituted 3-7 membered heterocyclic ring having O, S, and/or N independently as a heteroatom taken alone or in combination;

R²'; is alkyl, alkenyl, or alkynyl;

R³' is H; and

Base is selected from the group consisting of:

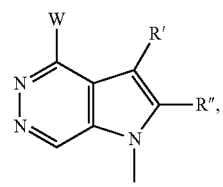

(iii)

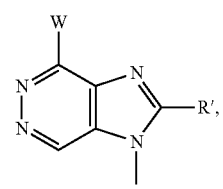

(iv)

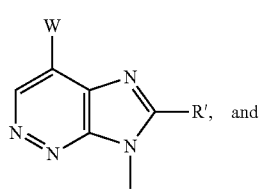

(v)

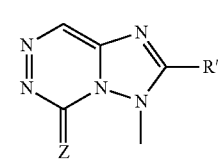

(x)

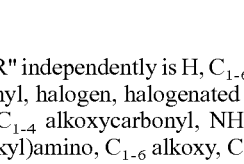

wherein each R' and R" independently is H, C₁₋₆ alkyl, C₂₋₆ alkenyl, C₂₋₆ alkynyl, halogen, halogenated alkyl, OH, CN, N₃, carboxy, C₁₋₄ alkoxycarbonyl, NH₂, C₁₋₄ alkylamino, di(C₁₋₄ alkyl)amino, C₁₋₆ alkoxy, C₁₋₆ alkylsulfonyl, or (C₁₋₄ alkyl)₀₋₂ aminomethyl;

each W is Cl, Br, I, F, halogenated alkyl, alkoxy, OH, SH, O-alkyl, S-alkyl, O-alkenyl, O-alkynyl, S-alkenyl, S-alkynyl, —OC(O)NR⁴R⁴, O-acyl, S-acyl, CN, SCN, OCN, NO₂, N₃, NH₂, NH(alkyl), N(alkyl)₂, NH-cycloalkyl, NH-acyl, CONH₂, CONH(alkyl), or CON(alkyl)₂; each R⁴ is independently H, acyl, or C₁₋₆ alkyl; and each Z is O, S, or NH.

2. A method of treating a host infected with HCV, comprising administering an effective amount of a ribofuranonucleoside of Formula (III):

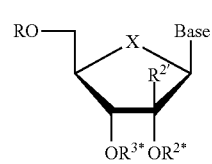

(III)

or a pharmacologically acceptable salt thereof, wherein:

each R, R²*, and R³* independently is H, mono-, di-, or triphosphate; or phosphonate; optionally substituted alkyl, lower alkyl, optionally substituted alkenyl or alkynyl, acyl, —C(O)-(alkyl), —C(O)(lower alkyl), —C(O)-(alkenyl), or —C(O)-(alkynyl);

X is O, S(O)ₙ, CH₂, CHOH, CH-alkyl, CH-alkenyl, CH-alkynyl, C-dialkyl, CH—O-alkyl, CH—O-alkenyl, CH—O-alkynyl, CH—S-alkyl, CH—S-alkenyl, CH—S-alkynyl, NH, N-alkyl, N-alkenyl, N-alkynyl, S(O)N-alkyl, S(O)N-alkenyl, S(O)N-alkynyl, or C-(halogen)₂, wherein alkyl, alkenyl, or alkynyl is optionally substituted;

n is 0-2;

R²' is alkyl, alkenyl, or alkynyl; and

Base is selected from the group consisting of:

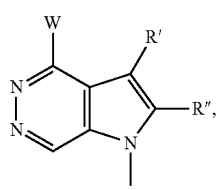

(iii)

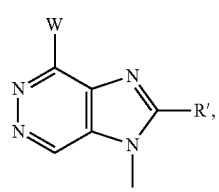

(iv)

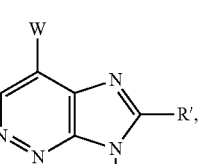

(v)

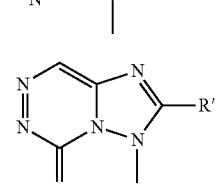

(x)

wherein each R' and R" independently is H, C₁₋₆ alkyl, C₂₋₆ alkenyl, C₂₋₆ alkynyl, halogen, halogenated alkyl, OH, CN, N₃, carboxy, C₁₋₄ alkoxycarbonyl, NH₂, C₁₋₄ alkylamino, di(C₁₋₄ alkyl)amino, C₁₋₆ alkoxy, C₁₋₆ alkylsulfonyl, or (C₁₋₄ alkyl)₀₋₂ aminomethyl;

each W is Cl, Br, I, F, halogenated alkyl, alkoxy, OH, SH, O-alkyl, S-alkyl, O-alkenyl, O-alkynyl, S-alkenyl, S-alkynyl, —OC(O)NR⁴R⁴, O-acyl, S-acyl, CN, SCN, OCN, NO₂, N₃, NH₂, NH(alkyl), N(alkyl)₂, NH-cycloalkyl, NH-acyl, CONH₂, CONH(alkyl), or CON(alkyl)₂;

each $R^4$ is independently H, acyl, or $C_{1-6}$ alkyl; and each Z is O, S, or NH.

3. The method of claim 2, wherein $R^{2'}$ is alkyl.

4. The method of claim 2, wherein $R^2$ is $CH_3$.

5. The method of claim 4, wherein each R, $R^{2*}$, and $R^{3*}$ is independently H, mono-, di-, or triphosphate, or phosphonate.

6. The method of claim 4, wherein each R, $R^{2*}$, and $R^{3*}$ is H.

7. The method of claim 4, wherein each R, $R^{2*}$, and $R^{3*}$ is independently H, or acyl.

8. The method of claim 5, wherein X is O or S.

9. The method of claim 7, wherein X is O.

10. A compound of the general structure of Formula (III):

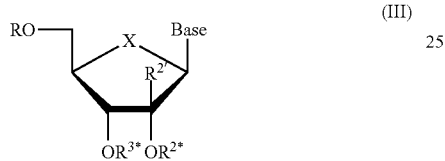

(III)

or a pharmacologically acceptable salt thereof, wherein:

each R, $R^{2*}$, and $R^{3*}$ independently is H, mono-, di-, or triphosphate; or phosphonate; optionally substituted alkyl, lower alkyl, optionally substituted alkenyl or alkynyl, acyl, —C(O)-(alkyl), —C(O)(lower alkyl), —C(O)-(alkenyl), or —C(O)-(alkynyl);

X is O, $S(O)_n$, $CH_2$, CHOH, CH-alkyl, CH-alkenyl, CH-alkynyl, C-dialkyl, CH—O-alkyl, CH—O-alkenyl, CH—O-alkynyl, CH—S-alkyl, CH—S-alkenyl, CH—S-alkynyl, NH, N-alkyl, N-alkenyl, N-alkynyl, S(O)NH-alkyl, S(O)NH-alkenyl, S(O)NH-alkynyl, or C-(halogen)₂, wherein alkyl, alkenyl, or alkynyl is optionally substituted;

n is 0-2;

$R^{2'}$ is alkyl, alkenyl, or alkynyl; and

Base is selected from the group consisting of:

(iii)

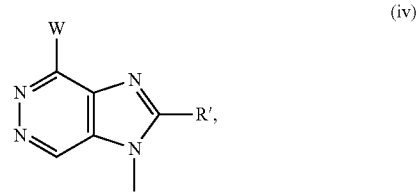

(iv)

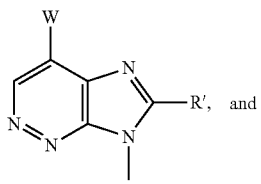

(v)

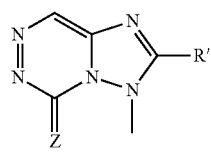

(x)

wherein
each R' and R" independently is H, $C_{1-6}$ alkyl, $C_{2-6}$ alkenyl, $C_{2-6}$ alkynyl, halogen, halogenated alkyl, OH, CN, N₃, carboxy, $C_{1-4}$ alkoxycarbonyl, NH₂, $C_{1-4}$ alkylamino, di($C_{1-4}$ alkyl)amino, $C_{1-6}$ alkoxy, $C_{1-6}$ alkylsulfonyl, or $(C_{1-4}$ alkyl$)_{0-2}$ aminomethyl;

each W is Cl, Br, I, F, halogenated alkyl, alkoxy, OH, SH, O-alkyl, S-alkyl, O-alkenyl, O-alkynyl, S-alkenyl, S-alkynyl, —OC(O)NR⁴R⁴, O-acyl, S-acyl, CN, SCN, OCN, NO₂, N₃, NH₂, NH(alkyl), N(alkyl)₂, NH-cycloalkyl, NH-acyl, CONH₂, CONH(alkyl), or CON(alkyl)₂; each $R^4$ is independently H, acyl, or $C_{1-6}$ alkyl; and each Z is O, S, or NH.

11. The compound of claim 10, wherein $R^{2'}$ is alkyl.

12. The compound of claim 10, wherein $R^2$ is $CH_3$.

13. The compound of claim 12, wherein each R, $R^{2*}$, and $R^{3*}$ is independently H, mono-, di-, or triphosphate, or phosphonate.

14. The compound of claim 12, wherein each R, $R^{2*}$, and $R^{3*}$ is H.

15. The compound of claim 12, wherein R, $R^{2*}$, and $R^{3*}$ is independently H, or acyl.

16. The compound of claim 13, wherein X is O or S.

17. The compound of claim 13, wherein X is O.

18. A pharmaceutical composition comprising an anti-virally effective amount of a compound of claim 10, optionally with a pharmaceutically acceptable carrier, diluent or excipient.

19. The pharmaceutical composition of claim 18, wherein the compound or salt thereof is in the form of a dosage unit.

20. The pharmaceutical composition of claim 19, wherein the dosage unit contains from about 50 to about 1000 mg of the compound.

21. The pharmaceutical composition of claim 20, wherein said dosage unit is a tablet or capsule.

22. The pharmaceutical composition of claim 18, further comprising one or more additional anti-virally effective agents.

23. The pharmaceutical composition of claim 22, wherein the additional anti-virally agent is an interferon, ribavirin, an interleukin, an NS3 protease inhibitor, a cysteine protease inhibitor, a thiazolidine derivative, a thiazolidine, a benzanilide, phenanthrenequinone, a helicase inhibitor, a polymerase inhibitor, a nucleotide analogue, gliotoxin, cerulenin, an antisense oligodeoxynucleotide, an inhibitor of IRES-dependent translation, or a ribozyme.

24. The pharmaceutical composition of claim 18, wherein the compound is in substantially pure form.

25. The pharmaceutical composition of claim 24, wherein the compound is at least 90% by weight of the β-D-isomer.

26. The pharmaceutical composition of claim 24, wherein the compound is at least 95% by weight of the β-D-isomer.

27. The pharmaceutical composition of claim 24, wherein the compound is at least 90% by weight of the β-L-isomer.

28. The pharmaceutical composition of claim 24, wherein the compound is at least 95% by weight of the β-L-isomer.

\* \* \* \* \*